(12) United States Patent
Hanson et al.

(10) Patent No.: US 9,610,405 B2
(45) Date of Patent: Apr. 4, 2017

(54) CONNECTION AND ALIGNMENT DETECTION SYSTEMS AND METHODS

(71) Applicant: Medtronic MiniMed, Inc., Northridge, CA (US)

(72) Inventors: Ian B. Hanson, Wayne, PA (US); Paul F. Bente, IV, South Pasadena, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 519 days.

(21) Appl. No.: 13/791,773

(22) Filed: Mar. 8, 2013

(65) Prior Publication Data

US 2013/0190683 A1   Jul. 25, 2013

Related U.S. Application Data

(63) Continuation of application No. 13/235,288, filed on Sep. 16, 2011, now Pat. No. 8,435,209, which is a
(Continued)

(51) Int. Cl.
*A61M 5/14* (2006.01)
*A61M 5/172* (2006.01)
(Continued)

(52) U.S. Cl.
CPC .......... *A61M 5/172* (2013.01); *A61M 5/1413* (2013.01); *A61M 5/14248* (2013.01);
(Continued)

(58) Field of Classification Search
CPC .............. A61M 5/5086; A61M 5/1413; A61M 2205/6018; A61M 2205/6027; A61M 2205/6054
(Continued)

(56) References Cited

U.S. PATENT DOCUMENTS 3,701,345 A   10/1972   Heilman et al.
3,884,230 A    5/1975   Wulff
(Continued)

FOREIGN PATENT DOCUMENTS

DE   31 44 825    5/1983
EP   0 092 712   11/1983
(Continued)

OTHER PUBLICATIONS

Partial Search Report dated Jun. 7, 2011, from related international application No. PCT/US2010/062414.
(Continued)

*Primary Examiner* — Theodore Stigell
*Assistant Examiner* — Benjamin Koo
(74) *Attorney, Agent, or Firm* — Foley & Lardner LLP

(57) ABSTRACT

A medical device includes a first housing portion (FHP) and a second housing portion (SHP) configured to be to be movable relative to each other from a first position to operatively engage at a second position to couple at least one of a drive device and a needle-inserting device supported by one of the FHP and the SHP to a reservoir supported by the other of the FHP and the SHP. Electronic circuitry configured to detect at least one of a first magnetic interaction between a magnet and at least one of a first magnetically attractive material and a first magnet-responsive device and a second magnetic interaction between the magnet and at least one of a second magnetically attractive material and a second magnet-responsive device, and to provide a signal or a change in state in response to detecting at least one of the interactions.

25 Claims, 53 Drawing Sheets

Related U.S. Application Data continuation-in-part of application No. 12/649,619, filed on Dec. 30, 2009, now Pat. No. 8,308,679, and a continuation-in-part of application No. 13/103,014, filed on May 6, 2011, now Pat. No. 9,421,321, which is a continuation-in-part of application No. 12/650,378, filed on Dec. 30, 2009, now Pat. No. 8,998,840.

(60) Provisional application No. 61/332,318, filed on May 7, 2010.

(51) Int. Cl.
    *A61M 5/168*      (2006.01)
    *A61M 5/142*      (2006.01)
    *A61M 5/50*      (2006.01)
    *A61M 5/145*      (2006.01)

(52) U.S. Cl.
    CPC ........ *A61M 5/1684* (2013.01); *A61M 5/5086* (2013.01); *A61M 5/1456* (2013.01); *A61M 2005/14268* (2013.01); *A61M 2205/3389* (2013.01); *A61M 2205/581* (2013.01); *A61M 2205/582* (2013.01); *A61M 2205/583* (2013.01); *A61M 2205/6018* (2013.01); *A61M 2205/6027* (2013.01); *A61M 2205/6036* (2013.01); *A61M 2205/6045* (2013.01); *A61M 2205/6054* (2013.01); *A61M 2205/6063* (2013.01); *A61M 2205/6072* (2013.01); *A61M 2205/6081* (2013.01); *Y10T 29/49117* (2015.01)

(58) Field of Classification Search
    USPC ............................ 604/67, 131, 151, 216, 506
    See application file for complete search history.

(56) References Cited

U.S. PATENT DOCUMENTS

| | | |
|---|---|---|
| 3,994,295 A | 11/1976 | Wulff |
| 4,633,232 A | 12/1986 | Nelson et al. |
| 5,122,123 A | 6/1992 | Vaillancourt |
| 5,176,662 A | 1/1993 | Bartholomew et al. |
| 5,236,416 A | 8/1993 | McDaniel et al. |
| 5,334,188 A | 8/1994 | Inoue et al. |
| 5,533,981 A | 7/1996 | Mandro et al. |
| 5,628,309 A | 5/1997 | Brown |
| 5,662,612 A | 9/1997 | Niehoff |
| 5,954,697 A | 9/1999 | Srisathapat et al. |
| 6,283,943 B1 * | 9/2001 | Dy et al. ...................... 604/141 |
| 6,299,131 B1 | 10/2001 | Ryan |
| 6,416,402 B1 | 7/2002 | Moore |
| 6,423,035 B1 | 7/2002 | Das et al. |
| 6,461,329 B1 | 10/2002 | Van Antwerp et al. |
| 6,699,218 B2 * | 3/2004 | Flaherty et al. .............. 604/131 |
| 6,727,689 B1 | 4/2004 | Furlong et al. |
| 6,740,059 B2 * | 5/2004 | Flaherty ........................ 604/67 |
| 6,749,587 B2 * | 6/2004 | Flaherty ........................ 604/151 |
| 6,830,558 B2 | 12/2004 | Flaherty et al. |
| 6,945,760 B2 * | 9/2005 | Gray et al. .................... 417/417 |
| 6,960,192 B1 | 11/2005 | Flaherty et al. |
| 7,018,360 B2 * | 3/2006 | Flaherty et al. .............. 604/123 |
| 7,396,353 B2 | 7/2008 | Lorenzen et al. |
| 7,811,279 B2 | 10/2010 | John |
| 7,935,104 B2 | 5/2011 | Yodfat et al. |
| 8,105,279 B2 * | 1/2012 | Mernoe et al. ............... 604/131 |
| 8,152,771 B2 | 4/2012 | Mogensen et al. |
| 8,308,679 B2 * | 11/2012 | Hanson et al. ................ 604/67 |
| 8,435,209 B2 | 5/2013 | Hanson et al. |
| 8,858,500 B2 | 10/2014 | Hanson et al. |
| 8,882,710 B2 | 11/2014 | Chong et al. |
| 8,900,190 B2 | 12/2014 | Chong et al. |
| 8,998,840 B2 | 4/2015 | Hanson et al. |
| 8,998,858 B2 | 4/2015 | Chong et al. |
| 9,039,653 B2 | 5/2015 | Chong et al. |
| 9,039,659 B2 | 5/2015 | Hanson et al. |
| 2001/0034506 A1 | 10/2001 | Hirschman et al. |
| 2001/0041869 A1 | 11/2001 | Causey et al. |
| 2003/0007891 A1 | 1/2003 | Wilson |
| 2004/0002682 A1 | 1/2004 | Kovelman et al. |
| 2004/0162521 A1 | 8/2004 | Bengtsson |
| 2004/0204673 A1 | 10/2004 | Flaherty |
| 2005/0065472 A1 | 3/2005 | Cindrich et al. |
| 2005/0101932 A1 | 5/2005 | Cote et al. |
| 2006/0061353 A1 | 3/2006 | Etherington et al. |
| 2006/0079765 A1 | 4/2006 | Neer et al. |
| 2006/0200020 A1 | 9/2006 | Brister et al. |
| 2007/0049865 A1 | 3/2007 | Radmer et al. |
| 2007/0060871 A1 | 3/2007 | Istoc et al. |
| 2007/0073236 A1 | 3/2007 | Mernoe et al. |
| 2007/0156094 A1 | 7/2007 | Safabash et al. |
| 2007/0191702 A1 | 8/2007 | Yodfat et al. |
| 2007/0191770 A1 | 8/2007 | Moberg et al. |
| 2007/0270744 A1 | 11/2007 | Dacquay et al. |
| 2008/0024812 A1 | 1/2008 | Miyazaki et al. |
| 2008/0051697 A1 | 2/2008 | Mounce et al. |
| 2008/0051711 A1 | 2/2008 | Mounce et al. |
| 2008/0051714 A1 | 2/2008 | Moberg et al. |
| 2008/0077081 A1 | 3/2008 | Mounce et al. |
| 2008/0097321 A1 | 4/2008 | Mounce et al. |
| 2008/0097328 A1 | 4/2008 | Moberg et al. |
| 2008/0097381 A1 * | 4/2008 | Moberg et al. ............... 604/506 |
| 2008/0269687 A1 | 10/2008 | Chong et al. |
| 2008/0281270 A1 | 11/2008 | Cross et al. |
| 2008/0319394 A1 | 12/2008 | Yodfat et al. |
| 2008/0319414 A1 | 12/2008 | Yodfat et al. |
| 2009/0054810 A1 | 2/2009 | Zanzucchi et al. |
| 2009/0069750 A1 | 3/2009 | Schraga |
| 2009/0156990 A1 | 6/2009 | Wenger et al. |
| 2009/0182301 A1 | 7/2009 | Bassarab et al. |
| 2009/0216194 A1 | 8/2009 | Pedersen et al. |
| 2009/0259183 A1 | 10/2009 | Chong et al. |
| 2009/0259198 A1 | 10/2009 | Chong et al. |
| 2009/0264825 A1 | 10/2009 | Cote |
| 2009/0326458 A1 | 12/2009 | Chong et al. |
| 2010/0070878 A1 | 3/2010 | Amento et al. |
| 2010/0137790 A1 | 6/2010 | Yodfat |
| 2010/0152658 A1 | 6/2010 | Hanson et al. |
| 2010/0274180 A1 | 10/2010 | Donovan et al. |
| 2011/0025715 A1 | 2/2011 | Uchida et al. |
| 2011/0166512 A1 | 7/2011 | Both et al. |
| 2011/0178461 A1 | 7/2011 | Chong et al. |
| 2011/0213306 A1 * | 9/2011 | Hanson et al. ............... 604/151 |
| 2012/0130312 A1 * | 5/2012 | Mernoe et al. ............... 604/152 |
| 2012/0215163 A1 | 8/2012 | Hanson et al. |
| 2013/0253422 A1 | 9/2013 | Hanson et al. |

FOREIGN PATENT DOCUMENTS

| | | |
|---|---|---|
| EP | 0 317 808 | 5/1989 |
| EP | 0 937 475 | 8/1999 |
| EP | 1 752 172 | 2/2007 |
| EP | 2 077 128 | 12/2010 |
| EP | 2 375 342 | 10/2011 |
| EP | 1 177 802 | 6/2013 |
| GB | 2 327 151 | 1/1999 |
| JP | 11-339439 | 12/1999 |
| KR | 10-0692005 | 3/2007 |
| KR | 10-200901067 | 10/2009 |
| WO | WO-86/02562 | 5/1986 |
| WO | WO-99/33504 | 7/1999 |
| WO | WO-00/47254 | 8/2000 |
| WO | WO-01/68163 | 9/2001 |
| WO | WO-2006/031500 | 3/2006 |
| WO | WO-2006/076656 | 7/2006 |
| WO | WO-2006/121921 | 11/2006 |
| WO | WO-2006/122406 | 11/2006 |
| WO | WO-2006/124756 | 11/2006 |
| WO | WO-2008/024810 | 2/2008 |
| WO | WO-2008/024812 | 2/2008 |
| WO | WO-2008/024814 | 2/2008 |
| WO | WO-2009/001346 | 2/2008 |
| WO | WO 2008024814 A2 * | 2/2008 .............. A61M 5/14 |

(56) References Cited

FOREIGN PATENT DOCUMENTS

| WO | WO-2008/078318 | 7/2008 |
|---|---|---|
| WO | WO-2008/092782 | 8/2008 |
| WO | WO-2008/133702 | 11/2008 |
| WO | WO-2009/016638 | 2/2009 |
| WO | WO-2009/033032 | 3/2009 |
| WO | WO-2009/066288 | 5/2009 |
| WO | WO-2009/093759 | 7/2009 |
| WO | WO-2009/098291 | 8/2009 |
| WO | WO-2009/106517 | 9/2009 |
| WO | WO-2009/125398 | 10/2009 |
| WO | WO-2009/135667 | 11/2009 |
| WO | WO-2009/144726 | 12/2009 |
| WO | WO-2010/042814 | 4/2010 |
| WO | WO-2011/082256 | 7/2011 |
| WO | WO-2011/090629 | 7/2011 |
| WO | WO-2011/119768 | 9/2011 |

OTHER PUBLICATIONS

International Search Report and Written Opinion dated Dec. 6, 2011, from related international application No. PCT/US2010/062414.
International Search Report and Written Opinion dated Mar. 1, 2011, from related international application No. PCT/US2010/060892.
Partial Search Report dated Mar. 21, 2011, from related international application No. PCT/US2010/060895.
International Search Report and Written Opinion dated Mar. 29, 2013, related international application No. PCT/US2010/060895.
Partial Search Report dated Mar. 23, 2011, from related international application No. PCT/US2010/047590.
International Search Report and Written Opinion dated Sep. 6, 2011, from related international application No. PCT/US2010/047590.
Partial Search Report dated Jul. 9, 2012, from related international application No. PCT/US2011/066501.
International Search Report and Written Opinion dated Dec. 12, 2012, from related international application No. PCT/US2011/066501.
Partial Search Report dated Apr. 16, 2012, from related international application No. PCT/US2011/066504.
International Search Report and Written Opinion dated Oct. 24, 2012, from related international application No. PCT/US2011/066504.
Partial Search Report dated May 4, 2012, from related international application No. PCT/US2012/022881.
International Search Report and Written Opinion dated Aug. 28, 2012, from related international application No. PCT/US2012/022881.
Partial Search Report dated May 4, 2012, from related international application No. PCT/US2012/022883.
International Search Report and Written Opinion dated Aug. 7, 2012, from related international application No. PCT/US2012/022883.
International Search Report and Written Opinion dated Dec. 11, 2012, from related international application No. PCT/US2012/055661.
Partial Search Report dated Feb. 2, 2013, from related international application No. PCT/US2012/064454.
International Search Report and Written Opinion dated Jun. 12, 2013, from related international application No. PCT/US2012/064454.
US Office Action dated Feb. 2, 2012, from related U.S. Appl. No. 12/553,038.
US Office Action dated Jul. 20, 2012, from related U.S. Appl. No. 12/553,038.
US Office Action dated Jun. 20, 2012, from related U.S. Appl. No. 12/553,038.
US Office Action dated Dec. 22, 2011, from related U.S. Appl. No. 12/649,619.
US Office Action dated Aug. 16, 2012, from related U.S. Appl. No. 12/649,619.
US Notice of Allowance dated Sep. 19, 2012, from related U.S. Appl. No. 12/649,619.
US Office Action dated Jun. 18, 2012, from related U.S. Appl. No. 12/650,287.
US Office Action dated Jul. 20, 2012, from related U.S. Appl. No. 12/650,378.
US Office Action dated Mar. 3, 2011, from related U.S. Appl. No. 12/649,172.
US Office Action dated Oct. 7, 2010, from related U.S. Appl. No. 12/649,172.
US Office Action dated Jun. 19, 2012, from related U.S. Appl. No. 12/649,172.
US Office Action dated Aug. 1, 2012, from related U.S. Appl. No. 13/015,028.
US Office Action dated Aug. 2, 2012, from related U.S. Appl. No. 13/015,051.
US Office Action dated Aug. 2, 2012, from related U.S. Appl. No. 12/974,106.
US Office Action dated Aug. 2, 2012, from related U.S. Appl. No. 12/974,117.
US Notice of Allowance dated Dec. 20, 2012, from related U.S. Appl. No. 13/235,288.
US Office Action dated May 22, 2013, from related U.S. Appl. No. 13/103,014.
U.S. Notice of Allowance dated Oct. 20, 2014, from related U.S. Appl. No. 12/974,106.
U.S. Office Action dated Oct. 9, 2014, from related U.S. Appl. No. 12/974,117.
US Notice of Allowance dated Jul. 7, 2014, from related U.S. Appl. No. 12/650,287.
US Office Action dated Jun. 24, 2014, from related U.S. Appl. No. 12/649,172.
US Notice of Allowance dated Jul. 24, 2014, from related U.S. Appl. No. 13/015,028.
US Office Action dated Jul. 1, 2014, from related U.S. Appl. No. 12/974,106.
Japanese Office Action from related Japanese Patent Application No. 2012-528022, issued Mar. 25, 2014, 3 pages.
U.S. Office Action dated Sep. 5, 2014, from related U.S. Appl. No. 12/650,378.
U.S. Notice of Allowance dated Sep. 22, 2014, from related U.S. Appl. No. 13/015,051.
U.S. Office Action dated Sep. 11, 2014, from related U.S. Appl. No. 13/462,752.
U.S. Office Action dated Sep. 8, 2014, from related patent application No. 13/421,564.
U.S. Notice of Allowance dated Dec. 19, 2014, from related U.S. Appl. No. 12/650,378.
U.S. Office Action dated Jan. 9, 2015, from related U.S. Appl. No. 12/649,172.
U.S. Notice of Allowance dated Jan. 21, 2015, from related U.S. Appl. No. 13/421,564.
U.S. Office Action dated Jan. 16, 2015, from related U.S. Appl. No. 13/462,752.
International Preliminary Report on Patentability dated Mar. 6, 2012, from related international patent application No. PCT/US2010/047590.
International Preliminary Report on Patentability dated May 20, 2014, from related international application No. PCT/US2012/064454.
International Search Report dated Jul. 13, 2011, from related international application No. PCT/US2010/060895.
US Notice of Allowance Aug. 1, 2014, from related U.S. Appl. No. 12/553,038.
US Notice of Allowance dated Feb. 2, 2015, from related U.S. Appl. No. 12/974,117.
US Notice of Allowance dated Nov. 6, 2015, from U.S. Appl. No. 12/649,172.
US Notice of Allowance dated Sep. 25, 2015, from related U.S. Appl. No. 13/103,014.

(56) References Cited

OTHER PUBLICATIONS

US Office Action dated Apr. 25, 2016, from related U.S. Appl. No. 13/900,463.
US Office Action dated Dec. 28, 2012, from related U.S. Appl. No. 12/553,038.
US Office Action dated Feb. 10, 2016, from related U.S. Appl. No. 13/462,752.
US Office Action dated Jan. 16, 2015, from related U.S. Appl. No. 13/791,773.
US Office Action dated Jul. 16, 2015, from related U.S. Appl. No. 13/103,014.
US Office Action dated Jun. 20, 2013, from related U.S. Appl. No. 12/553,038.
US Office Action dated May 28, 2015, from related U.S. Appl. No. 13/462,752.
US Office Action dated Nov. 6, 2013, from related U.S. Appl. No. 13/462,752.
US Office Action dated Sep. 30, 2015, from related U.S. Appl. No. 13/462,752.
US Notice of Allowance dated May 20, 2016, from related U.S. Appl. No. 12/649,172.
US Notice of Allowance dated May 20, 2016, from related U.S. Appl. No. 13/103,014.
US Notice of Allowance dated Aug. 19, 2016, from related U.S. Appl. No. 13/900,463.
US Notice of Allowance dated Aug. 25, 2016, from related U.S. Appl. No. 14/720,663.
US Office Action dated Oct. 27, 2016, from related U.S. Appl. No. 13/462,752.

* cited by examiner

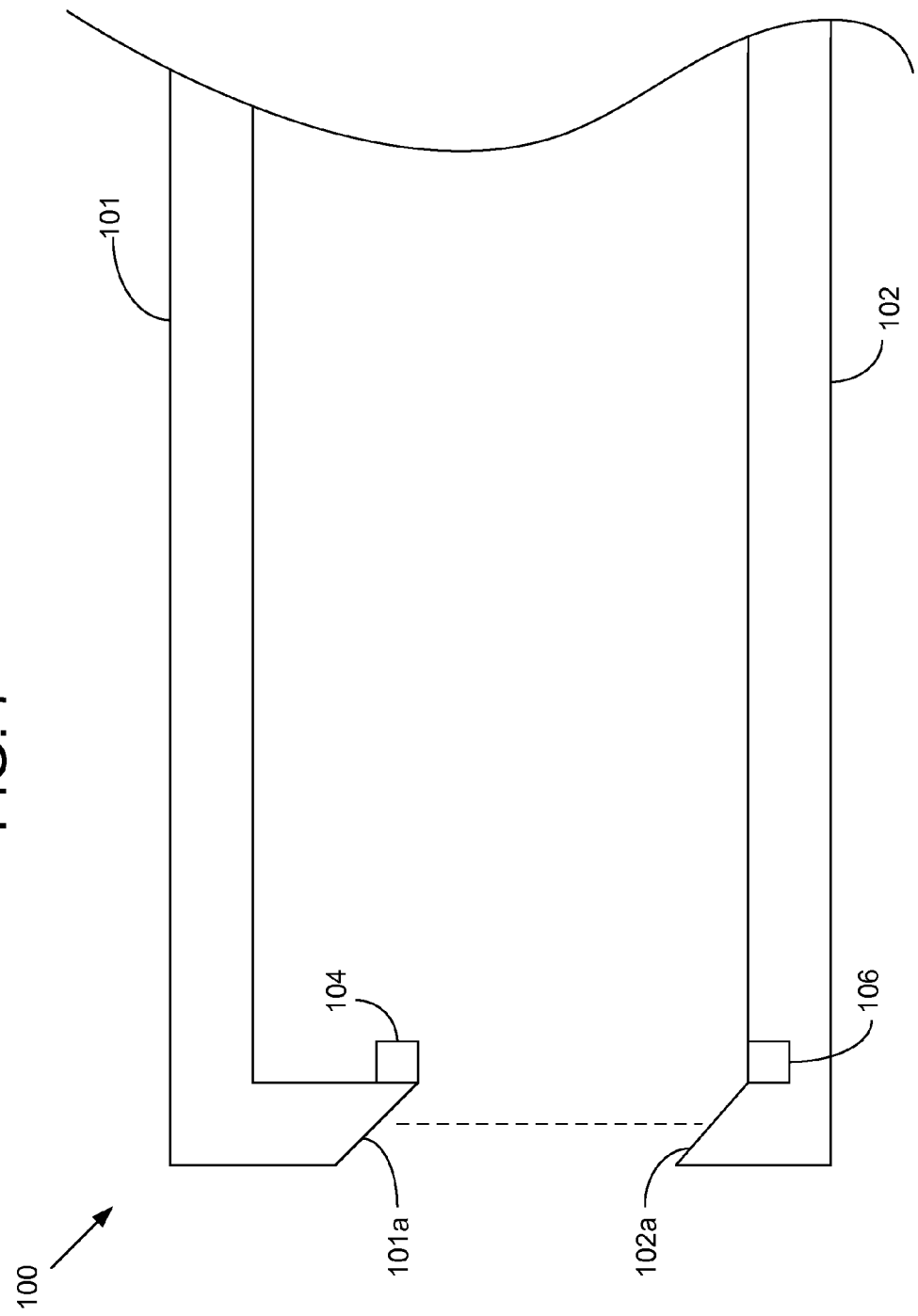

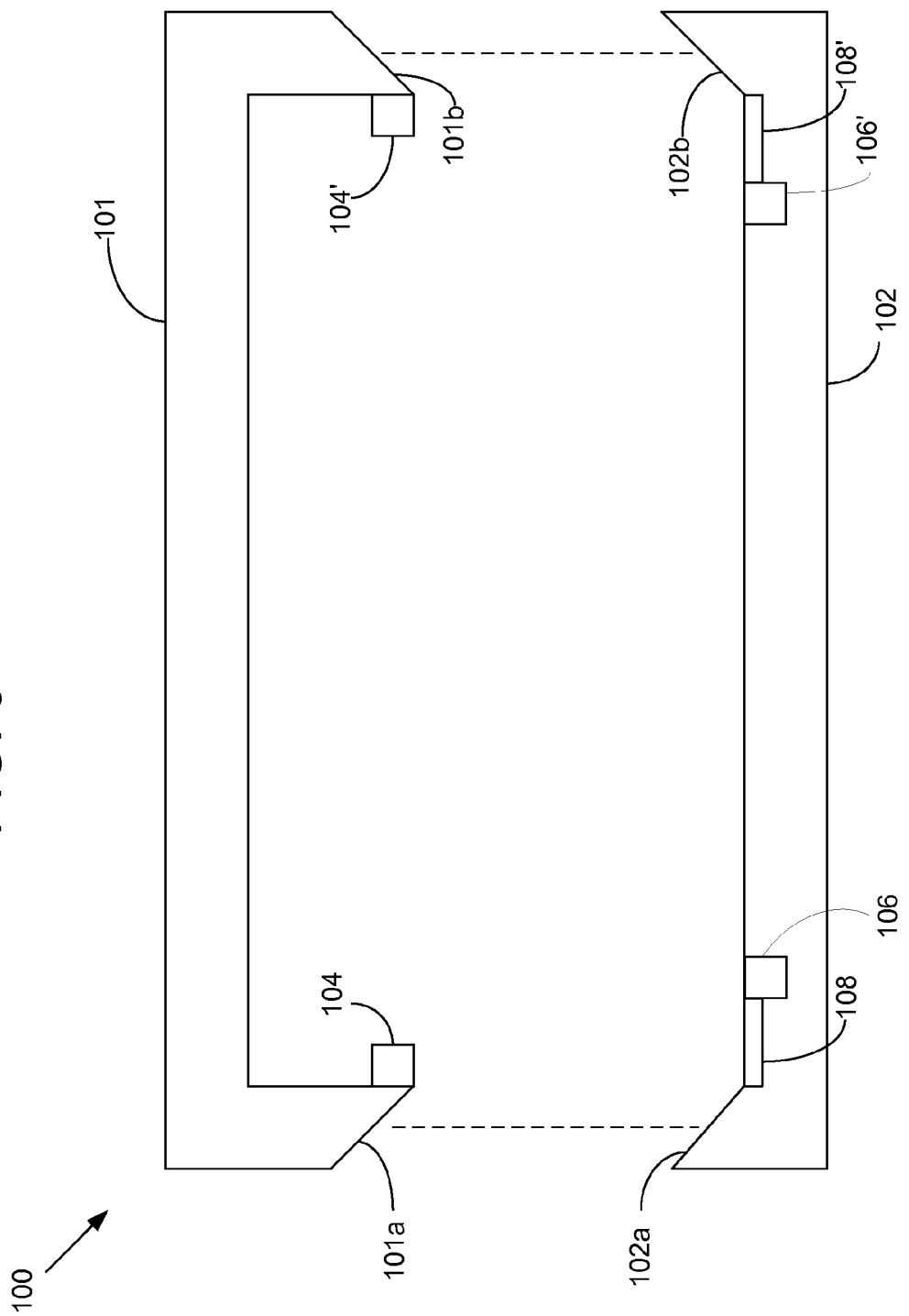

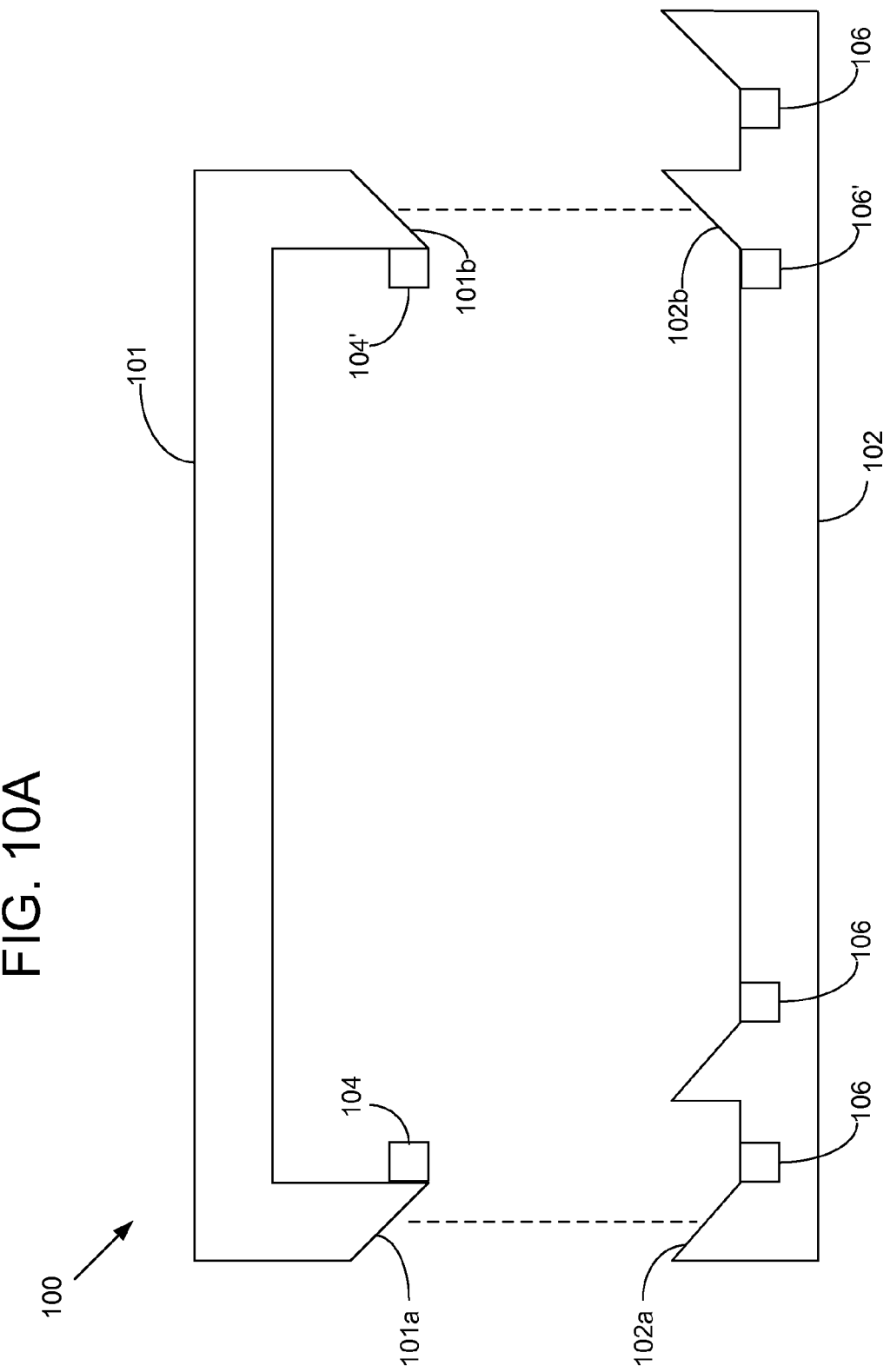

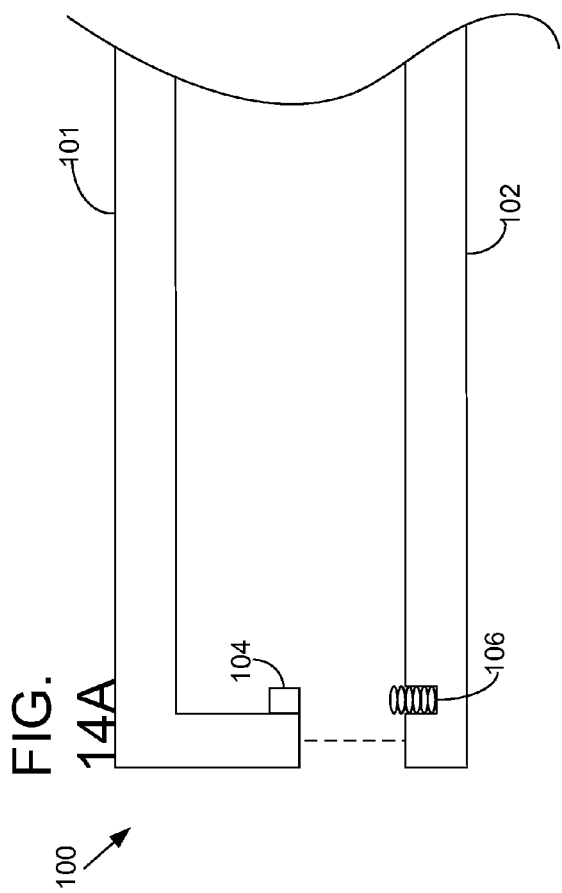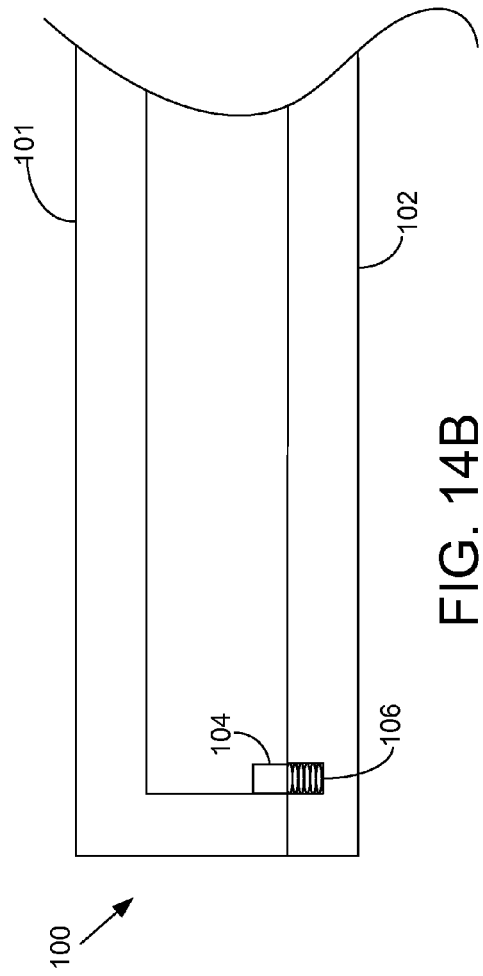

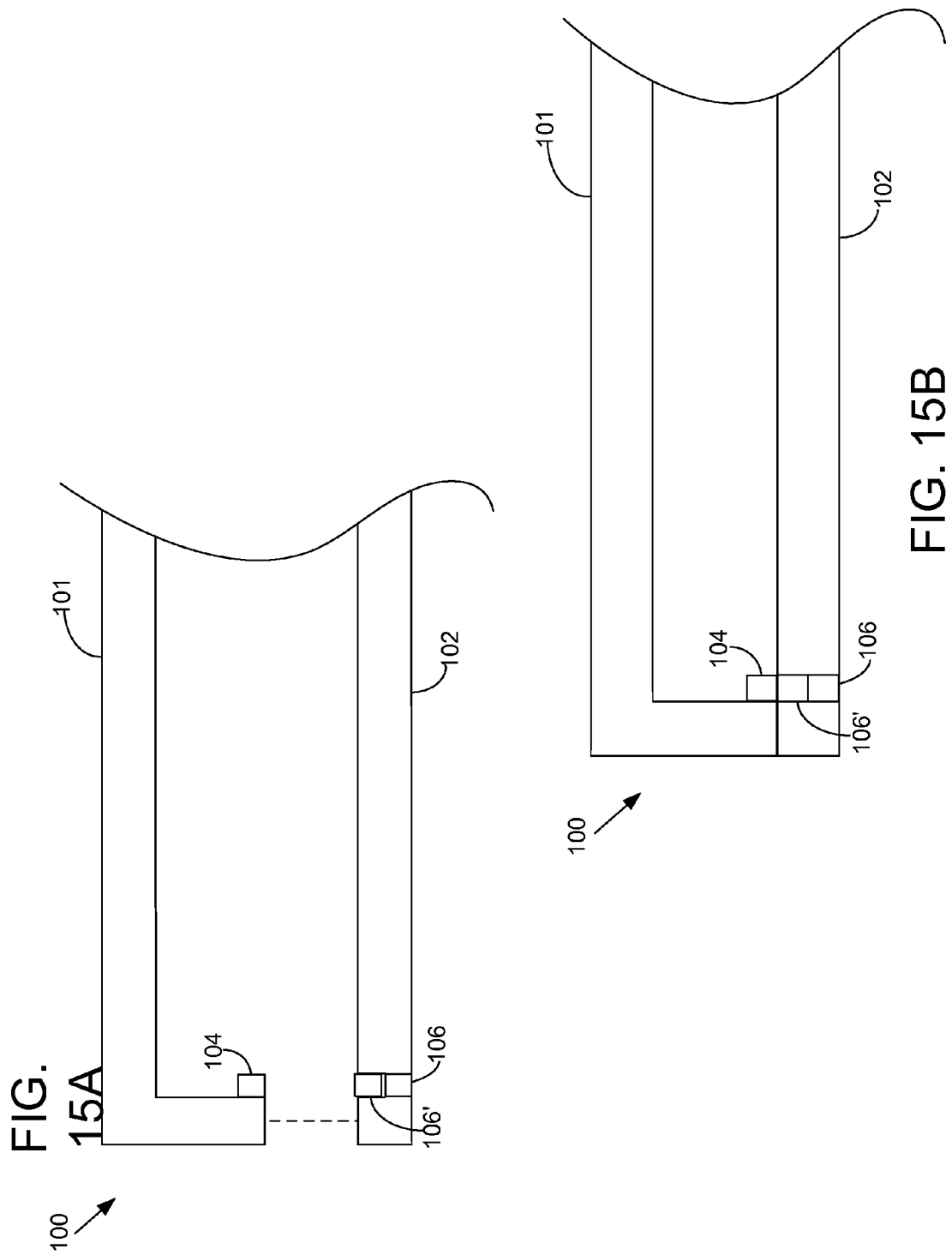

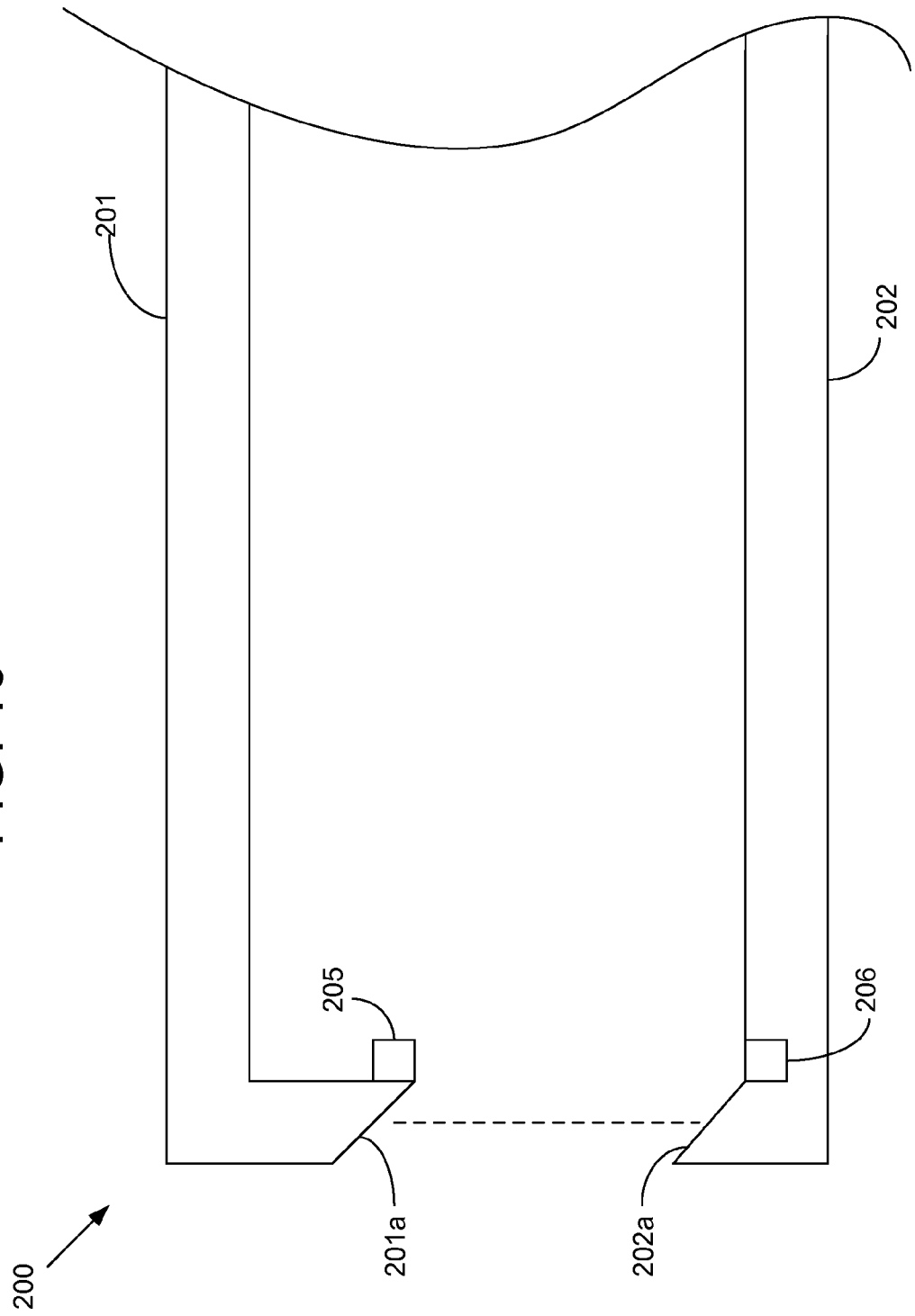

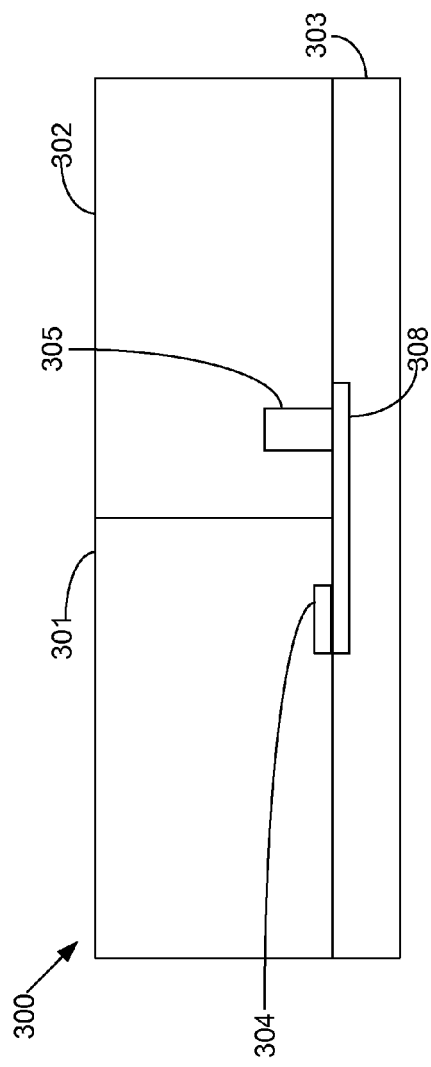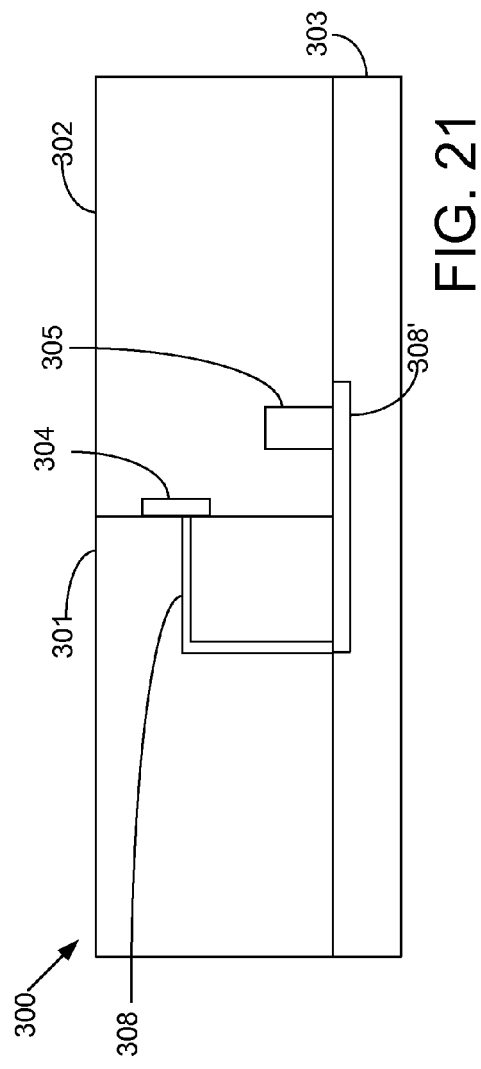

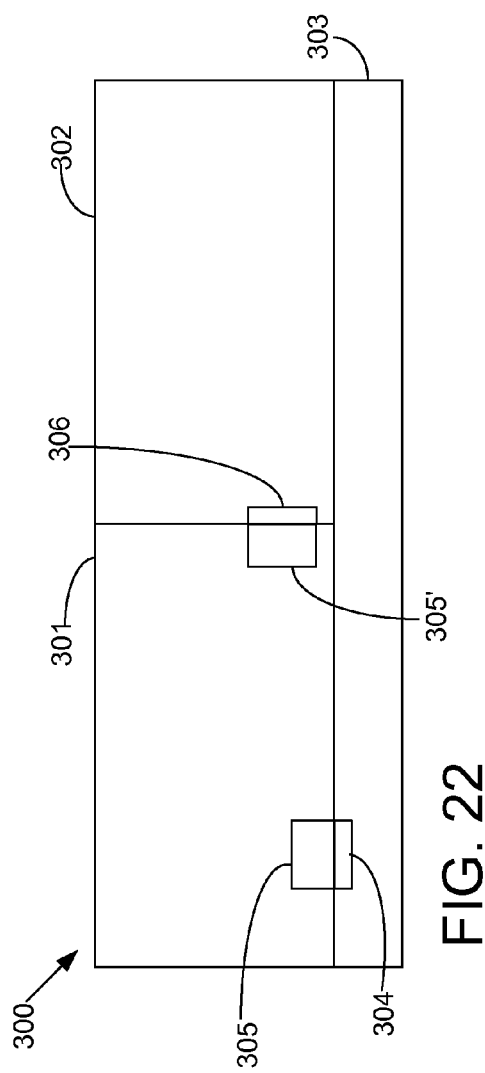
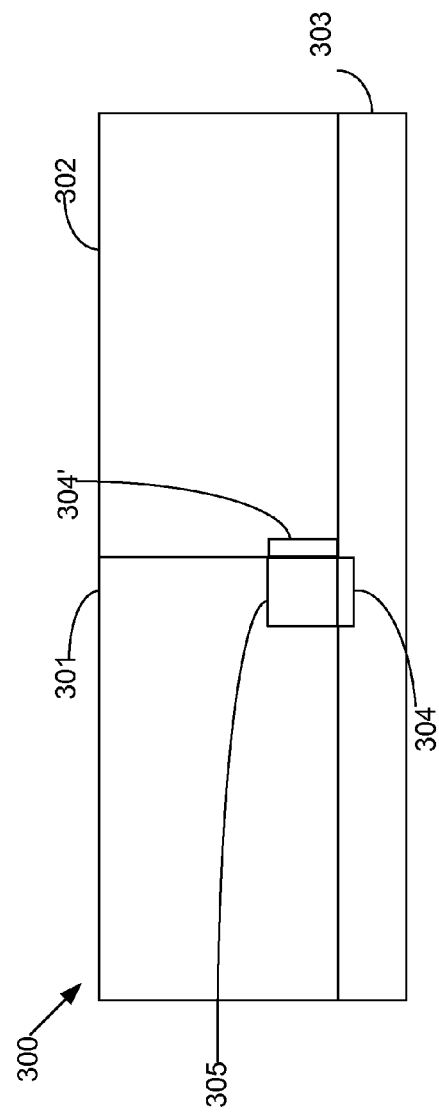

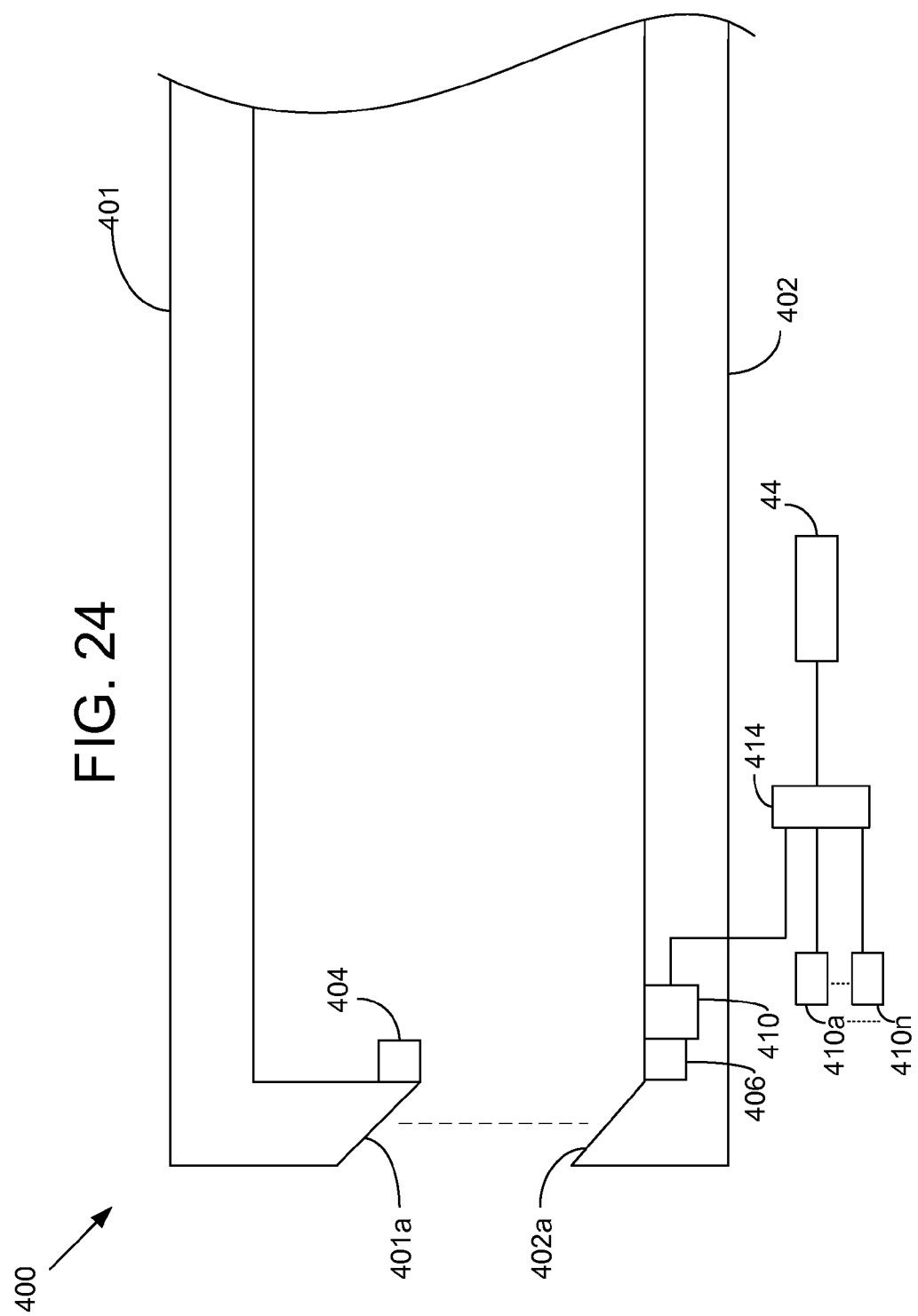

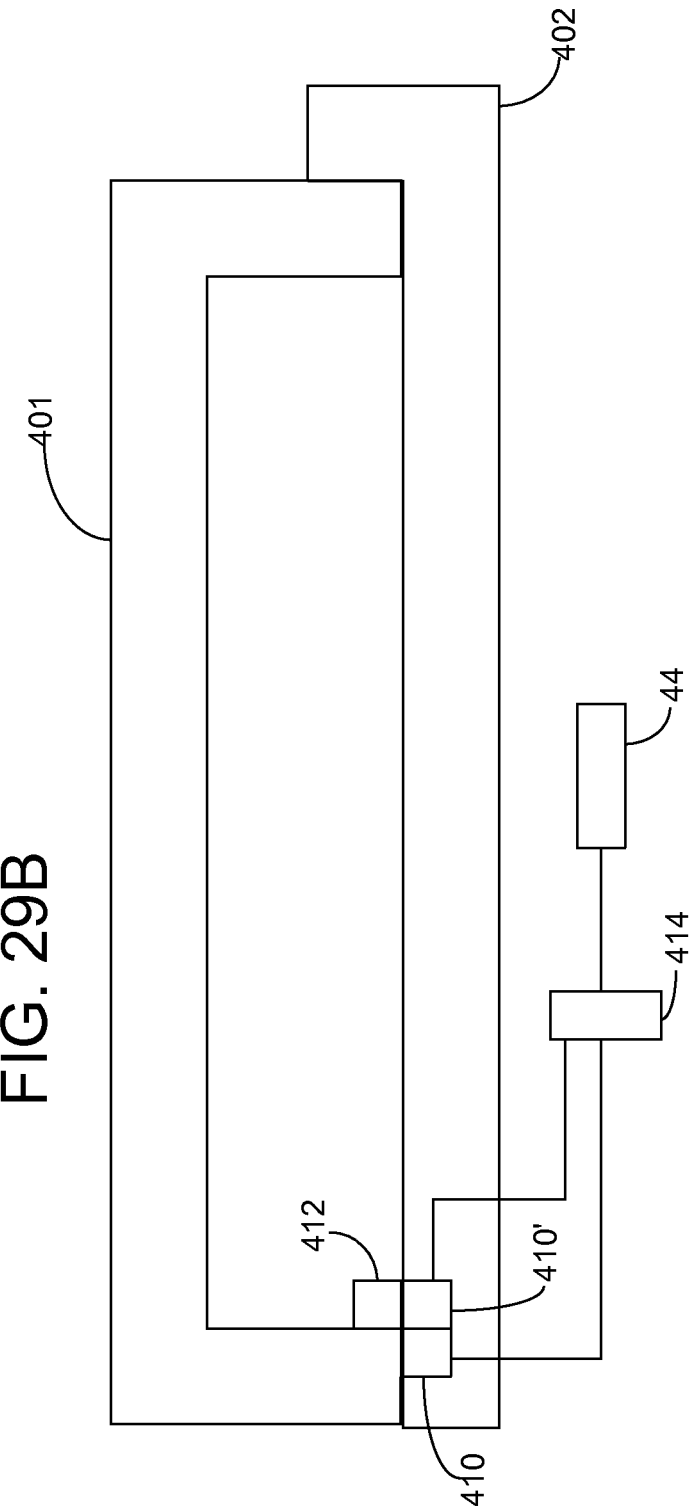

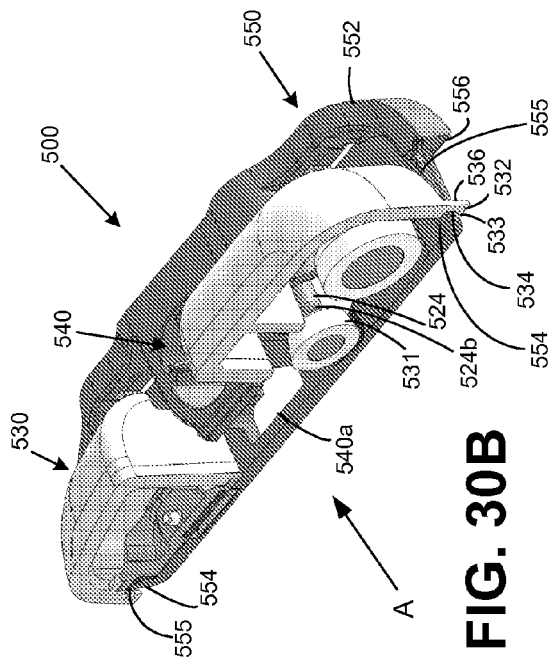
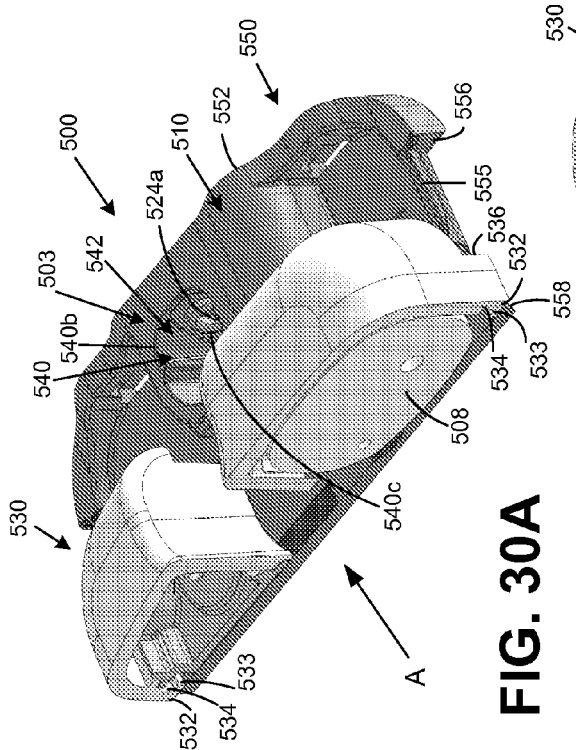
FIG. 30B
FIG. 30C
FIG. 30A

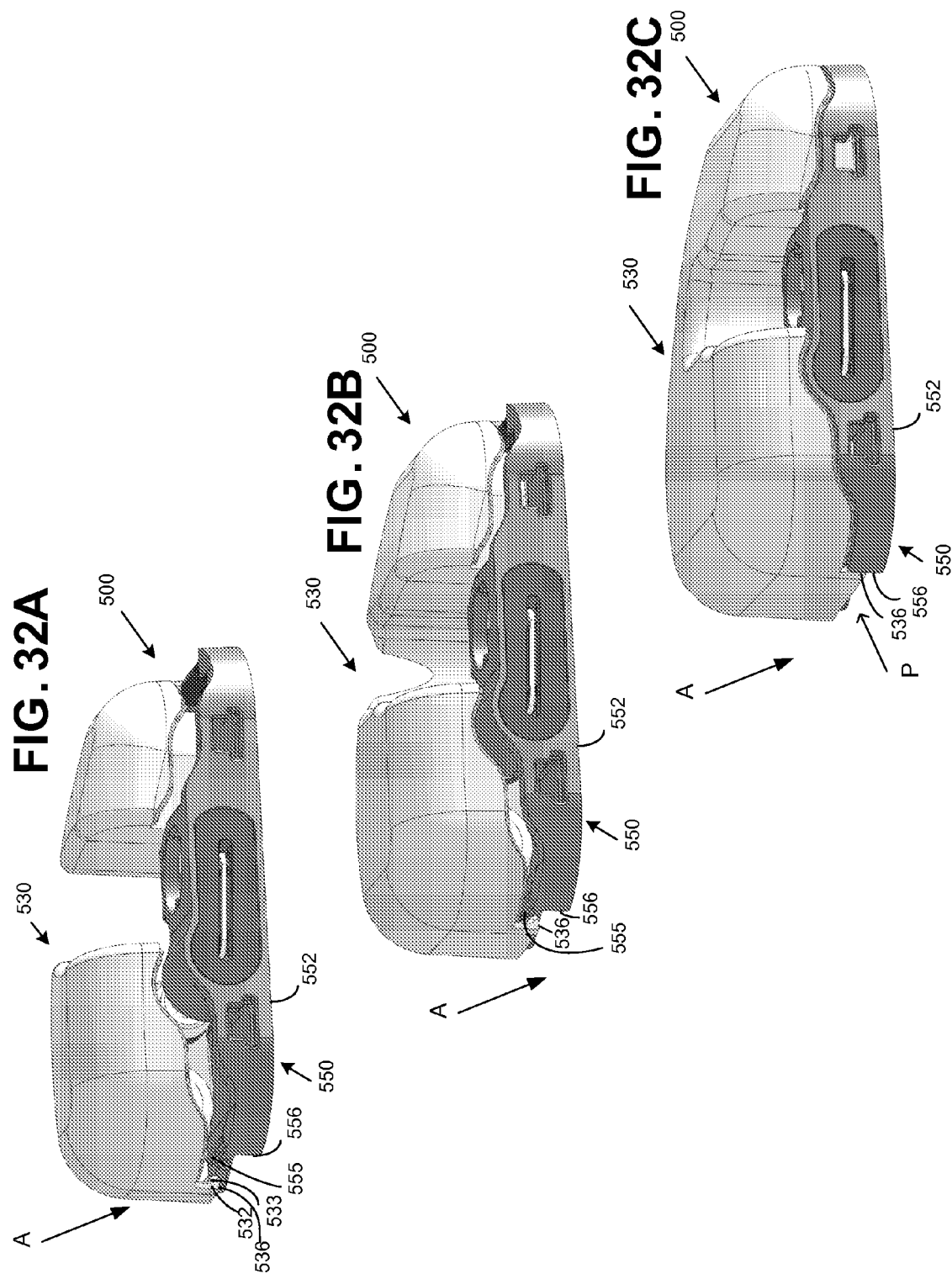

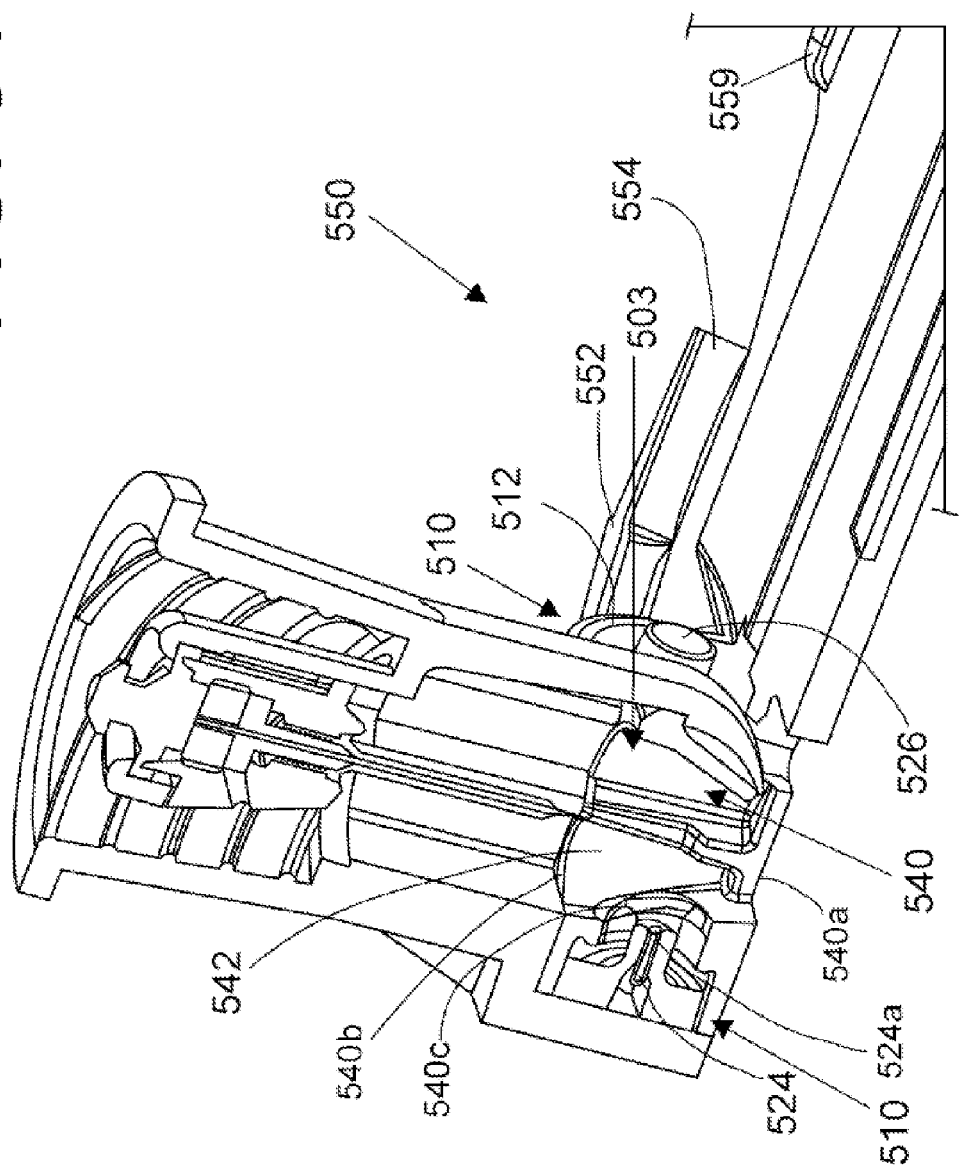

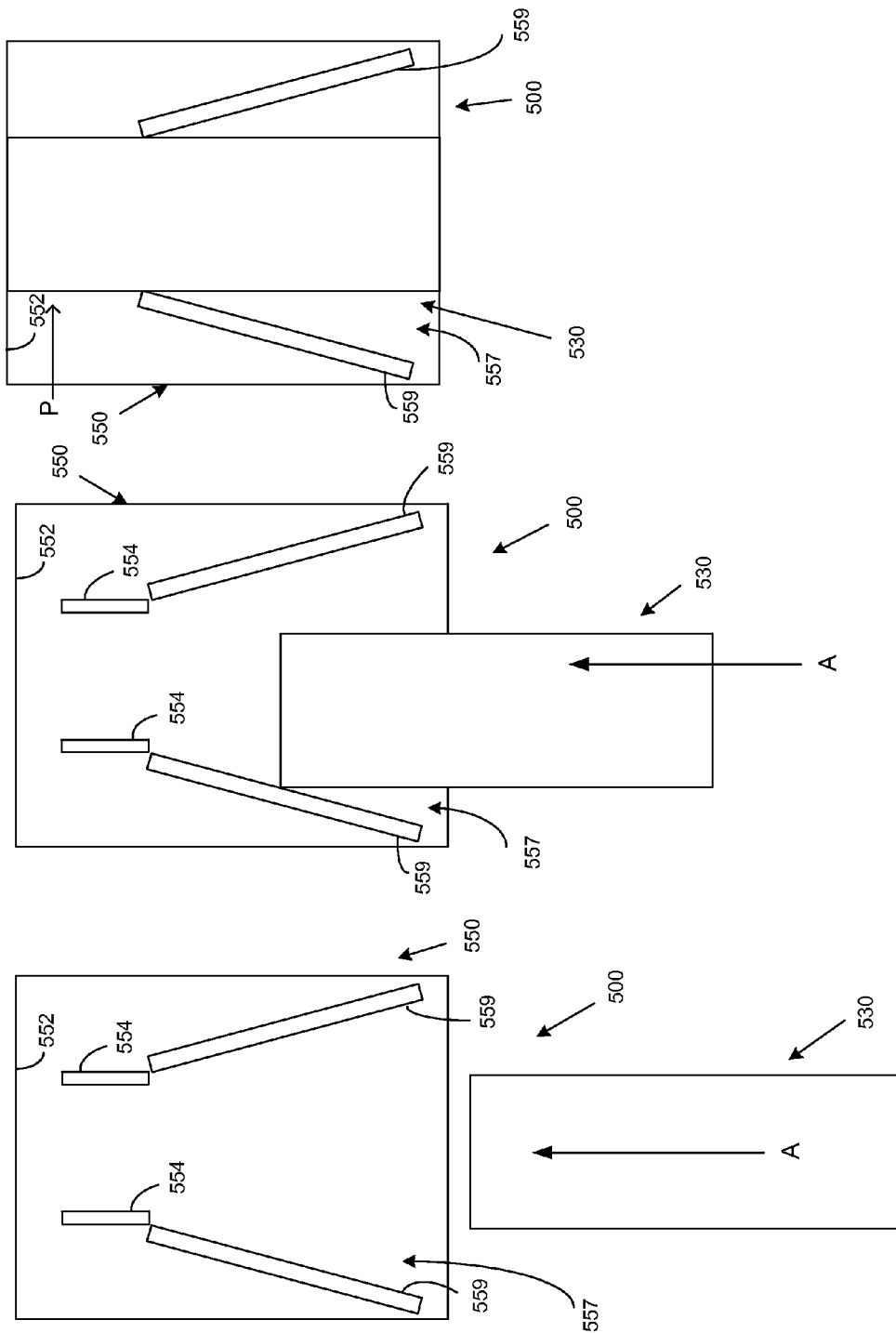

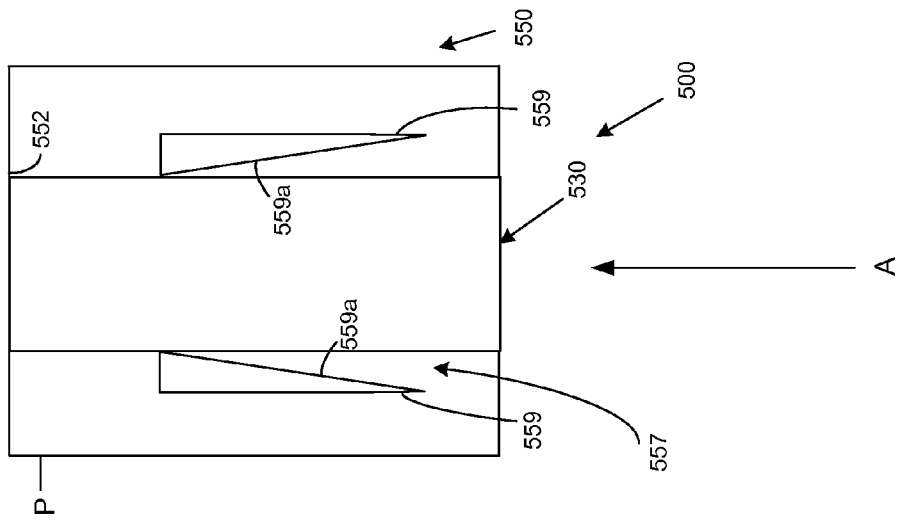
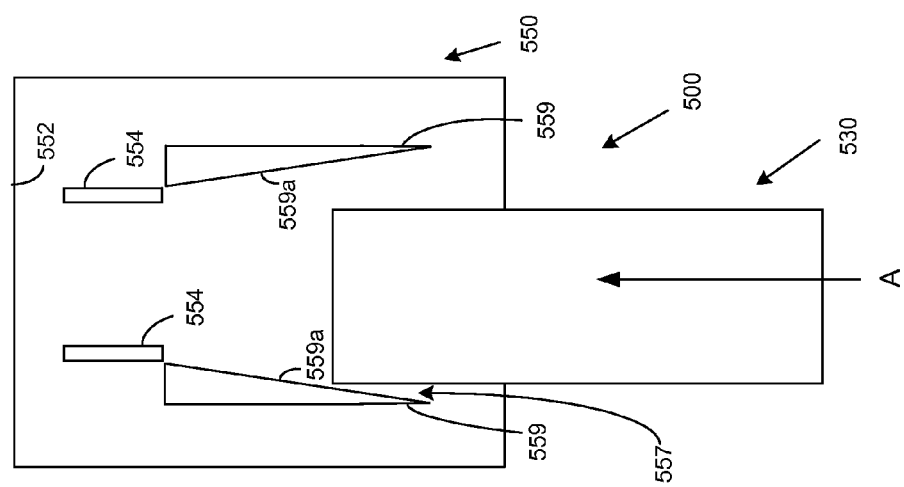
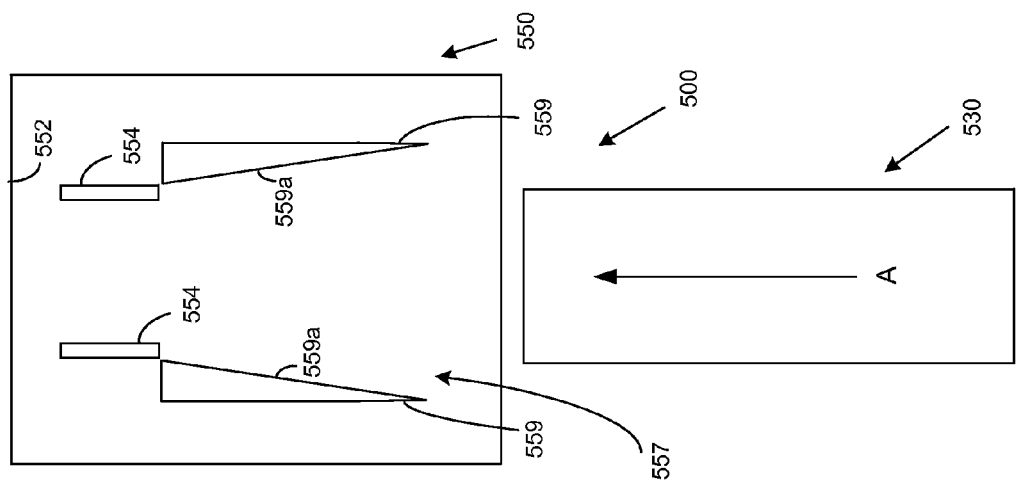

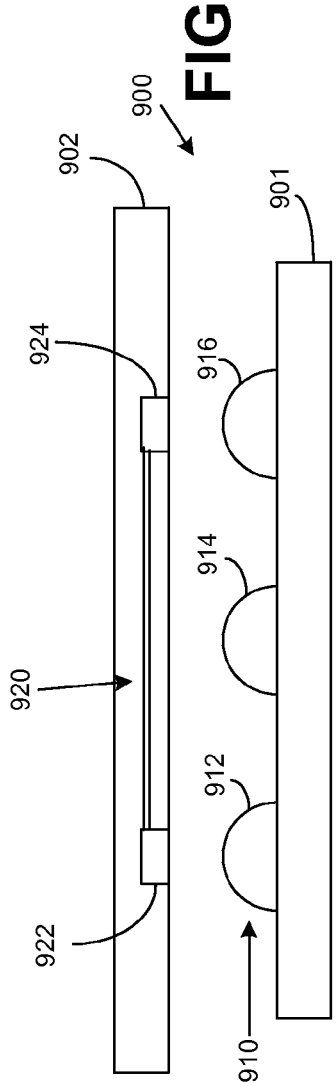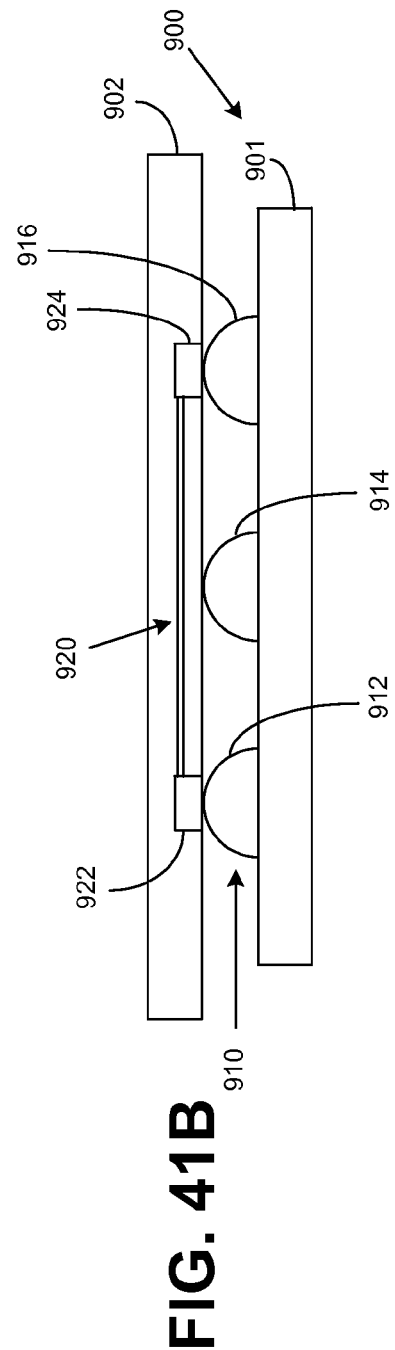

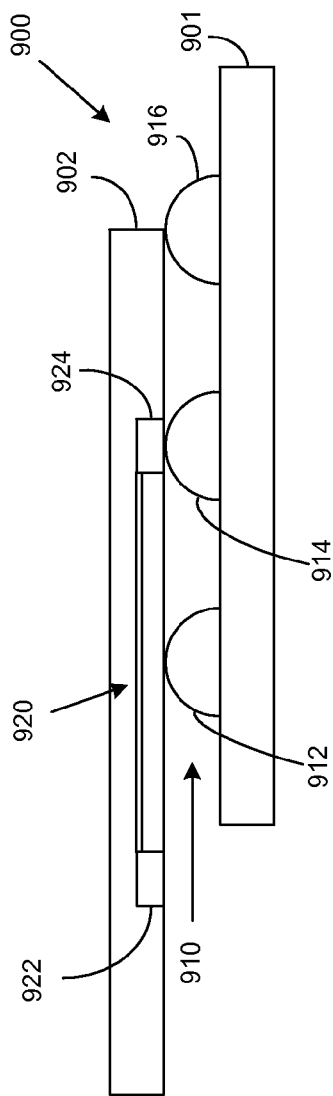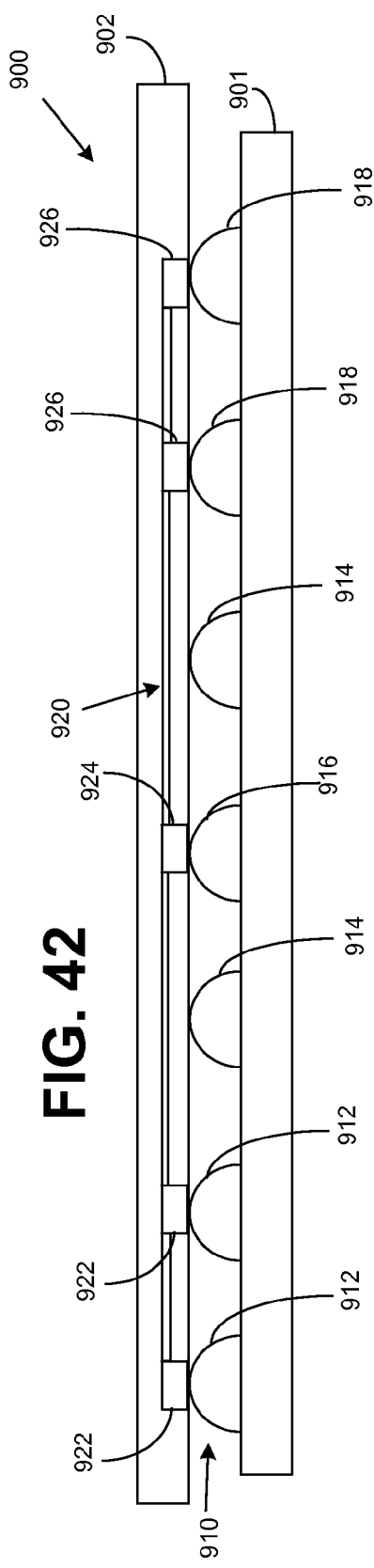

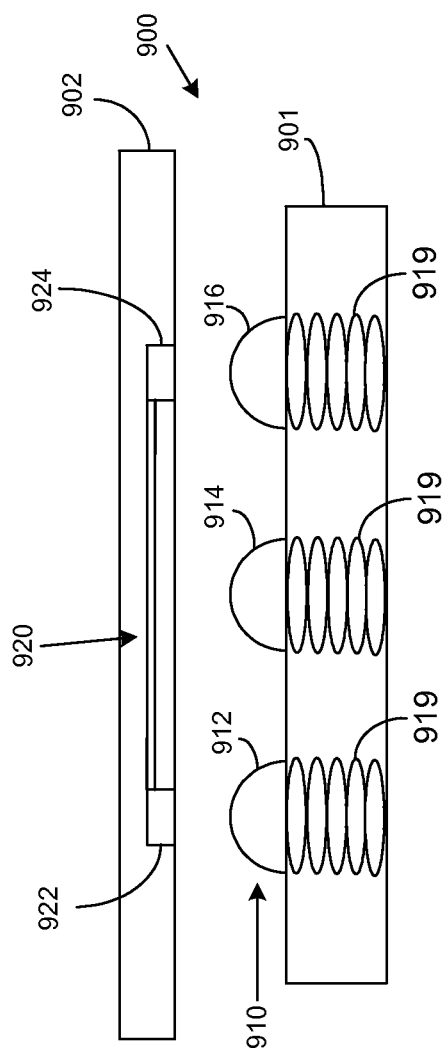
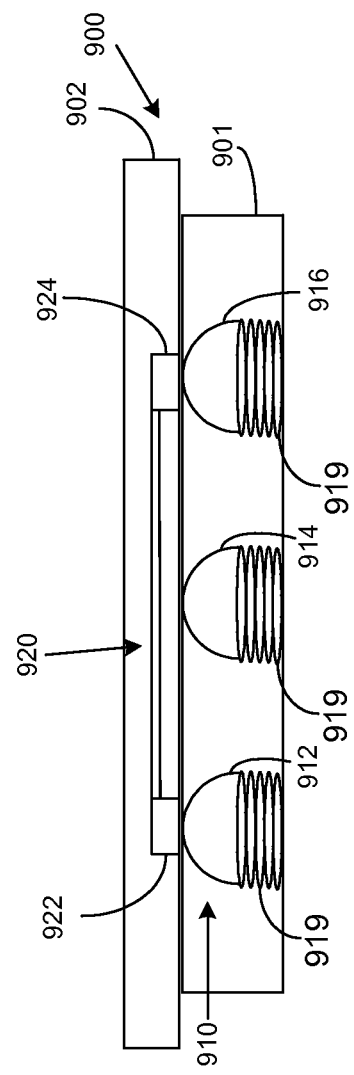

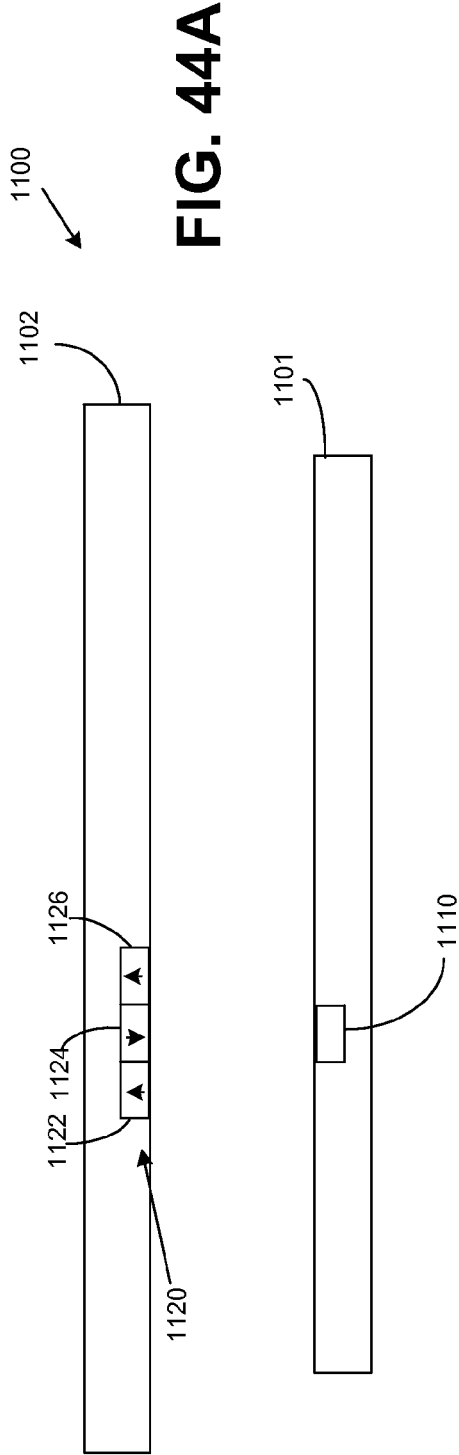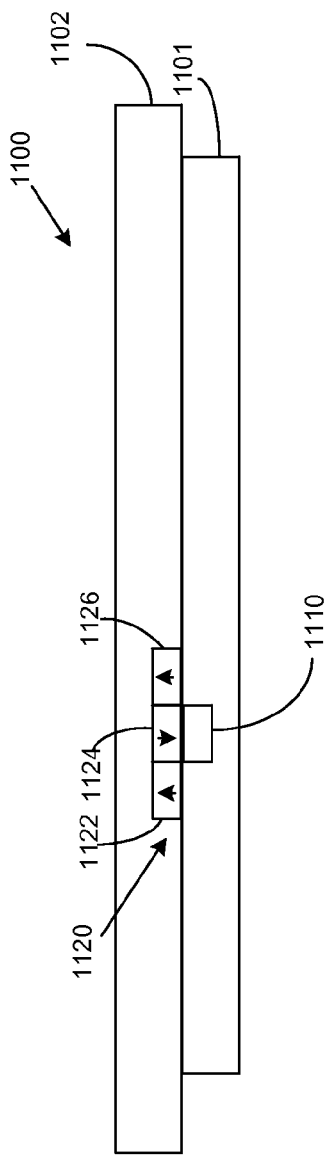

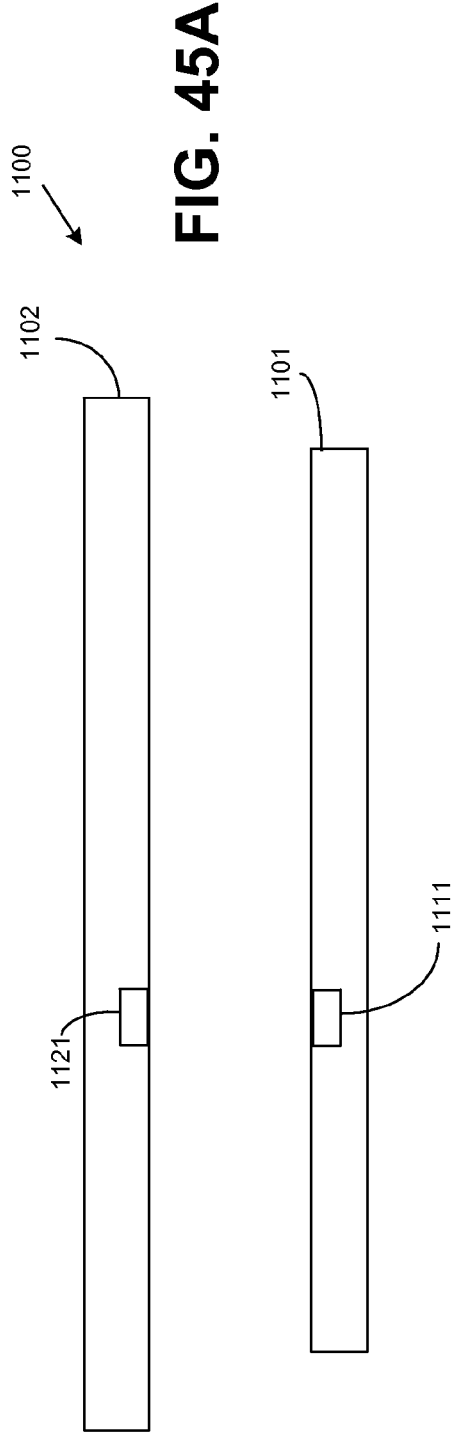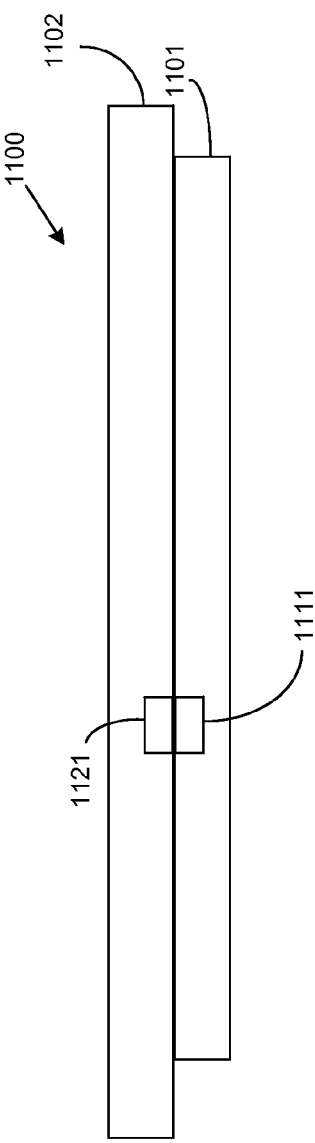

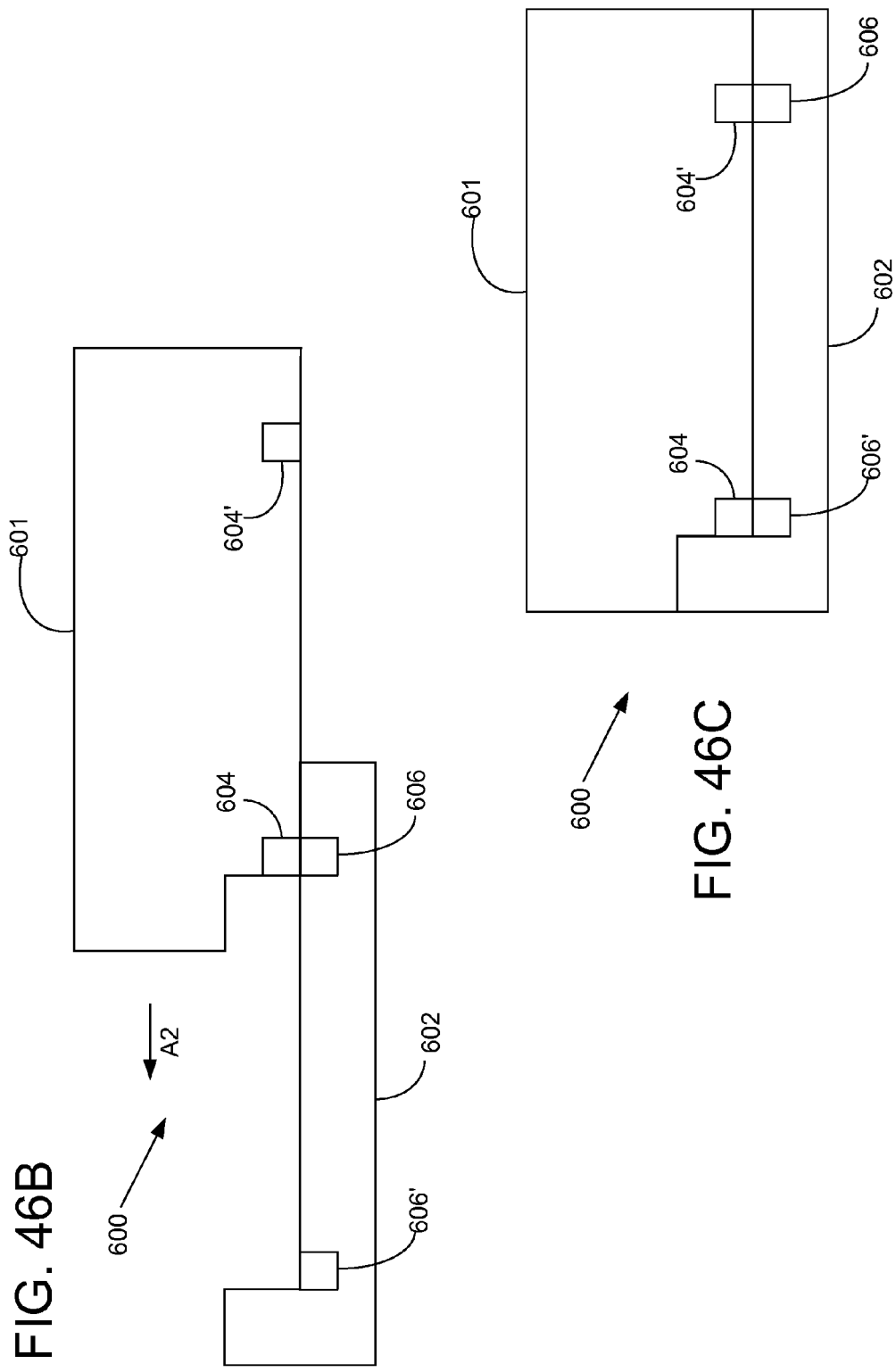

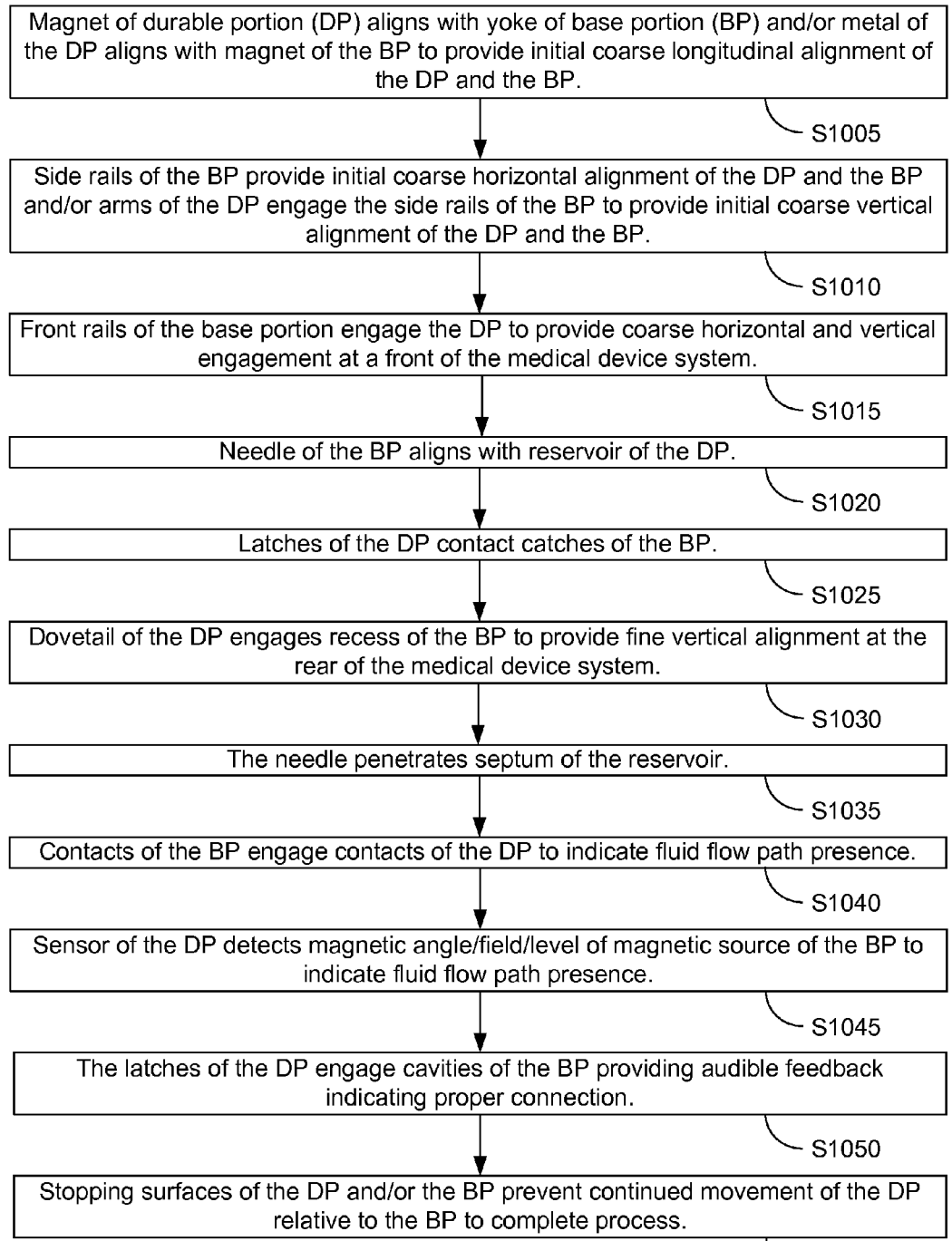

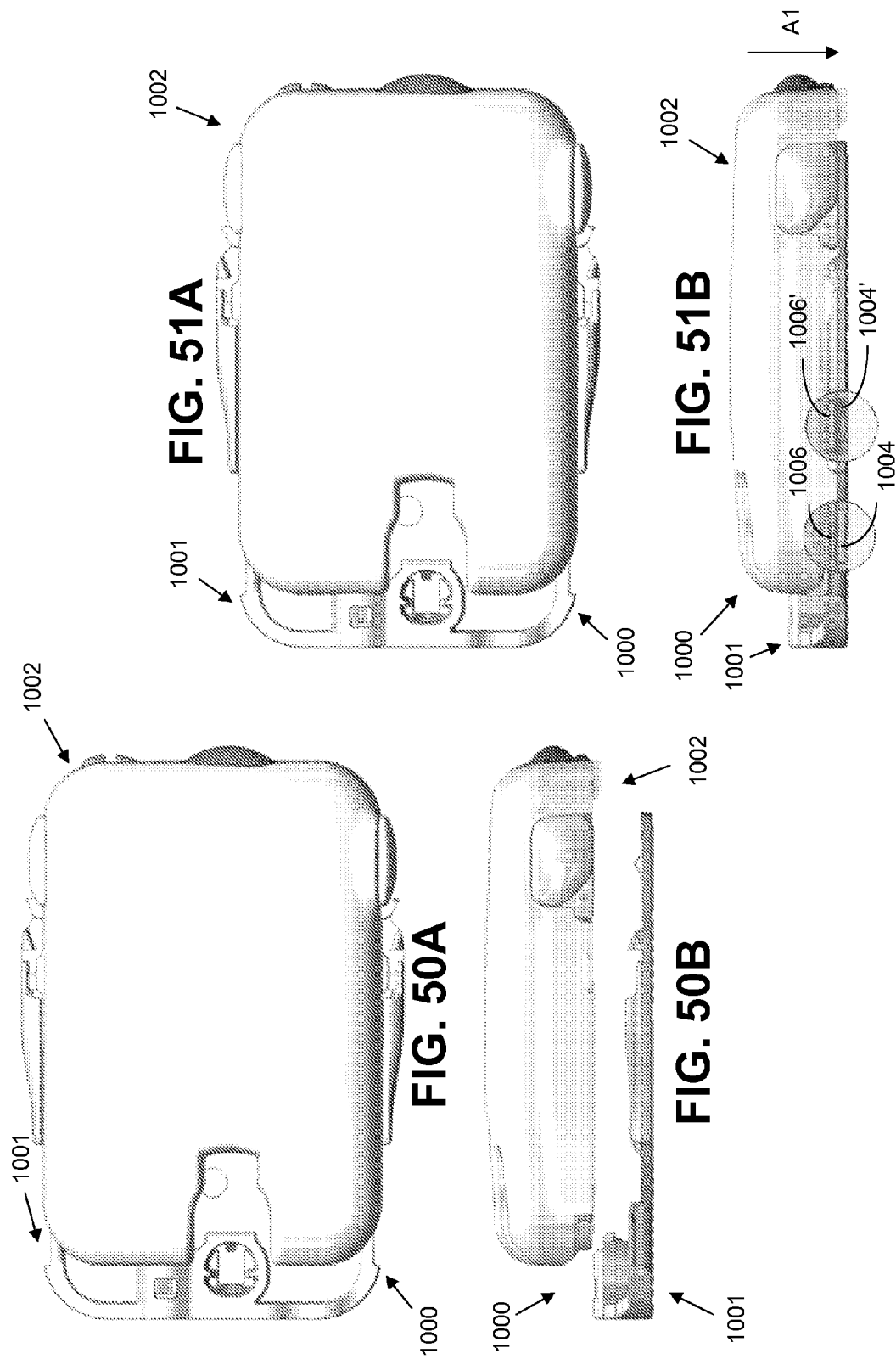

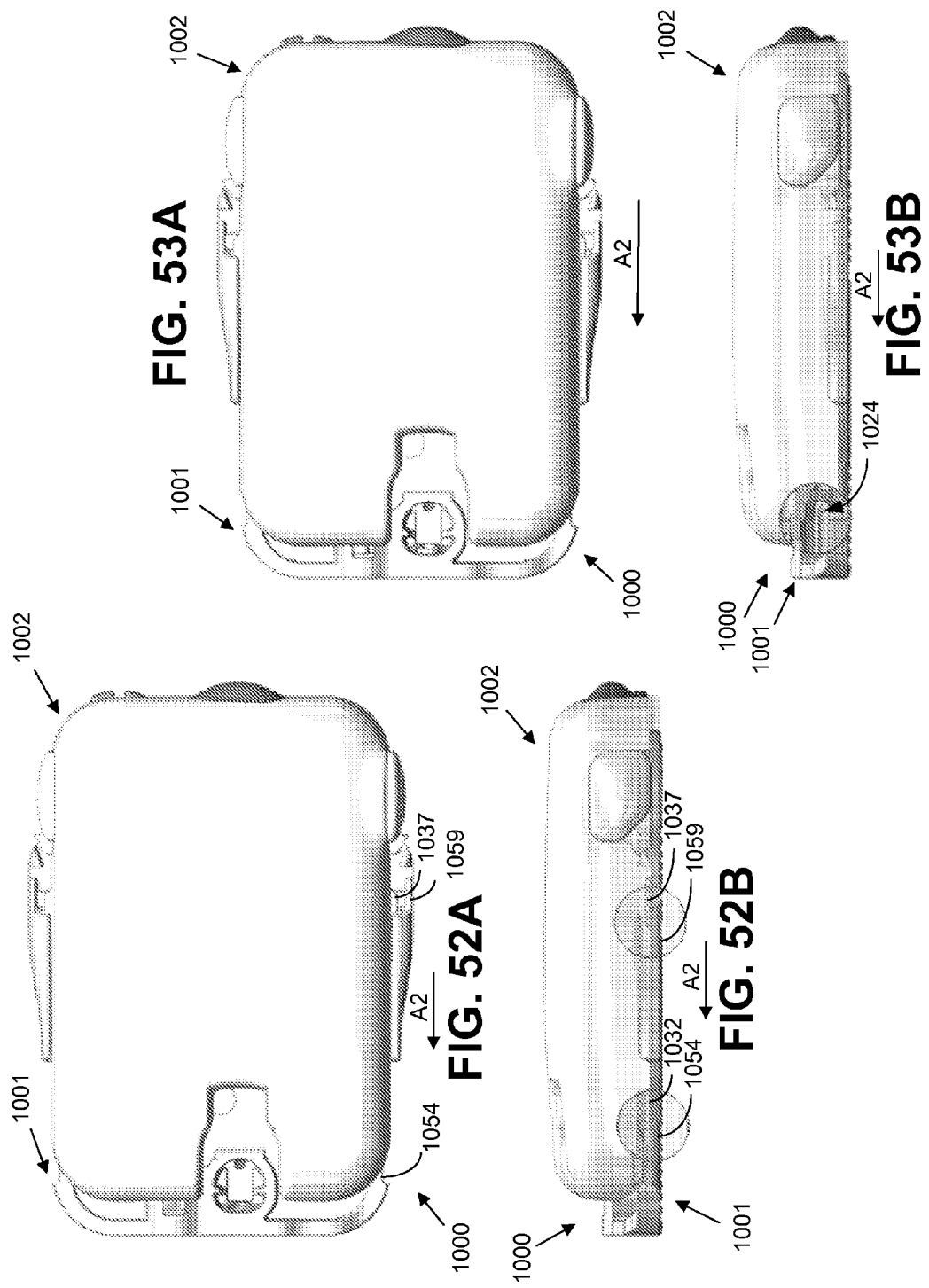

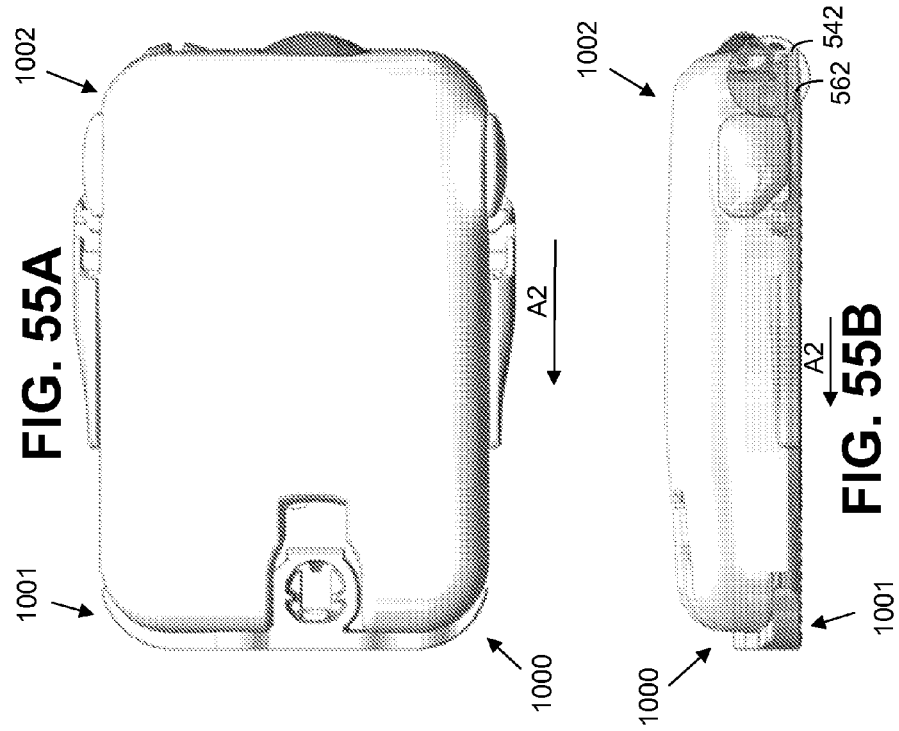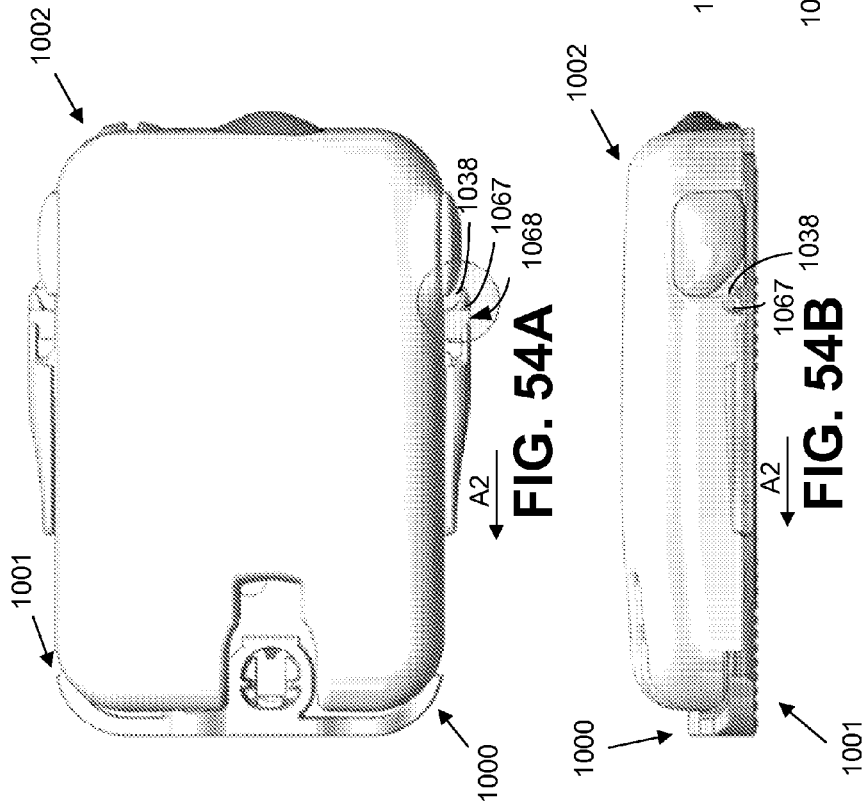

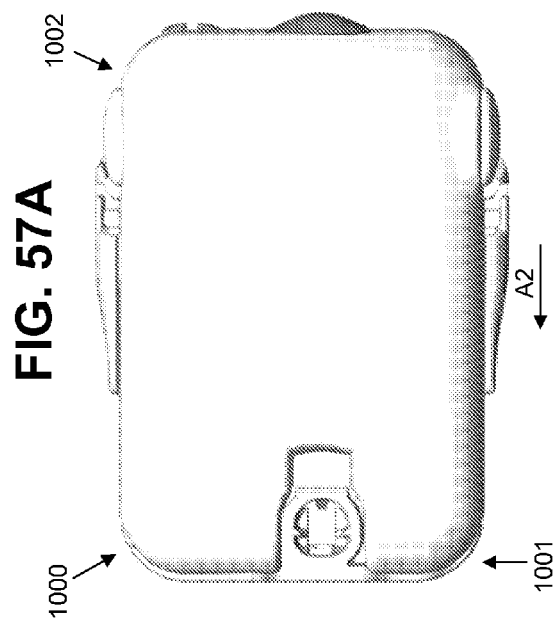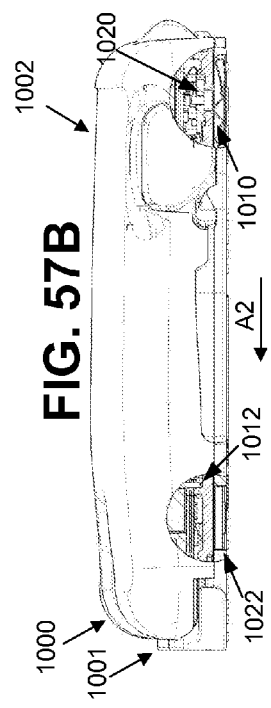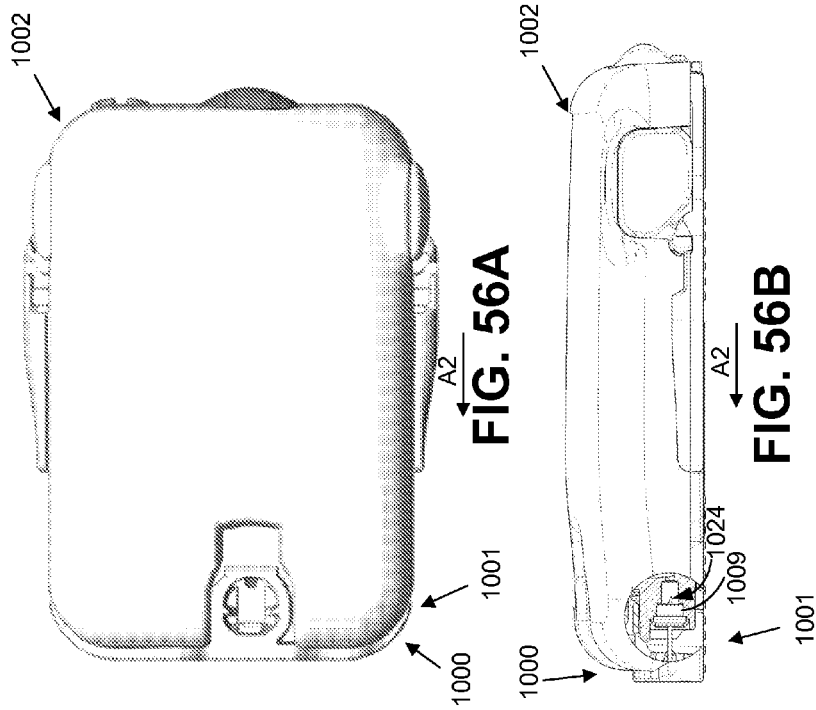

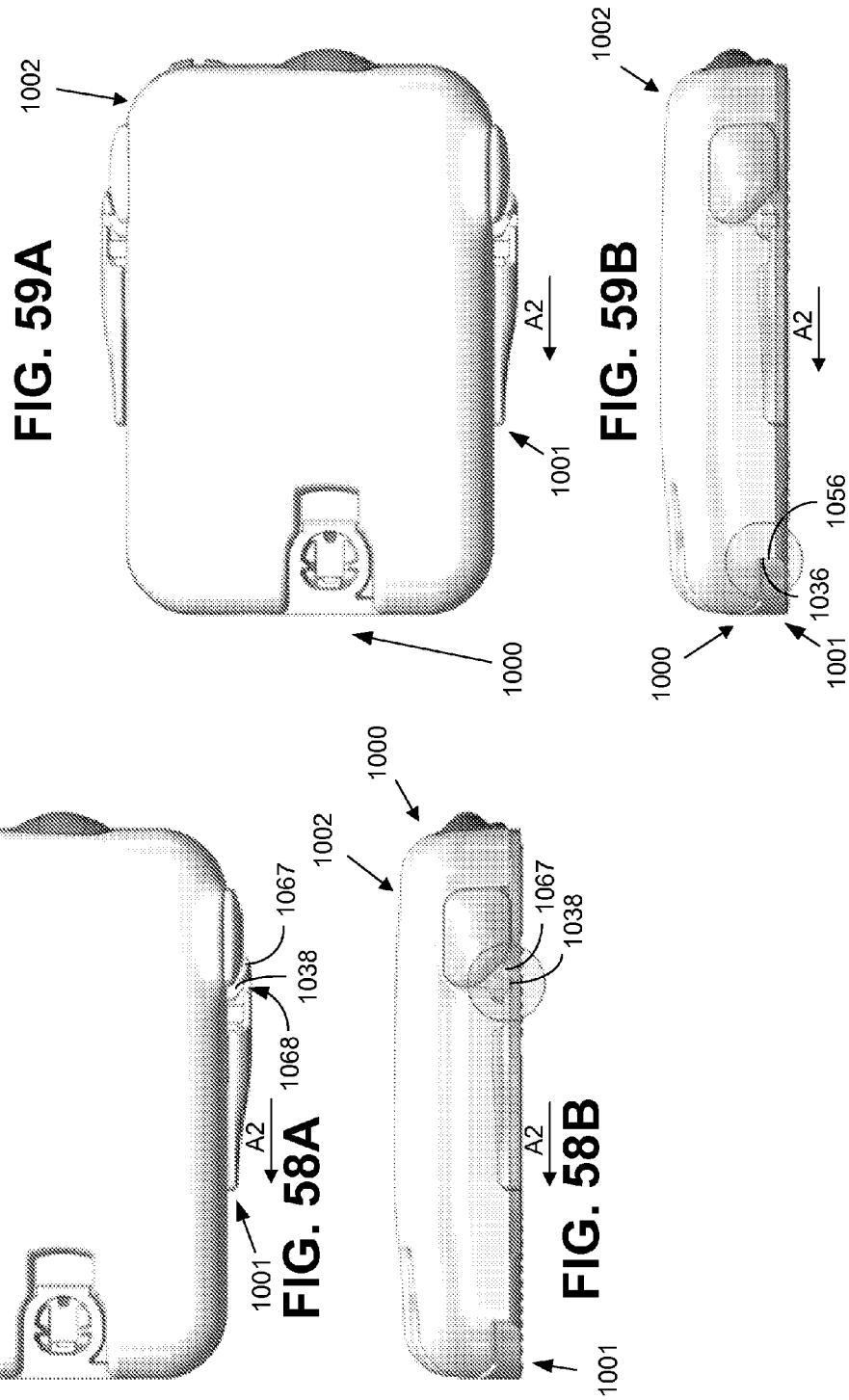

CONNECTION AND ALIGNMENT DETECTION SYSTEMS AND METHODS

CROSS-REFERENCE TO RELATED PATENT APPLICATIONS

This application is a Continuation of U.S. application Ser. No. 13/235,288, filed Sep. 16, 2011, now U.S. Pat. No. 8,435,209, which is a continuation-in-part of U.S. application Ser. No. 12/649,619, filed Dec. 30, 2009, now U.S. Pat. No. 8,308,679 and U.S. application Ser. No. 13/103,014, filed May 6, 2011, now U.S. Pat. No. 9,421,321, the entire contents of each of these applications are incorporated by reference herein.

BACKGROUND

1. Field of the Invention

Embodiments of the present invention generally relate to medical device systems and methods, and, in specific embodiments, such systems and methods that include connection and/or alignment features for connecting, aligning, and/or detecting thereof components of medical device systems.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. Further examples of various insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A medical device for treating a user includes, but is not limited to, a first housing portion, a second housing portion, a reservoir, at least one of a drive device and a needle-inserting device, a magnet, at least one of a first magnetically attractive material and a first magnet-responsive device, at least one of a second magnetically attractive material and a second magnet-responsive device, and electronic circuitry.

The first housing portion is adapted to be carried by a user. The second housing portion is configured to be selectively operatively engaged with and disengaged from the first housing portion. The first housing portion and the second housing portion are configured to be movable relative to each other from a first position to a second position to operatively engage each other at the second position. The reservoir is supported by one of the first and second housing portions. The at least one of a drive device and a needle-inserting device is supported by the other of the first housing portion and the second housing portion relative to the housing portion that supports the reservoir, such that upon the first housing portion and the second housing portion being operatively engaged at the second position, the reservoir is operatively coupled to the at least one of the drive device and the needle-inserting device. The magnet is supported on the first housing portion. The at least one of a first magnetically attractive material and a first magnet-responsive device is supported on the second housing portion in a position to magnetically interact with the magnet when the first housing portion and the second housing portion are in the first position. The at least one of a second magnetically attractive material and a second magnet-responsive device is supported on the second housing portion in a position to magnetically interact with the magnet, upon the first housing portion and the second housing portion being operatively engaged at the second position. The electronic circuitry is configured to detect at least one of a first magnetic interaction between the magnet and the at least one of a first magnetically attractive material and a first magnet-responsive device, and a second magnetic interaction between the magnet and the at least one of a second magnetically attractive material and a second magnet-responsive device. The circuitry configured to provide a signal or a change in state in response to detection of at least one of the first magnetic interaction and the second magnetic interaction.

In various embodiments, the at least one of a first magnetically attractive material and a magnet-responsive device comprises a magnetically attractive material that is attracted to the magnet when the first housing portion and the second housing portion are in the first position.

In further embodiments, the at least one of a second magnetically-attractive material and a magnet-responsive device comprises a magnet-responsive device that provides the signal or changes the state, upon the first housing portion and the second housing portion being operatively engaged at the second position.

In various embodiments, the at least one of a second magnetically attractive material and a magnet-responsive device comprises a magnet-responsive device that provides the signal or changes the state, upon the first housing portion and the second housing portion being operatively engaged at the second position.

In some embodiments, the device further includes a user-perceptible indicator operatively coupled to the magnet-responsive device for providing a user-perceptible indication in response to the signal or change in the state of the magnet-responsive device upon the first housing portion and the second housing portion being operatively engaged at the second position.

In further embodiments, the user-perceptible indication comprises at least one of an audible indication, a visual indication, and a tactile indication.

In some embodiments, the at least one of a drive device and a needle-inserting device comprises a drive device for selectively driving fluid from the reservoir. The delivery device further includes control electronics operatively coupled to the magnet-responsive device for controlling the drive device dependent upon the signal from or state of the magnet-responsive device.

In further embodiments, the control electronics is configured to inhibit operation of the drive device unless the signal from or state of the magnet-responsive device corresponds to the signal or state when the first housing portion and the second housing portion are operatively engaged at the second position.

In some embodiments, the magnet has at least one of a certain magnetic field and a certain magnetic strength. The magnetic-responsive device comprises a sensor for detecting at least one of the certain magnetic field and the certain magnetic strength. The device further including electronic circuitry configured to provide a first signal in a case where the first housing portion and the second housing portion are operatively engaged at the second position and the sensor detects at least one of the certain magnetic field and the certain magnetic strength of the magnet. The electronic circuitry is further configured to provide a second signal in a case where the first housing portion and the second housing portion are operatively engaged at the second position and the sensor detects at least one of a magnetic field different from the certain magnetic field and a magnetic strength different from the certain magnetic strength of the magnet.

In further embodiments, the sensor is configured to provide a signal for activating control circuitry of the drive device in a case where the sensor detects a gauss level exceeding a pre-defined threshold value.

In various embodiments, the reservoir supports one of the magnet and the at least one of a second magnetically attractive material and a second magnet-responsive device. The at least one of a drive device and a needle-inserting device supports the other of the one of the magnet and the at least one of a second magnetically attractive material and a second magnet-responsive device in a position to interact with each other when the reservoir is operatively coupled to the at least one of the drive device and the needle-inserting device upon the first housing portion and the second housing portion being operatively engaged at the second position.

In various embodiments, the magnet and the at least one of a first magnetically attractive material and a first magnet-responsive device are configured to be magnetically interactable with each other in a case where the first housing portion and the second housing portion are operatively engaged and positioned relative to each other in a predetermined manner.

In some embodiments, the first housing portion and the second housing portion are positioned relative to each other in a predetermined manner in a case where the first housing portion and the second housing portion are aligned in more than one dimension.

In some embodiments, the first housing portion and the second housing portion are positioned relative to each other in a predetermined manner in a case where the magnet and the at least one of a first magnetically attractive material and a first magnet-responsive device are sufficiently proximate to each other.

In various embodiments, the magnet and the at least one of a first magnetically-attractive material and a first magnet-responsive device are configured to be interactable with each other in a case where the first housing portion and the second housing portion are operatively engaged and the magnet and the at least one of a first magnetically-attractive material and a first magnet-responsive device are sufficiently proximate to each other.

In some embodiments, the magnet and the at least one of a first magnetically attractive material and a first magnet-responsive device are sufficiently proximate to each other in a case where the magnet and the at least one of a first magnetically attractive material and a first magnet-responsive device contact each other.

In some embodiments, the magnet and the at least one of a first magnetically attractive material and a first magnet-responsive device are sufficiently proximate to each other in a case where the magnet and the at least one of a first magnetically attractive material and a first magnet-responsive device are adjacent each other.

In some embodiments, the magnet and the at least one of a first magnetically attractive material and a first magnet-responsive device are sufficiently proximate to each other in a case where the magnet and the at least one of a first magnetically attractive material and a first magnet-responsive device are within a predetermined distance of each other.

A method of manufacturing a medical device for treating a user includes, but is not limited to, any one or combination of (i) adapting a first housing portion to be carried by a user; (ii) configuring a second housing portion to be selectively operatively engaged with and disengaged from the first housing portion, the first housing portion and the second housing portion configured to be movable relative to each other from a first position to a second position to operatively engage each other at the second position; (iii) supporting a reservoir by one of the first and second housing portions; (iv) supporting at least one of a drive device and a needle-inserting device by the other of the first housing portion and the second housing portion relative to the housing portion that supports the reservoir, such that upon the first housing portion and the second housing portion being operatively engaged at the second position, the reservoir is operatively coupled to the at least one of the drive device and the needle-inserting device; (v) supporting a magnet on the first housing portion; (vi) supporting at least one of a first magnetically attractive material and a first magnet-responsive device on the second housing portion in a position to magnetically interact with the magnet when the first housing portion and the second housing portion are in the first position; (vii) supporting at least one of a second magnetically attractive material and a second magnet-responsive device on the second housing portion in a position to magnetically interact with the magnet, upon the first housing portion and the second housing portion being operatively engaged at the second position; (viii) configuring electronic circuitry to detect at least one of a first magnetic interaction between the magnet and the at least one of a first magnetically attractive material and a first magnet-responsive device, and a second magnetic interaction between the magnet and the at least one of a second magnetically attractive material and a second magnet-responsive device; and (ix) configuring the circuitry to provide a signal or a change in state in response to detection of at least one of the first magnetic interaction and the second magnetic interaction.

BRIEF DESCRIPTION OF THE DRAWINGS

FIG. 7 illustrates a portion of a medical device system in accordance with an embodiment of the present invention;

FIG. 9 illustrates a medical device system in accordance with an embodiment of the present invention;

FIG. 10A illustrates a medical device system in accordance with an embodiment of the present invention;

FIG. 14A illustrates a portion of a medical device system in accordance with an embodiment of the present invention;

FIG. 14B illustrates a portion of a medical device system in accordance with an embodiment of the present invention;

FIG. 15A illustrates a portion of a medical device system in accordance with an embodiment of the present invention FIG. 15B illustrates a portion of a medical device system in accordance with an embodiment of the present invention FIG. 16 illustrates a portion of a medical device system in accordance with an embodiment of the present invention;

FIG. 20 illustrates a medical device system in accordance with an embodiment of the present invention;

FIG. 21 illustrates a medical device system in accordance with an embodiment of the present invention;

FIG. 22 illustrates a medical device system in accordance with an embodiment of the present invention;

FIG. 23 illustrates a medical device system in accordance with an embodiment of the present invention;

FIG. 24 illustrates a portion of a medical device system in accordance with an embodiment of the present invention;

FIG. 29B illustrates a medical device system in accordance with an embodiment of the present invention;

FIGS. 30A-30C illustrate a cutaway view of a portion of medical device system in accordance with an embodiment of the present invention;

FIGS. 32A-32C illustrate a portion of medical device system in accordance with an embodiment of the present invention;

FIG. 34 illustrates a portion of a medical device system in accordance with an embodiment of the present invention;

FIGS. 37A-37C illustrate a medical device system in accordance with an embodiment of the present invention;

FIGS. 38A-38C illustrate a medical device system in accordance with an embodiment of the present invention;

FIGS. 41A-41C illustrate a portion of a medical device system in accordance with an embodiment of the present invention;

FIG. 42 illustrates a portion of a medical device system in accordance with an embodiment of the present invention;

FIGS. 43A and 43B illustrate a portion of a medical device system in accordance with an embodiment of the present invention;

FIGS. 44A and 44B illustrate a portion of a medical device system in accordance with an embodiment of the present invention;

FIGS. 45A and 45B illustrate a portion of a medical device system in accordance with an embodiment of the present invention;

FIGS. 46A, 46B, and 46C illustrate a medical device system in accordance with an embodiment of the present invention;

FIG. 49 is a flowchart illustrating a process for aligning and/or connecting components of a medical device system in accordance with an embodiment of the present invention; and FIGS. 50A-59B illustrate an engagement sequence of a medical device system in accordance with an embodiment of the present invention.

DETAILED DESCRIPTION

Figure 1:
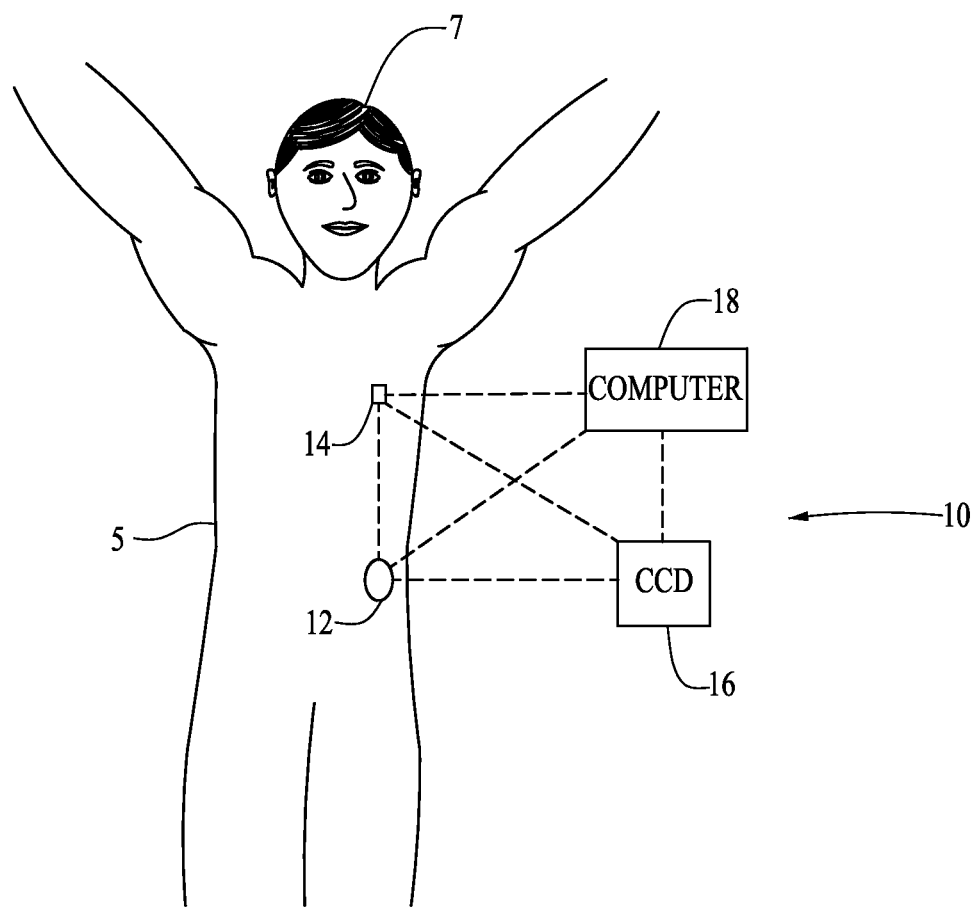
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. patent applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No.

11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. Patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; (liii) U.S. patent application Ser. No. 12/360,813, filed Jan. 27, 2009, "Multi-Position Infusion Set Device And Process"; (liv) U.S. Patent Pub. No. US 2007/0142776 (application Ser. No. 10/314,653), filed Dec. 9, 2002, "Insertion Device For An Insertion Set and Methods Of Using The Same." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
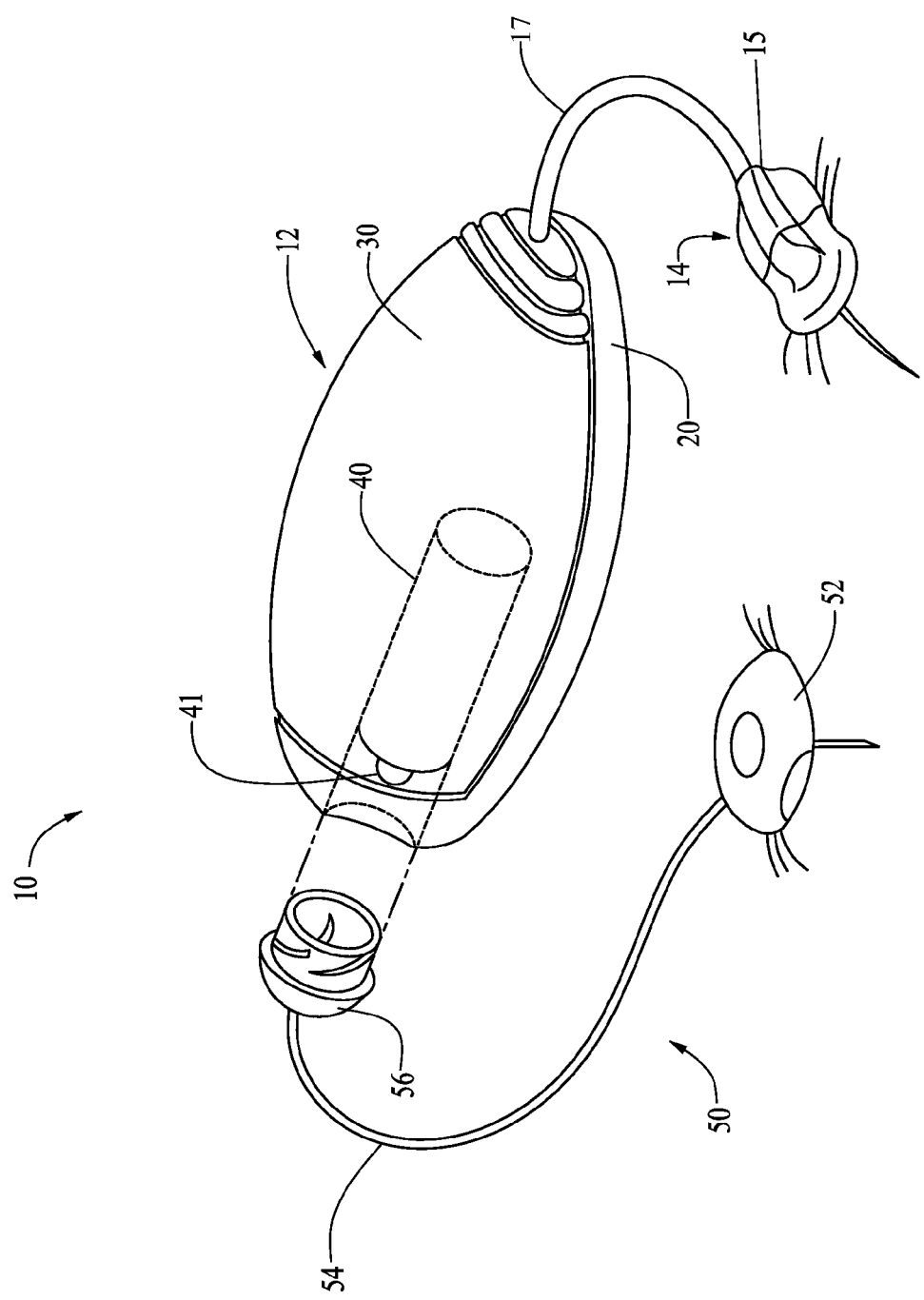
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same," which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (un-used) disposable housing 20 for further delivery operation with a user-patient.

Figure 3:
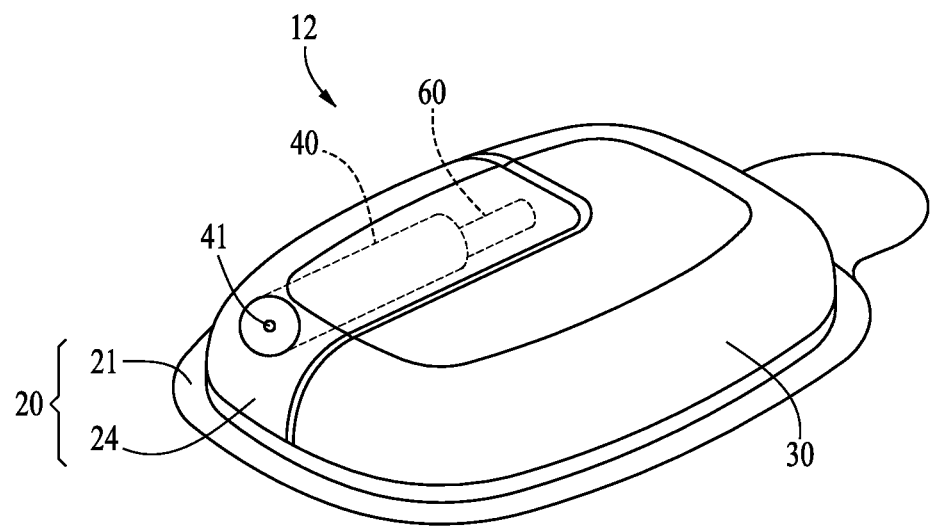
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
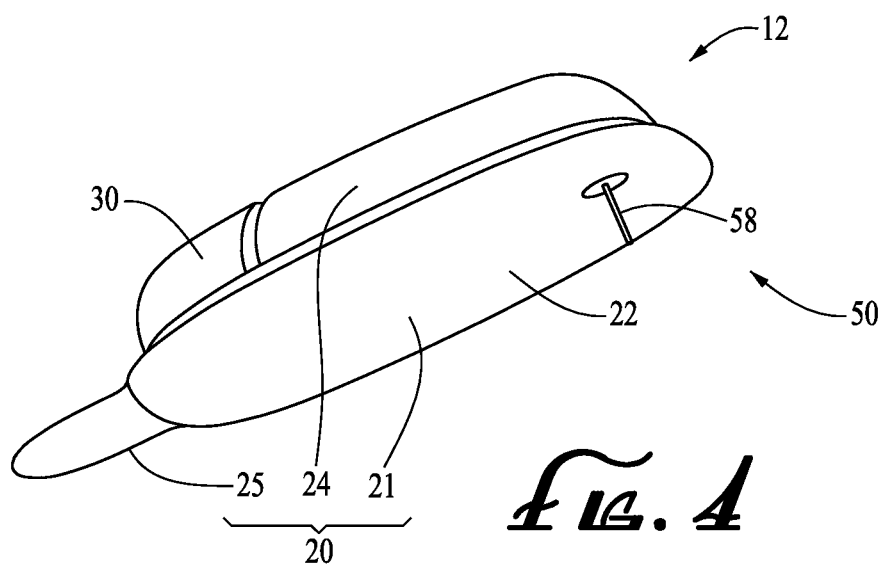
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
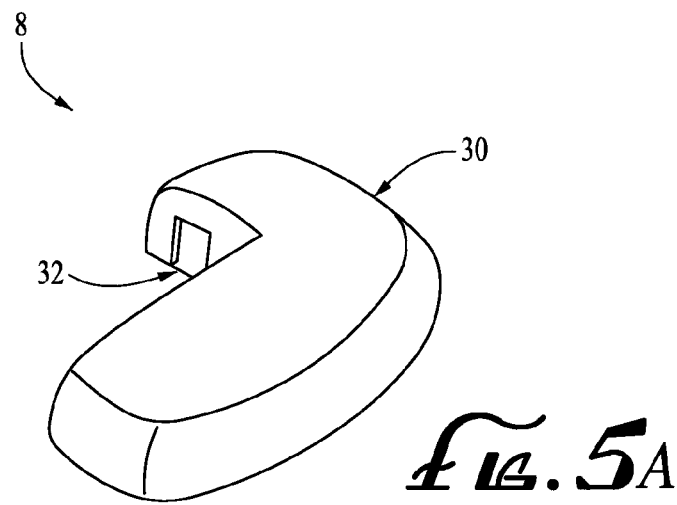
FIG. 5A illustrates a durable portion of a delivery device in accordance with an embodiment of the present invention.
Figure 5B:
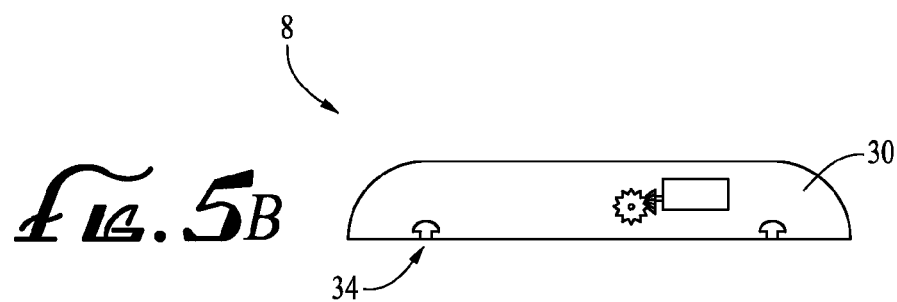
FIG. 5B illustrates a section view of a durable portion of a delivery device in accordance with an embodiment of the present invention.
Figure 5C:
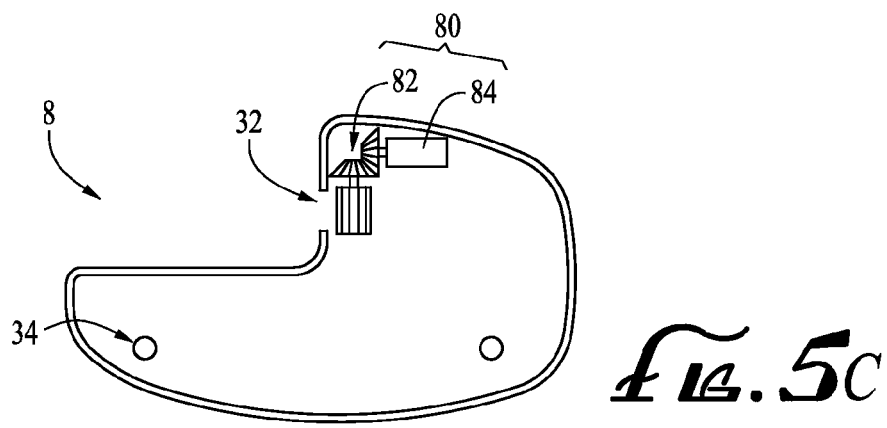
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
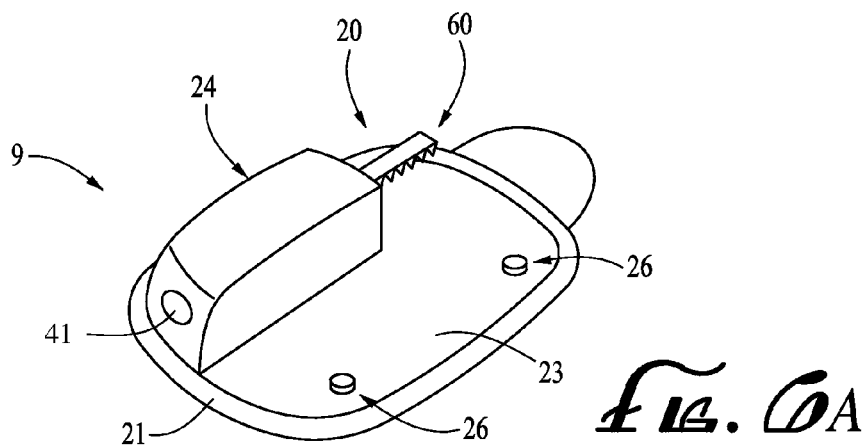
FIG. 6A illustrates a disposable portion of a delivery device in accordance with an embodiment of the present invention.
Figure 6B:
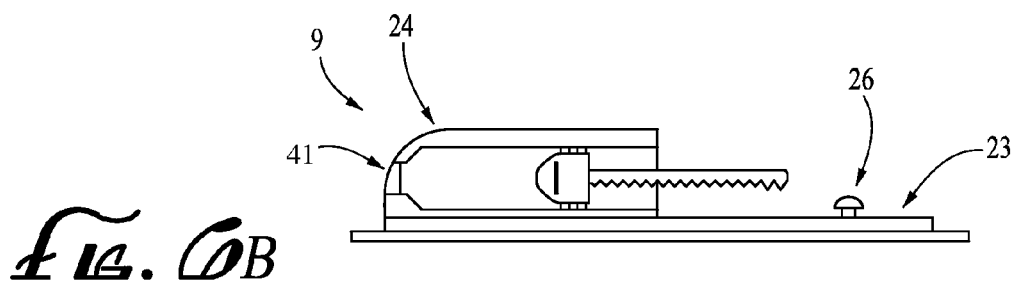
FIG. 6B illustrates a section view of a disposable portion of a delivery device in accordance with an embodiment of the present invention.
Figure 6C:
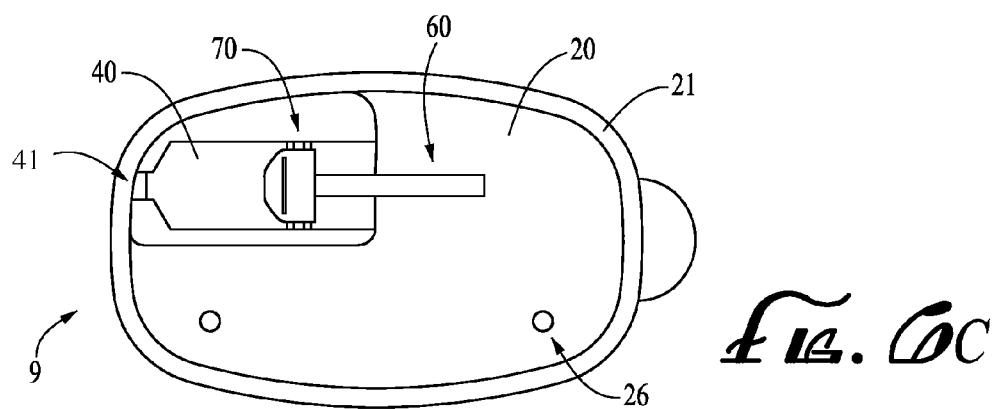
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 may include the reservoir status circuitry (not shown), and the reservoir status circuitry may be configured to read data from the reservoir circuitry (not shown) when the reservoir system 40 is inserted into the disposable portion 9.

In various embodiments, the reservoir status circuitry (not shown) may be further configured to store data to the reservoir circuitry after at least some of the contents of the reservoir system 40 have been transferred out of the reservoir system 40 to update information in the reservoir circuitry (not shown) related to an amount of contents still remaining in the reservoir system 40. In some embodiments, the reservoir status circuitry (not shown) may be configured to store data to the reservoir circuitry (not shown) to update information in the reservoir circuitry (not shown) related to an amount of contents remaining in the reservoir system 40 when the reservoir system 40 is inserted into the disposable portion 9. In some embodiments, the delivery device 12 may include the reservoir status circuitry (not shown) and the reservoir system 40 may include the reservoir circuitry (not shown), and the reservoir status circuitry (not shown) may selectively inhibit use of the delivery device 12 or may selectively provide a warning signal based on information read by the reservoir status circuitry (not shown) from the reservoir circuitry (not shown).

In addition, embodiments may be configured to establish a contiguous fluid flow passage for fluid transfer between a reservoir and the user-patient when the hollow needle or cannula is inserted into the user-patient. Needle-inserting devices according to embodiments of the present invention may be used with, connectable to and disconnectable from, or incorporated in a portion of an infusion medium delivery system. For example, a needle-inserting device may be connectable to a base structure of a pump-type delivery device for insertion of a needle, after which the needle-inserting device may be removed from the base structure, whereupon a further housing portion of the delivery device (containing components such as, but not limited to, a reservoir and pump or drive device) may be coupled to the base structure for operation.

Alternatively, the needle-inserting device may be incorporated into the further housing portion that contains other components as described above. In yet other embodiments, the needle-inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

In various embodiments, any of the connection structures described above for allowing one or more parts of the delivery device to be selectively connectable to and separable from one or more other parts of the delivery device may include one or more elements as will be described. The element(s) may function to provide one or more of aligning connectable parts, connection of connectable parts, and sensing the connection of connectable parts, as will be described.

FIGS. 7-15B illustrate a medical device system 100 according to various embodiments of the present invention. The medical device system 100 may include features similar to the medical device systems discussed in the disclosure or employed as an embodiment of the medical devices (e.g., delivery device 12 in FIGS. 1-6C) discussed in the disclosure. Although the medical device system 100 may include features similar or used with the embodiments of FIGS. 1-6C, it should be understood that the medical device system 100 may also include some or all of the same features and operate in a manner similar to that shown and described in the embodiments of FIGS. 16-32B. In addition, some or all of the features shown in FIGS. 1-6C and 16-32B may be combined in various ways and included in the embodiments shown in FIGS. 7-15B. Likewise, it should be understood that any of the features of the embodiments of FIGS. 7-15B may be combined or otherwise incorporated into any of the other embodiments of FIGS. 7-15B as well as any other embodiment herein discussed.

A generalized representation of a first part 101 and a second part 102 of a medical device system 100, such as, but not limited to the delivery device 12 in FIGS. 1-6C as described above, is shown in FIG. 7. The first part 101 and the second part 102 may be configured to be connectable to each other or to be otherwise operatively engageable with each other. In some embodiments, a connection structure may be provided to secure the first part 101 and the second part 102 together for operation of the medical device system 100.

In further embodiments, the connection structure may include a magnetic structure for connecting the first part 101 and the second part 102. For example, a magnet may be provided on one of the first part 101 and the second part 102 and a magnetically attractive material, such as a magnet of opposite polarity, a metal, and/or the like may be provided on the other of the first part 101 and the second part 102. Such an example as well as other examples are disclosed in, but are not limited to, U.S. patent application Ser. No. 11/759,725, entitled "Infusion Medium Delivery Device and Method with Drive Device for Driving Plunger in Reservoir," herein incorporated by reference in its entirety.

Various embodiments, additionally or alternatively, may include other suitable structural features to aid in connecting the first part 101 and the second part 102. These may include, but are not limited to, adhesives, snap-fit structures, friction-fit structures, and/or the like on the first part 101 and/or the second part 102 that abut as the first part 101 and the second part 102 are brought together for connection. Other examples of various connection structures can be found, but are not limited to, U.S. patent application Ser. No. 12/553,038, filed Sep. 2, 2009, entitled "Insertion Device Systems and Methods," herein incorporated by reference in their entirety.

The first part 101 and the second part 102 may each be one of two housing portions, such as, but not limited to, a durable housing portion 30 (e.g., FIGS. 1-6C) and a disposable housing portion 20 (e.g., FIGS. 1-6C), as previously described. As previously discussed with respect to FIGS. 1-6C, the durable housing portion 30 may include various components, such as, but not limited to, a drive device 80, drive motor 84, drive device linkage portion 82, and/or the like. The disposable housing portion 20 may include various components, such as, but not limited to, a reservoir system 40. Returning to FIG. 7, alternatively, one of the first part 101 and the second part 102 may be a base portion 21 (e.g., FIGS. 1-6C) and the other of the first part 101 and the second part 102 may be a housing portion such as, but not limited to, the durable housing portion 30 and/or the disposable housing portion 20. In some embodiments, one of the housing portions may be a reservoir system 40 (e.g., FIGS. 1-6C).

In further embodiments, the medical device system 100 may include more than two housing portions. For example, such embodiments may include, but are not limited to, a durable housing portion 30, a disposable housing portion 20, and a base portion 21. Other housing portions may include, but are not limited to, an insertion device, electronics, and/or the like.

In some embodiments, one of the medical device system 100 parts (e.g., 101 in FIG. 7) may be provided with a first interactive element 104. The other medical device system 100 part (e.g., 102 in FIG. 7) may be provided with a second interactive element 106. The first interactive element 104 and the second interactive element 106 may be configured to interact with each other when in sufficiently close proximity to each other.

The first interactive element 104 may be arranged in a fixed relation to the first part 101, for example, by attaching, forming, or otherwise supporting the first interactive element 104 to a suitable location on a wall or on other structure of or in the first part 101. The second interactive element 106 may be arranged in a fixed relation to the second part 102, for example, by attaching, forming, or otherwise supporting the second interactive element 106 to a suitable location on a wall or on other structure of or in the second part 102. In some embodiments, the second interactive element 106 may be arranged on the second part 102 to be relative to the first interactive element 104 on the first part 101 in a case where the first part 101 and the second part 102 are connected or otherwise operatively engaged and the first part 101 and the second part 102 are properly aligned. Accordingly, the first interactive element 104 and the second interactive element 106 may be aligned. As such, the first interactive element 104 and the second interactive element 106, for example, may interact with each other in a case where the first part 101 and the second part 102 are connected or otherwise operatively engaged and the first interactive element 104 and the second interactive element 106 are properly aligned.

An interaction between the first interactive element 104 and the second interactive element 106 (or between any other interactive element discussed in the disclosure) may occur in a case where the first part 101 and the second part 102 are operatively engaged properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first part 101 and the second part 102 for operation. It should be understood that with respect to the embodiments described in the disclosure, operatively engaged may include connected and/or aligned, unless otherwise specified. Likewise, operatively engaged (and/or connected and/or aligned) may include operatively engaged properly (and/or connected properly and/or aligned properly), unless otherwise specified.

In various embodiments, the first interactive element 104 and the second interactive element 106 may be similar types of devices. For instance, in some embodiments, the first interactive element 104 may be configured to interact with second interactive elements (e.g., the second interactive element 106) and/or the second interactive element 106 may be configured to interact with first interactive elements (e.g., the first interactive element 104). For example, a first interactive element 104 may be a magnet arranged to provide an N (north) polarity and a second interactive element 106 may be a magnet arranged to provide an S (south) polarity. The first interactive element 104 may interact more effectively (e.g., connect and/or align) with the second interactive element 106 than with another first interactive element 104 arranged to provide an N polarity.

In various embodiments, the first interactive element 104 may be configured to interact with second interactive elements (e.g., the second interactive element 106), as well as other first interactive elements (e.g., first interactive element 104' (e.g., FIG. 8 discussed below)). In some embodiments, the second interactive element 106 may be configured to interact with first interactive elements (e.g., the first interactive element 104), as well as other second interactive elements (e.g., second interactive element 106' (e.g., FIG. 8 discussed below)).

In some embodiments, the first interactive element 104 and the second interactive element 106 may be dissimilar types of mechanisms. For example, a first interactive element 104 may be a ferrous conduit and a second interactive element 106 may be a magnet. The second interactive element 106 may interact with (e.g., connect and/or align) the first interactive element 104, as well as other magnetic second interactive elements 106. As another example, as described below with respect to, for example FIGS. 15A and 15B, first interactive element 204 may be a protrusion, pusher, finger, or other structural feature configured and/or arranged to act upon (e.g., urge) a second interactive element 206', and/or the like that may be for interacting with (e.g., functioning as a conductor for) another second interactive element 206.

Returning to FIG. 7, in some embodiments, suitable electronics may be connected to the first interactive element 104 and/or the second interactive element 106 to provide a controlled power signal to selectively activate or otherwise control one or more of the first interactive element 104 and the second interactive element 106 and/or other components as described in the disclosure.

In various embodiments, some or all of the interactive elements (e.g., first interactive element 104, second interactive element 106) may be integrated with the first part 101 and the second part 102 and/or be separate components placed in or on the first part 101 and the second part. For example, the interactive elements may be placed in or on the first part 101 and the second part 102 in a friction-fitting manner, during a molding a process, and/or the like. In some embodiments, one or more of the interactive elements may be insert mold labeled on its respective part. In some embodiments, a film cover may be provided for supporting one or more of the interactive elements.

In various embodiments, some or all of the interactive elements may have an exposed surface. The exposed surface of the interactive elements may be for allowing increased interactivity between each of the interactive elements, for example to allow a user to locate the interactive elements (e.g., to facilitate connection of the first part 101 and the second part 102), and/or the like. In other embodiments, some or all of the interactive elements may be covered, for example (but not limited to) being disposed completely within the first part 101 and/or the second part 102. Such embodiments may allow for protecting the interactive elements from damage, debris collection, mitigating interference with other components (e.g., other interactive elements, electronics in the medical device system 100, and/or the like), and/or the like.

In various embodiments, the first interactive element 104 and the second interactive element 106 may be properly aligned such as, but not limited to, when the first interactive element 104 and the second interactive element 106 align in one dimension or more than one dimension, are sufficiently proximate to each other, contact each other, an electrical or magnetic connection is established between the components, and/or the like. Any one or combination of these events may occur, for example, in a case where the first part 101 and the second part 102 are operatively engaged and positioned relative to each other in a predetermined manner. In other words, the first part 101 and the second part 102 have been connected sufficiently properly and/or otherwise within an operating threshold.

In other embodiments, the first interactive element 104 may be arranged on the first part 101 at a location to interact electronically (or magnetically) with the second interactive element 106 in a case where the first part 101 and the second part 102 are brought together and the first interactive element 104 and the second interactive element 106 are in relative close proximity to each other, such as, but not limited to, in contact with each other. In some embodiments, suitable electronics may be connected to at least one of the first interactive element 104 and the second interactive element 106 to provide a controlled power signal to selectively activate or otherwise control the first interactive element 104 and/or the second interactive element 106.

Figure 8:
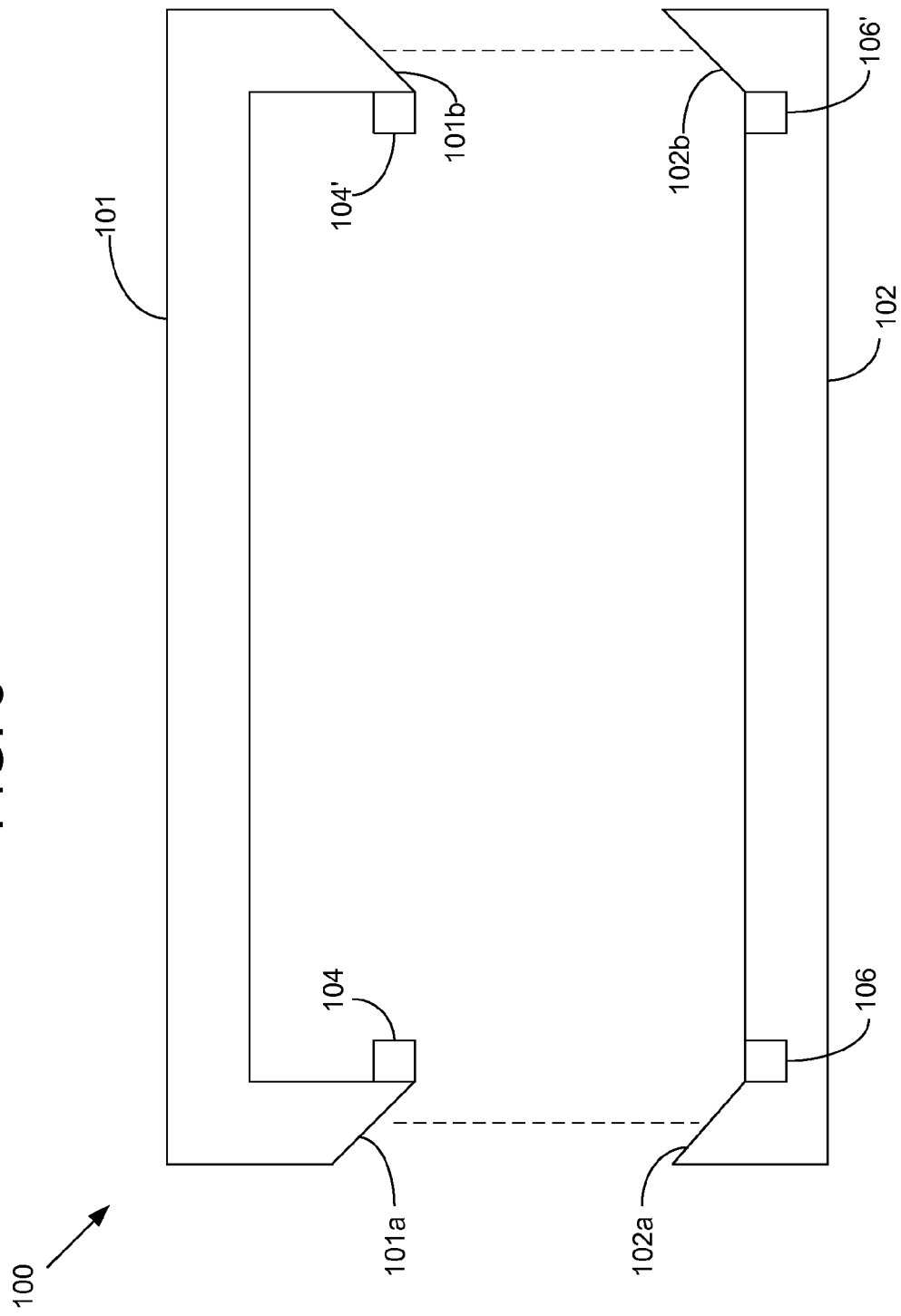
FIG. 8 illustrates a medical device system in accordance with an embodiment of the present invention.

In some embodiments, such as the embodiment exemplified in FIG. 8, multiple pairs of first interactive elements and second interactive elements may be provided on the first part 101 and the second part 102, for example, to provide a more reliable alignment between the first part 101 and the second part 102. In the illustrated embodiment, a second pair of interactive elements including a first interactive element 104' and a second interactive element 106' are shown as supported by the first part 101 and the second part 102 respectively in a manner similar to that described above for the first interactive element 104 and the second interactive element 106. In further embodiments, more than two pairs of interactive elements may be supported by the first part 101 and the second part 102, as previously described.

In various embodiments, the first interactive element 104 and the first interactive element 104' (and/or the second interactive element 106 and the second interactive element 106') may be dissimilar from each. For instance, in some embodiments, the first interactive element 104 may be configured to interact with second interactive elements (e.g., the second interactive element 106) and/or the first interactive element 104' may be configured to interact with second interactive elements (e.g., the second interactive element 106). For example, a first interactive element 104 may be a magnet arranged to provide an N (north) polarity and a second interactive element 106 may be a magnet arranged to provide an S (south) polarity. A first interactive element 104' may be a magnet arranged to provide an S (south) polarity and a second interactive element 106' may be a magnet arranged to provide an N (north) polarity. Thus, the first interactive element 104 may interact in a more mutually attracting manner (e.g., to connect and/or align) with the second interactive element 106 than the second interactive element 106'. Similarly, the first interactive element 104' may interact in a more mutually attracting manner (e.g., to connect and/or align) with the second interactive element 106' than the second interactive element 106.

Moreover, for instance, in some embodiments, the first interactive element 104 may be configured to interact with second interactive elements (e.g., the second interactive element 106), as well as other first interactive elements (e.g., first interactive element 104'). In some embodiments, the second interactive element 106 may be configured to interact with the first interactive elements (e.g., the first interactive element 104), as well as other second interactive elements (e.g., second interactive element 106'). For example, a first interactive element 104 may be a ferrous conduit and a second interactive element 106 may be a magnet. The second interactive element 106 may interact with (e.g., connect and/or align) the first interactive element 104 as well as other magnetic second interactive elements 106'.

In some embodiments, the first interactive element 104 and the first interactive element 104' and/or the second interactive element 106 and the second interactive element 106' may be dissimilar types of mechanisms. For example, as described with respect to, for example FIGS. 15A and 15B, a first interactive element 104 may be a protrusion, pusher, finger, or other structural feature configured and/or arranged to act upon (e.g., urge) a second interactive element 106' and/or the like arranged and/or configured to interact with (e.g., function as a conductive medium) a second interactive element 106.

With reference to FIG. 7, thus in various embodiments, as part of a process of assembling a first part 101 and a second part 102 of a medical device system 100, a user may bring the first part 101 and the second part 102 together to operatively engage each other or otherwise be in sufficiently close proximity. Accordingly, a first interactive element 104 and a second interactive element 106 (and/or a first interactive element 104' and a second interactive element 106') may be interactable with each other to determine, for example, whether the first part 101 and the second part 102 have been properly aligned.

In some embodiments, the interactive elements (e.g., first interactive element 104, first interactive element 104', second interactive element 106, and second interactive element 106') may be configured to help a user-patient align the first part 101 and the second part 102 relative to each other for proper connection. For example, one or more pairs of interactive element 104, 106, 104', and/or 106' may be arranged at one or more appropriate locations on the first part 101 and the second part 102 to allow an indicator or indicator device 420 (e.g., FIG. 48) associated with the medical device system 100 to provide an indication that the first part 101 and the second part 102 are properly aligned in one or more dimensions relative to each other. Alternatively or in addition, one or more pairs of interactive element 104, 106, 104', and/or 106' may be of suitable size(s), shape(s), orientation(s), and position(s) to allow an indicator associated with the medical device system 100 to provide an indication that the first part 101 and the second part 102 are properly aligned in one or more dimensions relative to each other. For example, the indicator may provide an indication that the first part 101 and the second part 102 are properly connected in a case where the first interactive element 104 and the second interactive element 106 interact.

In some embodiments, such as the embodiment exemplified in FIG. 9, a conductive medium 108 may be at a position adjacent one of the interactive element(s) (e.g., the second interactive element 106 in FIG. 9) or otherwise in communication with the interactive element to allow the conductive medium 108 to function as a conductor for the interactive element. In such embodiments, the interactive element may interact with the conductive medium 108 to allow the conductive medium 108 to be have similar characteristics or properties, though not necessarily exactly the same characteristics or properties. For example, a magnetic second interactive element 106 may provide a magnetic charge to a magnetic conductive medium 108. The conductive medium 108 may be made of a material, such as, but not limited to, an electrically conductive material (e.g., metal, graphite, salt solutions, plasma, and/or the like), a magnetically attractive material (e.g., metal), and/or the like. In some embodiments, the conductive medium 108 may be a sufficiently high thermally conductive material (e.g., metal, or any other material with a thermal conductivity, for example (but not limited to), above 1), and/or the like.

In further embodiments, the conductive medium 108 may be arranged on its respective part (e.g., the second part 102 in FIG. 9) to allow the interactive element (e.g., the second interactive element 106 in FIG. 9) to be interactable with the other interactive element (e.g., the first interactive element 104 in FIG. 9) on the opposing part (e.g., the first part 101 in FIG. 9) via the conductive medium 108 in any of the manners described in the disclosure. For example, in particular embodiments, the first interactive element 104 may interact with the conductive medium 108 in a case where the first part 101 and the second part 102 are operatively engaged properly. Accordingly, the first interactive element 104 and the second interactive element 106 may be interactable with each other via the conductive medium 108. Thus, some embodiments may allow the first interactive element 104 to interact with the conductive medium 108 in addition to or alternative to the second interactive element 106. For example, a magnetic second interactive element 106 may magnetize a magnetically attractive conductive medium 108, which may then interact with the first interactive element 104.

In some embodiments, the conductive medium 108 may be arranged at a position adjacent the other interactive element (e.g., the first interactive element 104) or otherwise in communication with the other interactive element to allow the conductive medium 108 to function as a conductor for the other interactive element. In further embodiments, the conductive medium 108 may be arranged on its respective part to allow the other interactive element to be interactable with the interactive element (e.g., the second interactive element 106) on the opposing part via the conductive medium 108 in any of the manners described in the disclosure. For example, in particular embodiments, the second interactive element 106 may interact with the conductive medium 108 in a case where the first part 101 and the second part 102 are operatively engaged properly. Accordingly, the first interactive element 104 and the second interactive element 106 may be interactable with each other via the conductive medium 108. Thus, some embodiments may allow for the second interactive element 106 to interact with the conductive medium 108 in addition to or alternative to the first interactive element 106. For example, an electrical connection between the first interactive element 104 and the second interactive element 106 may be established by contacting the conductive medium 108 (e.g., electrically conductive medium).

In some embodiments, the indicator may be configured to provide an indication corresponding to a type of alignment, for example, that a maximum alignment or a minimum required alignment has been achieved between the first interactive element 104 and the second interactive element 106 during connection of the first part 101 and the second part 102. In some embodiments, the indicator may be configured to provide an indication corresponding to various stages of alignment, for example, no alignment, alignment in one or more axes and misalignment in one or axes, complete alignment, and/or misalignment after alignment, and/or the like.

In various embodiments, additional structural features may be provided on one or both of the first part 101 and the second part 102 to provide a mechanical alignment function. Such additional structural features may include a first sloped surface 101a on the first part 101 arranged to mate or otherwise engage a corresponding sloped surface 102a on the second part 102. As the first part 101 and the second part 102 are brought together, a misalignment of the first part 101 and the second part may result in the first sloped surface 101a and the second sloped surface 102a engaging each other. Accordingly, the first sloped surface 101a and the second sloped surface 102 may engage each other in a position at which the first sloped surface 101a and the second sloped surface 102a may slide relative to each other toward a proper alignment position.

In some embodiments, multiple pairs of sloped surfaces may be provided on the first part 101 and the second part 102, for example, to provide alignment in one or more directions and/or one or more dimensions. For example, in some embodiments, such as the embodiment exemplified in FIGS. 8, the first part 101 and the second part 102 may include a second pair of sloped surfaces including a first sloped surface 101b and a second sloped surface 102b in a manner similar to that described above for the first sloped surface 101a and the second sloped surface 102a. The second pair of sloped surfaces may have a similar or different size and/or shape than the first part of sloped surfaces.

Figure 10B:
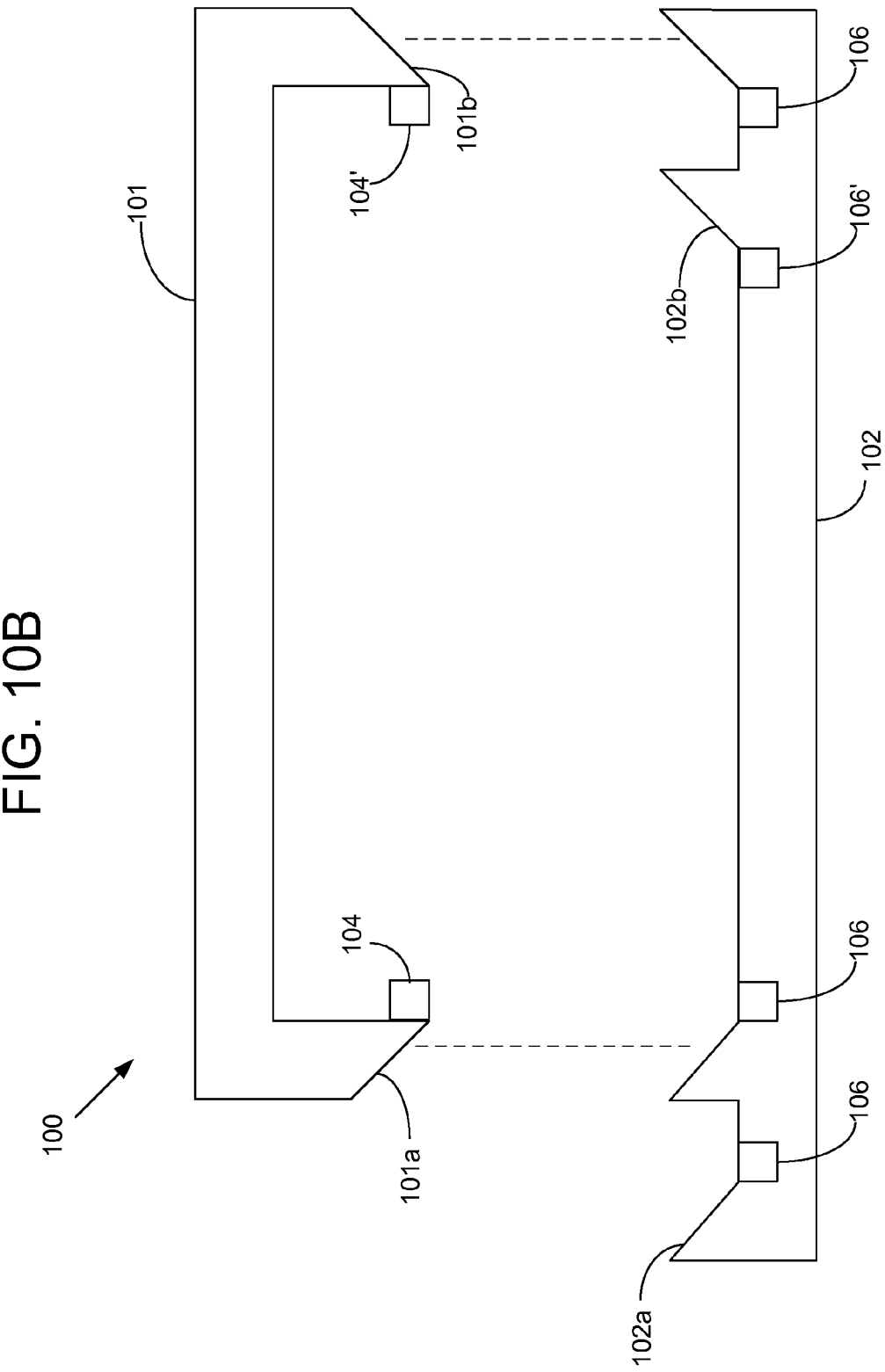
FIG. 10B illustrates a medical device system in accordance with an embodiment of the present invention.

In some embodiments, such as the embodiments exemplified in FIGS. 10A and 10B, at least one of the first part 101 and the second part 102 may include one or more sloped surfaces arranged to mate with corresponding sloped surfaces on the other of the first part 101 and the second part 102. In such embodiments, at least one of the one or more sloped surfaces may be mated with one or more of the plurality of corresponding sloped surfaces so that the first part 101 and the second part 102 can be aligned and/or connected in multiple orientations.

In further embodiments, some or all of the interacting components, such as the first interactive element 104 and the second interactive element 106, may be arranged along the first part 101 and the second part 102 to allow the first part 101 and the second part 102 to be connected and/or aligned in multiple orientations. For example, in FIGS. 10A and 10B, the second part 102 may include multiple sets of second interactive elements 106 and multiple sets of second interactive elements 106', thus allowing the first interactive element 104 to be selectively aligned with any of the second interactive elements 106 while allowing the first interactive element 104' to be aligned with at least one of the second interactive elements 106'. As such, the first part 101 and the second part 102 can be aligned and/or connected in at least a first orientation (e.g., FIG. 10A) and a second orientation (e.g., FIG. 10B). As another example, the first part 101 may include multiple sets of first interactive elements 106 and multiple sets of first interactive elements 104' for allowing selective alignment with the second interactive element 106 and the second interactive element 106', respectively.

Figure 11:
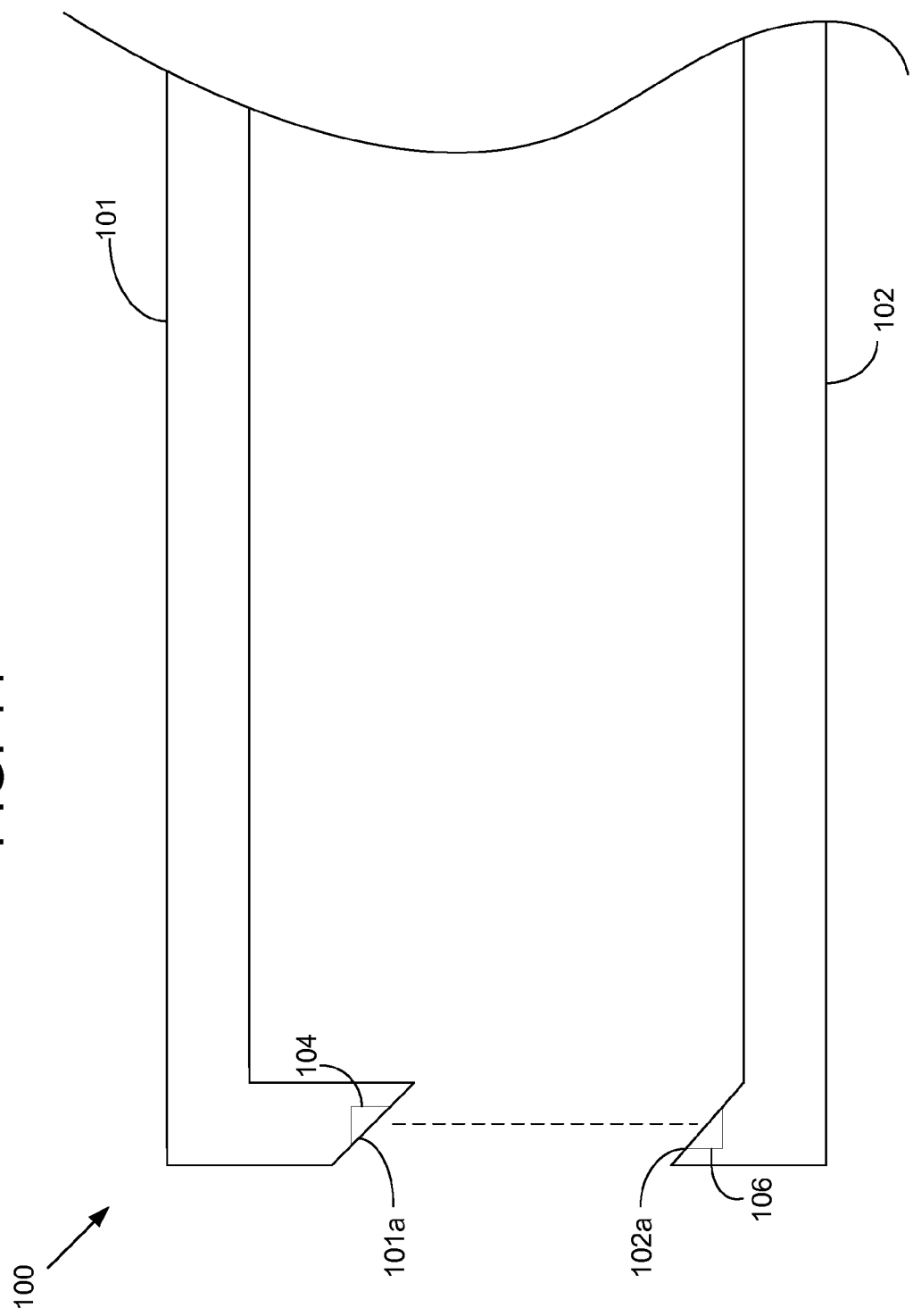
FIG. 11 illustrates a medical device system in accordance with an embodiment of the present invention.

In some embodiments, such as the embodiment exemplified in FIG. 11, the interactive elements (e.g., first interactive element 104, first interactive element 104', second interactive element 106, second interactive element 106', and/or the like) may be supported and/or be part of the sloped surfaces 101a, 102a to provide an alignment and connection function as described in the disclosure. Various embodiments may additionally or alternatively include other suitable structural features to aid in the alignment, including, but not limited to, curved or stepped surfaces, rollers and/or the like on the first part 101 and the second part 102 that abut as the first part 101 and the second part 102 are brought together for connection. In some embodiments, one or both of the first part 101 and the second part 102 may include a magnetic connection and/or alignment structure, such as that disclosed in U.S. patent application Ser. No. 11/759,725 entitled "Infusion Medium Delivery Device and Method with Drive Device for Driving Plunger in Reservoir," herein incorporated by reference in its entirety.

Figure 12:
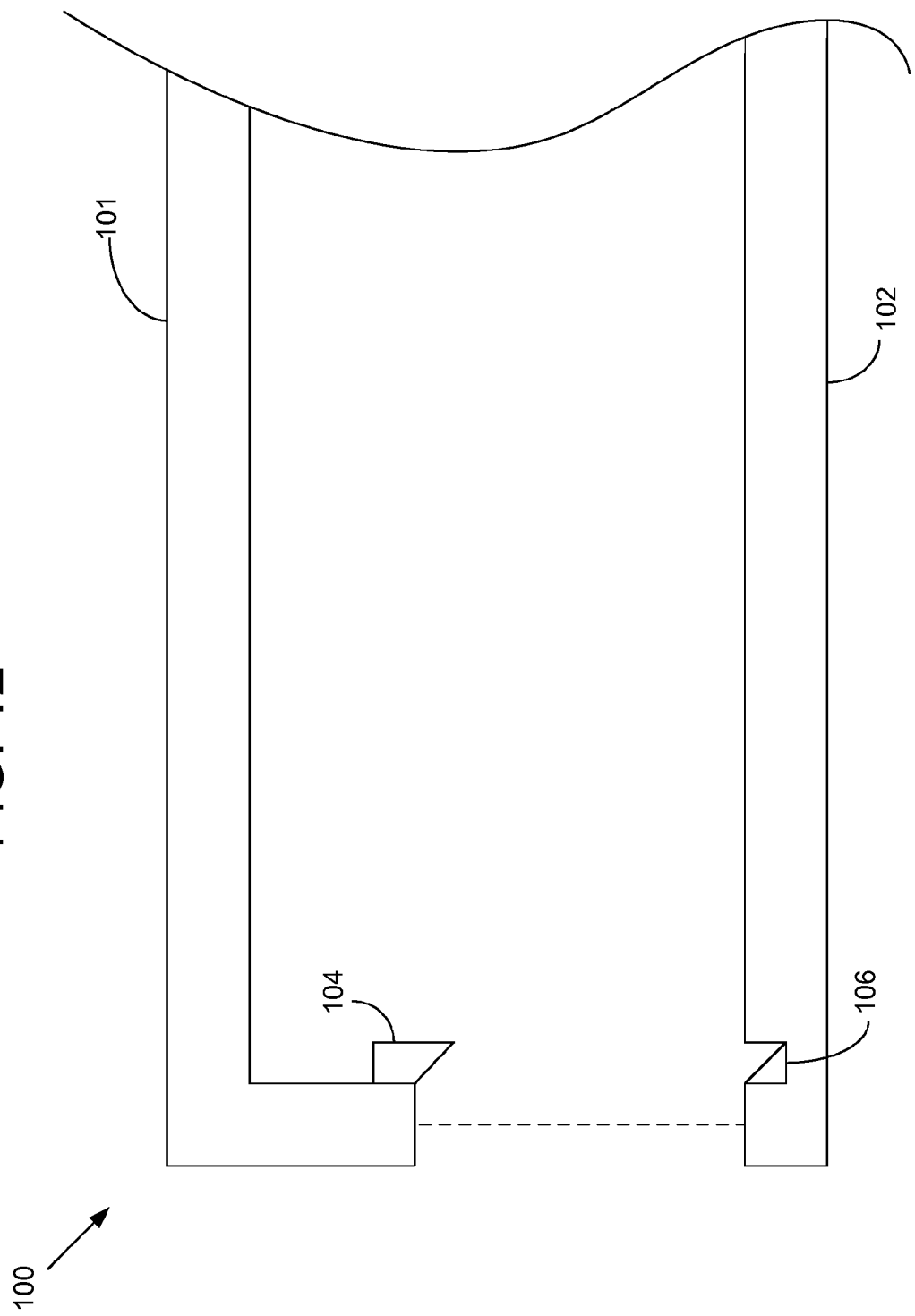
FIG. 12 illustrates a portion of a medical device system in accordance with an embodiment of the present invention.
Figure 13:
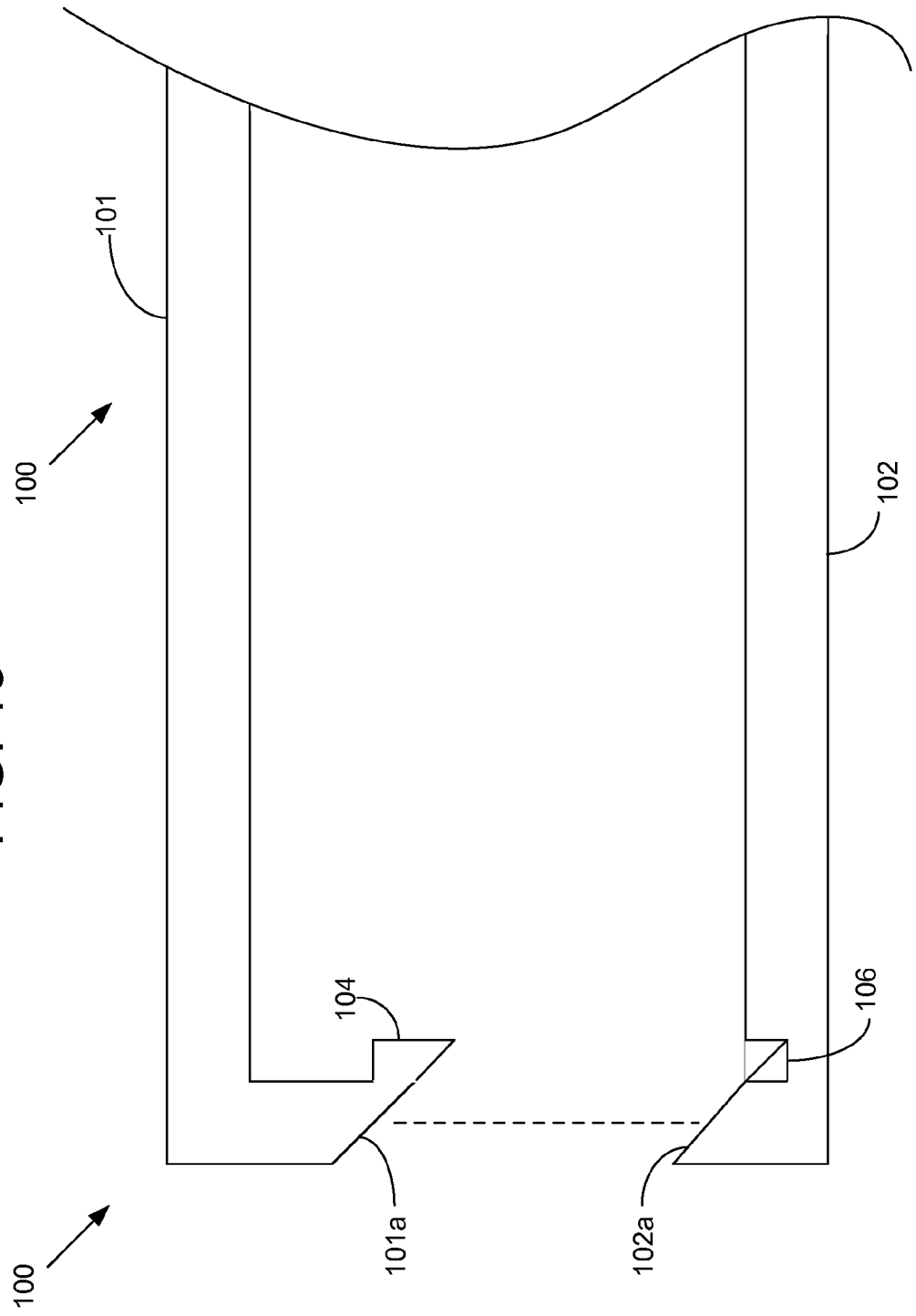
FIG. 13 illustrates a medical device system in accordance with an embodiment of the present invention.
Figure 17:
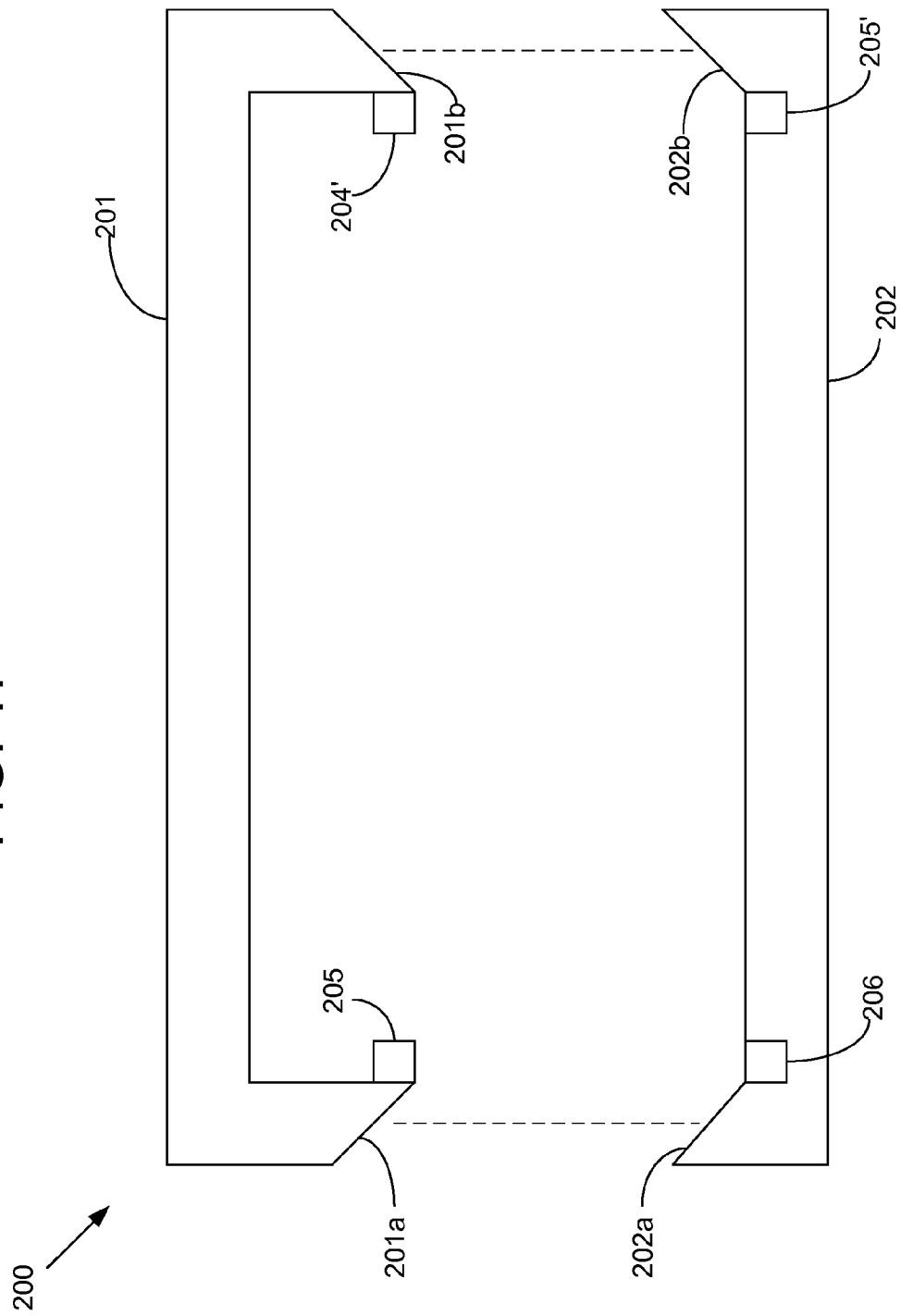
FIG. 17 illustrates a medical device system in accordance with an embodiment of the present invention.

In some embodiments, such as the embodiment exemplified in FIG. 12, one or both of the first interactive element 104 and the second interactive element 106 may have a mating, sloped or otherwise shaped surface for engaging and providing an alignment function when the first part 101 and the second part 102 are brought together for connection. For example, the first interactive element 104 may have a sloped surface adapted to be mated with a corresponding sloped surface of the second interactive element 106 in a manner similar to that described with respect to the first sloped surface 101a (e.g., FIGS. 7-11) and the second sloped surface 102a (e.g., FIGS. 7-11). In further embodiments, such as the embodiment exemplified in FIG. 13, one or both of the first part 101 and the second part 102 may include sloped surfaces 101a, 102a for mating with interactive elements (e.g., first interactive element 104, second interactive element 106) having appropriately shaped surfaces similar to that previously described.

In various embodiments, such as the embodiments exemplified in FIGS. 14A and 14B, one or more of the interactive elements (e.g., first interactive element 104, first interactive element 104', second interactive element 106, second interactive element 106', and/or the like) may be a spring, finger, or other bias member for contacting one or more of the other interactive elements upon the first part 101 and the second part 102 being operatively engaged. In such embodiments, the one or more of the interactive elements may be made of a suitably rigid material, such as, but not limited to, metal, plastic, glass, composite materials, rubber, and/or the like.

For example, as shown in FIG. 14A, the second interactive element 106 may be biased toward a first position, for example an extended position. As the first part 101 and the second part 102 are brought together, the second interactive element 106 may be urged by a portion of the opposing part to a second position, for example a collapsed position (e.g., FIG. 14B). For instance, in FIGS. 14A and 14B, the first interactive element 104 supported by the first part 101 may urge the second interactive element 106 to the second position upon operatively engaging the first part 101 and the second part 102.

In some embodiments, a spring, finger, or bias member may be arranged or otherwise provided between the interactive elements for allowing the interactive elements to interact with each other via the bias member, for example, upon the first part 101 and the second part 102 being operatively engaged. In further embodiments, the bias member may function as a conductor (e.g., an electrically conductive medium, magnetically conductive medium, thermally conductive medium, and/or the like), such as a metal and/or the like, between the interactive elements. For example, in embodiments where the bias remember is an electrically conductive medium, the bias member may be arranged and/or configured for allowing an electrical connection between the interactive elements via the bias member.

Alternatively or in addition, in some embodiments, one or more of the interactive elements may be supported by a spring, finger, or other bias member for contacting the other interactive element upon the first part 101 and the second part 102 being operatively engaged. Thus in such embodiments, the supported interactive element(s) may be biased in a first direction (e.g., FIG. 14A) and/or urgeable or otherwise moveable to a second position (e.g., FIG. 14B) as previously described.

In various embodiments, such as the embodiments exemplified in FIGS. 15A and 15B, more than one interactive element (e.g., first interactive element 104, first interactive element 104', second interactive element 106, second interactive element 106', and/or the like) may be spaced apart from each other on one of the first part 101 and the second part 102. At least one of the more than one interactive element (e.g., second interactive element 106) or a portion thereof may be movable by a portion (e.g., interactive element 104, a finger, pusher, and/or the like) of the other of the first part 101 and the second part 102 upon the first part 101 and the second part 102 being operatively engaged.

Thus, for example, as shown in FIGS. 15A and 15B, upon the first part 101 and the second part 102 being operatively engaged, the second interactive element 106' may be urged by the first interactive element 104 toward the second interactive element 106. Accordingly, the second interactive element 106' may be moved to contact or otherwise placed within range with the second interactive element 106 to allow some or all of the interactive elements (e.g., first interactive element 104, second interactive element 106', and/or second interactive element 106) to interact with each other. Likewise, in other embodiments, the first interactive element 104' (not shown) may be moved to contact or otherwise placed within range with the first interactive element 104 in a similar manner to allow the interactive elements (e.g., first interactive element 104, first interactive element 104', second interactive element 106, and/or the like) to interact with each other.

In some embodiments, for example, the first interactive element 104 and the second interactive element 106 can be arranged on one of the first part 101 and the second part 102 to be spaced apart and movable relative to each other in a manner such as that previously described. In such embodiments, for instance, a portion of the other of the first part 101 and the second part, such as a tab, finger, and/or the like may be arranged to urge the first interactive element 104 and the second interactive element 106 toward each other to allow the interactive elements to interact (e.g., contact) with each other. Thus in such embodiments, most or all of the interactive elements may be provided on one of the housing portions, for example the durable housing portion 30 (FIGS. 1-6C), which may allow for reuse of the interactive elements. In other embodiments, the movable interactive element may be any suitable intermediary member (e.g., second interactive element 106' in FIGS. 15A and 15B) configured to be movable relative to one or more of the interactive elements in a manner described, for example, with respect to FIGS. 15A and 15B.

In other embodiments (see, e.g., FIG. 31 described later), the movable interactive element (or a portion thereof) may instead be a flexible layer, such as a film made of a suitably flexible material including, but not limited to, a Mylar and/or the like, that can be pushed upon by the portion of the opposing part to contact the other interactive element. In further embodiments, the flexible layer may be a conductive layer, such an electrically conductive medium (e.g., metal and/or the like), magnetically conductive medium (e.g., a ferrous conduit), thermally conductive medium, and/or the like.

Thus in various embodiments, as part of a process of assembling a first part 101 and a second part 102 of a medical device system 100, a user may bring the first part 101 and the second part 102 together to operatively engage each other or otherwise be in sufficiently close proximity. Accordingly, a first interactive element 104 and a second interactive element 106 may be interactable with each other to determine, for example, whether the first part 101 and the second part 102 have been properly aligned and/or connected.

In various embodiments, the interactive elements (e.g., first interactive element 104, second interactive element 106, and/or the like) may allow for, but is not limited to, tracking a number of times a component has been connected to and/or disconnected from other components, verifying proper connection and/or alignment of components in a medication delivery system prior to each delivery step, checking, sensing, and/or measuring parameters, such as ambient parameters (e.g., ambient magnetic fields), operating parameters, and/or the like, alerting users to conditions, such as conditions outside operating parameters of the delivery system, and/or the like.

Various embodiments may employ different arrangements of interactive elements on the first part 101 and/or the second part 102. For instance, in embodiments in which one of the first part 101 and the second part 102 is intended to be disposable (e.g., disposed of after one or a prescribed number of uses or period of use), some of the interactive elements may be provided on the disposable part, while other interactive elements may be provided on a durable part (i.e., not intended to be disposed). As a result, after a period of usage, the interactive element(s) on the disposable part that may have attracted and collected stray material can be disposed of with the disposable part.

On the other hand, the interactive element(s) on the durable part can be sufficiently clean and free (or be cleaned) of stray material for further usage. In such embodiments, arranging at least some of the interactive element(s) on the durable portion may provide certain advantages, such as, but not limited to, being more cost-effective, for example, by arranging interactive elements on respective parts based on cost; easier to manufacture and/or install, and/or the like. For example, electronics and circuitry, such as, but not limited to, a sensor (e.g., FIGS. 16-23), a responsive device (e.g., FIGS. 24-29B and 48), and/or other circuitry or electronics, may be arranged on the durable part.

In yet other embodiments, arranging at least some of the interactive element(s) on the disposable portion may provide certain advantages, such as, but not limited to, maintenance, cost, and/or the like. For example, such embodiments may allow for the interactive element(s) that have worn down, been contaminated, or otherwise collected stray material to be disposed of with the disposable part.

FIGS. 16-19 illustrate a medical device system 200 according to various embodiments of the present invention. The medical device system 200 may include features similar to or employed as an embodiment of the medical device system 100 (e.g., FIGS. 7-15B) and/or the other medical device systems discussed in the disclosure. Although the medical device system 200 may include features similar or used with the embodiments of FIGS. 7-15B, it should be understood that the medical device system 200 may also include some or all of the same features and operate in a manner similar to that shown and described in the embodiments of FIGS. 1-6C and 20-32B. In addition, some or all of the features shown in FIGS. 1-15B and 20-32B may be combined in various ways and included in the embodiments shown in FIGS. 16-19. Likewise, it should be understood that any of the features of the embodiments of FIGS. 16-19 may be combined or otherwise incorporated into any of the other embodiments of FIGS. 16-19 as well as any other embodiment herein discussed.

In some embodiments, such as the embodiment exemplified in FIG. 16, at least one of a first interactive element 204, which may be similar to first interactive element 104 (e.g., FIGS. 7-15B), and a second interactive element 206, which may be similar to the second interactive element 106 (e.g., FIGS. 7-15B), may be a suitable sensor 205 for sensing the other of the first interactive element 204 and the second interactive element 206 and/or an interactive element, such as a conductive medium (e.g., FIG. 18 discussed later) operatively connected to or otherwise associated with the other of the first interactive element 204 and the second interactive element 206. Accordingly, upon the sensor 205 detecting the presence of the other of the first interactive element 204 and the second interactive element 206, the alignment system 200 may determine whether the first part 201 and second part 202 have been properly connected (i.e., aligned and connected).

In various embodiments, suitable electronics may be connected to the sensor 205 and/or the other of the first interactive element 204 and the second interactive element 206 to provide a controlled power signal to selectively activate or otherwise control the sensor 205 and/or the other of the first interactive element 204 and the second interactive element 206. For example, the sensor 205 may be controlled to activate upon a manual activation of a control button, switch, or other manual operator on one of the connectable components or on a remote-controller device (not shown) connected in wireless communication with the sensor 205 through suitable control electronics. As another example, the sensor 205 may be controlled to activate automatically after a certain action, such as activation of a button, and/or the like or after a certain amount of time. In some embodiments, the sensor 205 may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor 205 may be activated, for example, before or after, the first part 201 and the second part 202 are brought operatively engaged.

In some embodiments, the sensor 205 may be activated upon interacting with the other of the first interactive element 204 and the second interactive element 206. In some embodiments, an activating element, such as an activating magnet and/or the like, may be provided on at least one of the first part 201 and the second part 202. The activating element may activate the sensor 205 upon interacting with each other, for example by contacting each other when the first part 201 and the second part 202 are operatively engaged and properly aligned. In particular embodiments, the activating element may be one of the interactive elements.

The sensor 205 may be any suitable detector configured to detect a detectable feature, such as an interactive element (e.g., first interactive element 204, second interactive element 206, and/or the like) or a presence of an interactive element, such as a magnetic field, electric field, and/or the like provided by the interactive element. In further embodiments, the sensor 205 may be configured to and/or associated with electronics configured to produce an electronically detectable state or signal upon detecting the detectable feature. For example, the sensor 205 may be a sensor pad and/or the like configured to sense, detect, and/or otherwise interact with an interactive element upon the interactive element being in sufficient proximity (e.g., in contact) with the sensor pad. In certain embodiments, the sensor 205 may include a conventional activating switch or a conventional device capable of detecting a particular detectable feature such as an interactive element (e.g., first interactive element 204, second interactive element 206, and/or the like) or a presence of an interactive element, such as a magnetic field, electric field, and/or the like provided by the interactive element.

In some embodiments, the sensor 205 may be configured to sense, detect, or measure a presence of the interactive element. For example, such embodiments may allow for the sensor 205 to sense a presence (e.g., a magnetic field) of the interactive element rather than the element itself. In particular, the sensor 205 may be configured to sense, detect, or measure, but is not limited to, magnetic fields; electric fields; temperature or heat; optical and/or visual features (e.g., barcodes, colors, grayscale, and/or the like); tactile features; audio features; radio frequencies (RF) or other radio signals; ultraviolet light, or other light; force; torque; resistances (e.g., coded resistance pattern); capacitances; inductances; ultrasonic signals, and/or the like; and/or the like provided by, emitted from, produced by, or otherwise present in an interactive element (e.g., the second interactive element 206).

For example, the sensor 205 may be configured to sense a magnetic field emitted by a magnetic second interactive element 206 in a case where the first part 201 and the second part 202 are connected and the sensor 205 and the second interactive element 206 are in proper alignment. If the first part 201 and the second part 202 are operatively engaged and the sensor 205 fails to detect the magnetic field provided by the magnetic second interactive element 206, then this may indicate that the first part 201 and the second part 202 are not properly aligned. On the contrary, if the first part 201 and the second part 202 are operatively engaged and the sensor 205 detects the magnetic field provided by the magnetic second interactive element 206, then this may indicate that the first part 201 and the second part 202 are properly aligned (i.e., the first part 201 and the second part 202 are within a certain tolerance of alignment relative to each other).

In further embodiments, the sensor 205 may be configured to measure a value or presence parameter, magnitudes, changes, gradients, polarities, vectors, field directions, and/or any other measurable parameter suitable for detecting and/or measuring a detectable feature. For example, a sensor 205 may be configured to measure a gauss level of a magnetic field provided by a second interactive element 206.

In various embodiments, the detectable feature (e.g., second interactive element 206) may be selected, configured, and/or arranged to provide a particular detectability (i.e., a characteristic or trait capable of being detected) such that, for example, the interactive element and/or the presence of the interactive element may be sensed by the sensor 205 only when the first part 201 and the second part 202 are properly aligned. For instance, a magnetic second interactive element 206 may be selected to provide a magnetic field having a particular gauss level that may be detectable by the sensor 205 only if sufficiently proximate to the magnetic second interactive element (i.e., the first part 201 and the second part 202 are within a certain tolerance of alignment relative to each other).

Alternatively or in addition, the sensor 205 may be selected, configured, and/or arranged to select a sensitivity of the sensor or otherwise control an amount sensed of the detectable feature by the sensor 205. Thus, for example, the interactive element and/or the presence of the interactive element may be sensed by the sensor 205 only when the first part 201 and the second part 202 are properly aligned; otherwise, the detectable feature would not be sufficiently proximate to be detectable by the sensor 205 having a reduced sensitivity. For instance, a sensor 205 may be configured to sense, for example, a magnetic second interactive element 206 or a field of the magnetic second interactive element 206 only if sufficiently proximate to the magnetic second interactive element 206.

Such embodiments may allow, for example, for a lesser tolerance in connecting the first part 201 and the second part 202. Accordingly, such embodiments may be used in a case where a connection between the first part 201 and the second part 202 need (but not limited to) more precision. In other embodiments, the sensor may have an increased sensitivity or the like. Such embodiments may allow, for example, for a greater tolerance in connecting the first part and second part.

In some embodiments, the sensor 205 or other associated circuitry may be configured such that a detection not meeting a certain range (e.g., below the range or above the range) or threshold may be ignored or otherwise determined to be unacceptable by the sensor 205 (or other associated circuitry). Thus, in such embodiments, a case where the sensor 205 does not detect the interactive element and/or the presence of the interactive element, the sensor 205 (or other circuitry) may provide an indication that the first part 201 and the second part 202 have not been properly engaged (e.g., connected and/or aligned).

In yet further embodiments, the sensor 205 and/or other associated electronics may be configured such that a detection not meeting a certain range or threshold (i.e., determined to be unacceptable) may provide an indication that the detection does not meet the certain range or threshold. For example, such an indication may indicate that the first part 201 and the second part 202 are operatively engaged, but not properly aligned. In further embodiments, the indicator may indicate, for example, that the parts are laterally misaligned in one or more directions, the parts are have not been brought sufficiently together, and/or the parts have not been connected properly (e.g., connected backwards).

In some embodiments, other interactive elements or structures may be provided to regulate the sensing and/or measuring ability of the sensor 205 and/or the detectability and/or measurability of the detectable feature. For example, a heat-emitting second interactive element 206 may be at least partially surrounded by a low thermally conductive material, such as plastic, rubber, wood, and/or the like. This may allow a heat-sensing sensor 205 to sense the heat-emitting second interactive element 206 and/or a suitable presence thereof only when the first part 201 and the second part 202 are properly aligned, thus substantially preventing a false detection of heat that may be emitted, for example, laterally from the heat-emitting second interactive element 206.

In various embodiments, one of the interactive elements may have a capacitance that is measurable. Another interactive element (or other component) may be configured to affect the capacitance of the one of the interactive elements, for example, by being brought in proximity or contact with the one of the interactive elements. The affected capacitance of the one of the interactive elements may be measured or otherwise, for example, by a sensor (e.g., sensor 205) detected to indicate a change in state (e.g., that two components have been connected).

In various embodiments, one of the interactive elements may have an inductance that is measurable. Another interactive element (or other component) may be configured to affect the inductance of the one of the interactive elements, for example, by being brought in proximity or contact with the one of the interactive elements. The affected inductance of the one of the interactive elements may be measured or otherwise, for example, by a sensor (e.g., sensor 205) detected to indicate a change in state (e.g., that two components have been connected).

In some embodiments having multiple pairs of interactive elements, the first interactive element 204 and the first interactive element 204' may be sensor 205 and sensor 205' respectively that may be configured to detect, for example, the second interactive element 206 and the second interactive element 206' respectively. Thus, the system 200 may be deemed to have been properly connected in case where the sensor 205 detects the second interactive element 206 and the sensor 205' detects the second interactive element 206'. In other embodiments, the second interactive element 206 and the second interactive element 206' may be sensor 205 and sensor 205' respectively that may be configured to detect, for example, the first interactive element 204 and the first interactive element 204' respectively. In some embodiments, such as the embodiment exemplified in FIG. 17, at least one of the first interactive element 204 and the first interactive element 204' may be a sensor 205 configured to detect one of the second interactive element 206 and the second interactive element 206' and the other of the second interactive element 206 and the second interactive element 206' may be a sensor 205' configured to detect the other of the first interactive element 204 and the first interactive element 204'.

In some embodiments, both the first interactive element 204 and the second interactive element 206 may each be sensors 205. In such embodiments, one or more of the sensors 205 may be configured to detect the other sensor 205 and/or other interactive element(s). For example, the first part 201 and the second part 202 may be deemed to have been operatively engaged properly in a case where (but not limited to) one of the sensors 205 detects the other sensor 205, the sensors 205 both detect each other, one or more of the sensors 205 detects an other interactive element, and/or the like.

In further embodiments, further sensors may be provided for detecting other sensors (and/or interactive elements). In such embodiments, the first part 201 and the second part 202 may be deemed to have been operatively engaged properly, but is not limited to, upon one or more or a predetermined amount of the sensors 205 detecting a particular or any of the other sensors 205, the sensors 205 detecting each other, one or more of the sensors 205 detecting an other interactive element, and/or the like.

In various embodiments, one or more additional sensing structures, such as those described above, may be provided to align the first part 201 and the second part 202, for example, to increase reliability of alignment and/or decrease time for sensing proper alignment.

Thus in various embodiments, as part of a process of assembling a first part 201 and a second part 202 of a medical device system 200, a user may bring the first part 201 and the second part 202 together to operatively engage each other or otherwise be in sufficiently close proximity. Accordingly, a sensor 205 may detect a detectable feature to determine, for example, whether the first part 201 and the second part 202 have been operatively engaged properly (e.g., aligned and/or connected).

Figure 18:
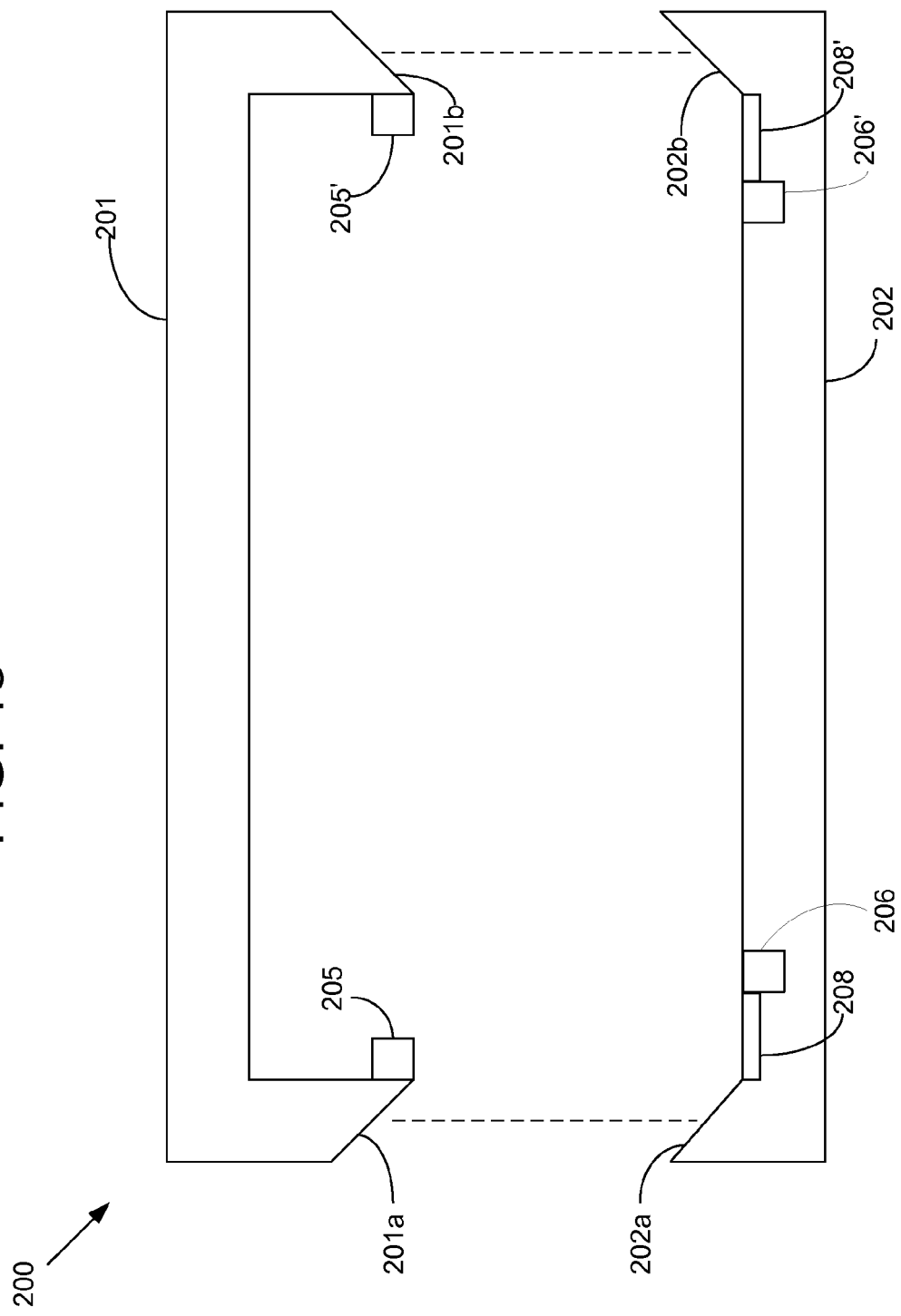
FIG. 18 illustrates a medical device system in accordance with an embodiment of the present invention.

In some embodiments, such as the embodiment exemplified in FIG. 18, a conductive medium 208 may be at a position adjacent one of the interactive element(s) (e.g., the second interactive element 206 in FIG. 18) or otherwise in communication with the interactive element to allow the conductive medium 208 to function as a conductor for the interactive element. In such embodiments, the interactive element may interact with the conductive medium 208 to allow the conductive medium 208 to be have similar characteristics or properties, though not necessarily exactly the same characteristics or properties. For example, a magnetic second interactive element 206 may provide a magnetic charge to a magnetic conductive medium 208. The conductive medium 208 may be made of a material, such as, but not limited to, an electrically conductive material (e.g., metal, graphite, salt solutions, plasma, and/or the like), a magnetically attractive material (e.g., metal), a sufficiently high thermally conductive material (e.g., metal, or any other material with a thermal conductivity, for example (but not limited to), above 1), and/or the like.

In further embodiments, the conductive medium 208 may be arranged on its respective part to allow the interactive element to be interactable with the other interactive element (e.g., the sensor 205 in FIG. 18) on the opposing part via the conductive medium 208 in any of the manners described in the disclosure. For example, in particular embodiments, the sensor 205 may detect or otherwise interact with the conductive medium 208 in a case where the first part 201 and the second part 202 are operatively engaged properly. Accordingly, the second interactive element 206 or presence thereof may be detectable by the sensor 205 via the conductive medium 208. Thus, some embodiments may allow for the sensor 205 to detect the conductive medium 208 in addition to or alternative to the interactive element (e.g., the second interactive element 206). For example, a magnetic second interactive element may magnetize a magnetically attractive conductive medium 208, which may then be detected by the sensor 205.

Figure 19:
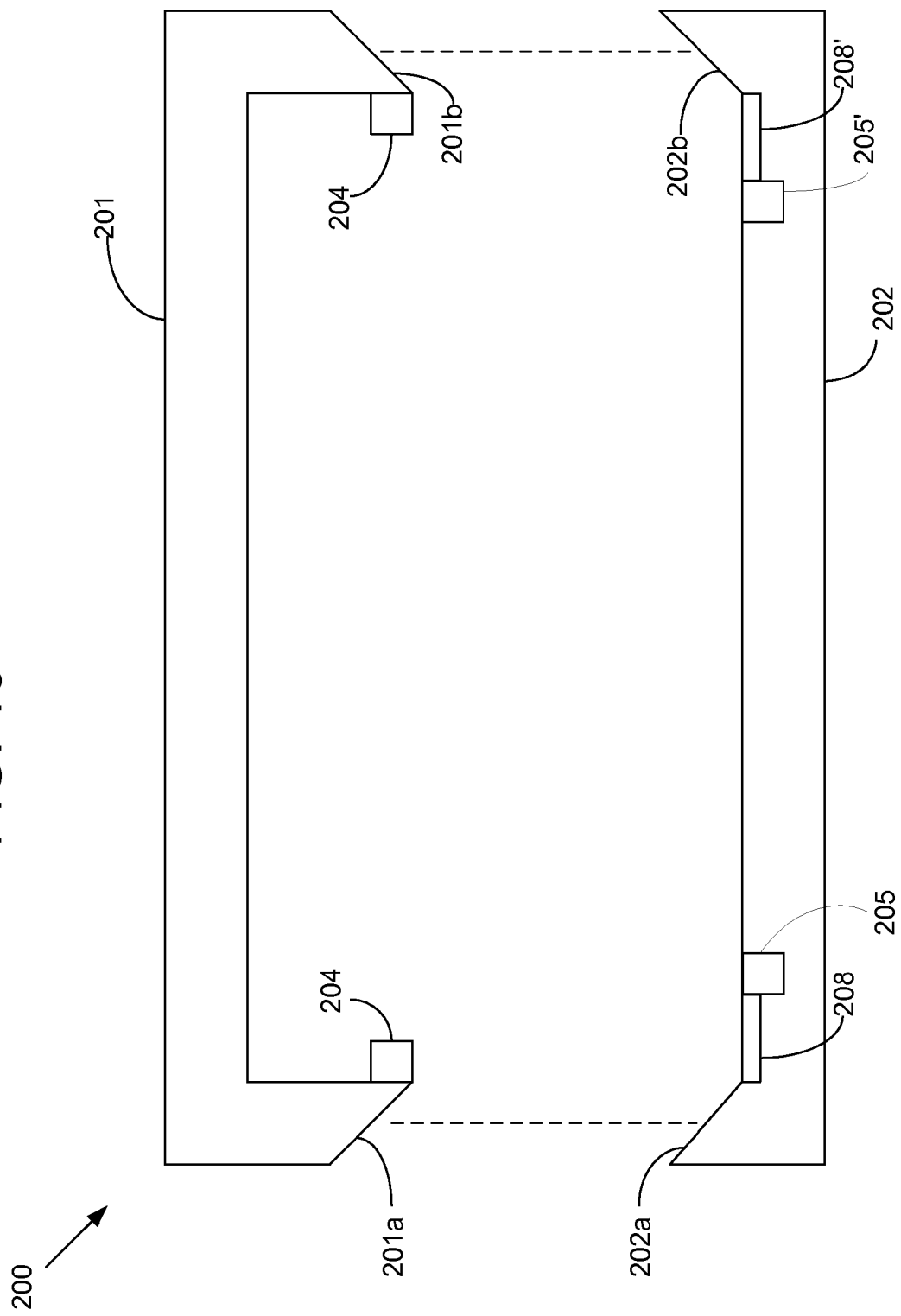
FIG. 19 illustrates a medical device system in accordance with an embodiment of the present invention.

In some embodiments, such as the embodiment exemplified in FIG. 19, the conductive medium 208 may be arranged at a position adjacent the other interactive element (e.g., the sensor 205 in FIG. 19) or otherwise in communication with the other interactive element to allow the conductive medium 208 to function as a conductor for the other interactive element. In further embodiments, the conductive medium 208 may be arranged on its respective part to allow the other interactive element to be interactable with the interactive element (e.g., the first interactive element 204 in FIG. 19) on the opposing part via the conductive medium 208 in any of the manners described in the disclosure.

For example, in particular embodiments, the first interactive element 204 may interact with the conductive medium 208 in a case where the first part 201 and the second part 202 are operatively engaged properly. Accordingly, the first interactive element 204 may be detectable by the sensor 205 via the conductive medium 208. Thus, some embodiments may allow for the sensor 205 to detect the interactive element (e.g., the second interactive element 206) through the conductive medium 208 in addition to or alternative directly detecting the interactive element. For example, an electrical connection between the first interactive element 204 and the conductive medium 208 (e.g., electrically conductive medium) may be established by contacting the conductive medium 208, which may then be detected by the sensor 205.

Thus in various embodiments, as part of a process of assembling a first part 201 and a second part 202 of a medical device system 200, a user may bring the first part 201 and the second part 202 together to operatively engage each other or otherwise be in sufficiently close proximity. Accordingly, an interactive element (e.g., first interactive element 204, second interactive element 206, and/or the like), a sensor 205, and/or an conductive material 208 may interactable with each other to determine, for example, whether the first part 201 and the second part 202 have been operatively engaged properly aligned (e.g., connected and/or aligned).

In various embodiments, the interactive element(s) (e.g., first interactive element 204, second interactive element 206, and/or the like), the sensor(s) 205, and/or the conductive medium 208 need not be used or otherwise limited to two housing portions. FIGS. 20-23 illustrate a medical device system 300 according to various embodiments of the present invention. The medical device system 300 may include features similar or employed as an embodiment of the medical device system 100 (e.g., FIGS. 7-15B), the medical device system 200 (e.g., FIGS. 16-19) and/or other delivery devices discussed in the disclosure. Although the medical device system 300 may include features similar or used with the embodiments of FIGS. 7-19, it should be understood that the medical device system 300 may also include some or all of the same features and operate in a manner similar to that shown and described in the embodiments of FIGS. 1-6C and 24-32B. In addition, some or all of the features shown in FIGS. 1-19 and 24-32B may be combined in various ways and included in the embodiments shown in FIGS. 20-23. Likewise, it should be understood that any of the features of the embodiments of FIGS. 20-23 may be combined or otherwise incorporated into any of the other embodiments of FIGS. 20-23 as well as any other embodiment herein discussed.

As previously described, a first part 301, which may be similar to the first part 101 (and 201) (e.g., FIGS. 7-19), and a second part 302, which may be similar to the second part 102 (and 202) (e.g., FIGS. 7-19), may be two housing portions, such as, but not limited to, a durable housing portion 30 (e.g., FIGS. 1-6C) and a disposable housing portion 20 (e.g., FIGS. 1-6C), as previously described. A third part 303 may be provided that may be, but is not limited to, a base portion 21 (e.g., FIGS. 1-6C). In some embodiments, the conductive medium 308 or further conductive mediums (e.g., electrically conductive medium, magnetically attractive material, such as a yoke, ferrous conduit, thermally conductive material, and/or the like) may be provided on at least one of the parts. This may allow for a connection or interaction between the interactive element(s) (e.g., first interactive element 304, second interactive element 306, and/or the like) and/or the sensor(s) 305.

For example, in the embodiment exemplified in FIG. 20, a conductive medium 308 (e.g., electrically conductive medium, yoke, ferrous conduit, and/or the like) may be provided in a third part 303. A first interactive element 304 may be supported by a first part 301 in a position to interact with the conductive medium 308 of the third part 303 upon the first part 301 being operatively engaged with the third part 303. A sensor 305 may be supported by a second part 302 in a position to interact with the conductive medium 308 of the third part 303 upon the second part 302 being operatively engaged with the third part 303.

Thus in some embodiments, in a case where a first part 301 is operatively engaged with a third part 303 and a second part 302 is operatively engaged with the third part 303, a first interactive element 304 may be detectable by a sensor 305 via a conductive medium 308. In various embodiments, the arrangement of each of the conductive medium 308, the first interactive element 304 (or other interactive elements, such as second interactive element 306, and/or the like), and the sensor 305 need not be limited to the third part 303, the first part 301, and the second part 302, respectively, but may be arranged on any of the components as well as any other components as needed.

Another example as exemplified in FIG. 21, a conductive medium 308' (e.g., electrically conductive medium, yoke, ferrous conduit, and/or the like) may be provided in a third part 303 as well as a first part 301. A first interactive element 304 may supported by a second part 302 in a position to interact with the conductive medium 308' of the third part 303 upon the second part 302 being operatively engaged with the third part 303. A sensor 305 may be supported by the second part 302 in a position to interact with a conductive medium 308 of the first part 301 in a case where each of the first part 301 and the second part 302 is operatively engaged with the third part 303.

Thus in some embodiments, in a case where a first part 301 is operatively engaged with a third part 303 and a second part 302 is operatively engaged with the third part 303, a first interactive element 304 may be detectable by a sensor 305 via a conductive medium 308 and a conductive medium 308'. In various embodiments, the arrangement of each of the conductive medium 308 and 308', the first interactive element 304 (or other interactive elements (e.g., second interactive element 306, and/or the like), and the sensor 305 need not be limited to the exemplified arrangements, but may be arranged on any of the components as well as any other components as needed.

In some embodiments, such as the embodiment exemplified in FIG. 22, more than one sensor, such as a sensor 305 and a sensor 305', may be arranged on one of the parts (e.g., first part 301, and/or the like). Each of the sensor 305 and the sensor 305' may be configured to sense a respective interactive element (e.g., first interactive element 304, second interactive element 306, and/or the like) located on each of the remaining parts (e.g., second part 302, third part 303, and/or the like). Thus in some embodiments, in a case where each of a first part 301 and a second part 302 is operatively engaged with a third part 303, a first interactive element 304 of the third part 303 may be detectable by a sensor 305 (i.e., a first sensor). Similarly, a second interactive element 306 of the second part 302 may be detectable by a sensor 305' (i.e., a second sensor).

In other embodiments, such as the embodiment exemplified in FIG. 23, a sensor 305 may be arranged on one of the parts (e.g., the second part 302, and/or the like) and configured to sense interactive elements (e.g., first interactive element 304, first interactive element 304', second interactive element 306, second interactive element 306', and/or the like), and/or the like arranged on each of the remaining parts (e.g., first part 301, third part 303, and/or the like). Thus in some embodiments, in a case where each of a first part 301 and a second part 302 is operatively engaged with a third part 303, a first interactive element 304 of the third part 303 and a first interactive element 304' of the second part 302 may be detectable by the sensor 305.

With reference to FIGS. 20-23, in various embodiments, arrangement of each of the interactive element(s) (e.g., first interactive element 304 (and/or 304'), second interactive element 306 (and/or 306'), and/or the like), sensor(s) 305 (and/or 305'), and/or conductive medium(s) 308 (and/or 308') need not be limited to the exemplified arrangements. The various interactive element(s), sensor(s), and/or conductive medium(s) may be arranged as needed in any suitable configuration amongst some or all of the components (e.g., first part 301, second part 302, third part 303) as well as any other components (e.g., further parts, such as an needle-inserting device as discussed further below, electronics housing, and/or the like). As a non-limiting example, in FIG. 22, the sensor 305 and the sensor 305' may be arranged on the second part 302, and/or the third part 303, or further part. As another non-limiting example, in FIG. 21, the first interactive element 304 and the sensor 305 may be arranged on the first part 301 and the conductive medium 308 may be arranged on the second part 302 (or any other part) to allow the first interactive element 304 to interact with the sensor 305 through the conductive medium 308 and the conductive medium 308'.

With reference to FIGS. 20-23, in some embodiments, each of the interactive element(s) (e.g., first interactive element 304 (and/or 304'), second interactive element 306 (and/or 306'), and/or the like), sensor(s) 305 (and/or 305'), and/or conductive medium(s) 308 (and/or 308') may be configured and/or arranged on their respective parts such that the components can interact with each other only if the first part 301, the second part 302, and/or the third part 303 (and/or any further part) are operatively engaged properly. For example, in FIG. 21, if while the parts are operatively engaged, the first part 301 is not moved close enough to the second part 302, the conductive medium 308 of the first part 301 may not provide a connection between the first interactive element 304, the conductive medium 308' of the third part 303, and the sensor 305. Thus, in such an example, the first part 301, the second part 302, and the third part 303 have not been operatively engaged properly.

Thus various embodiments may allow for verification between three (or two or more than three) distinct and separate components, verification of correct positioning between three distinct and separate components, verification that three distinct and separate components have been connected in the correct order, a safety mechanism to provide notification of separation (intentional or accidental) of any individual component in a multi-component system, and/or the like.

Although the medical device system 300 may be similar or used with the embodiments of FIGS. 7-19, it should be understood that the medical device system 200 may also include some or all of the same components and operate in a manner similar to that shown and described in the embodiments relating to the medical device system 300. In addition, some or all of the features shown in FIGS. 20-23 may be combined in various ways and included in the embodiment shown in FIGS. 7-19. For instance, although the description relating to FIGS. 20-23 applied to embodiments having three (or more) housing portions, the features relating to the embodiments of FIGS. 20-23 may be used in addition with or in place of those embodiments having two housing portion discussed, for example, with respect to FIGS. 7-19.

FIGS. 24-29B and 48 illustrate a medical device system 400 according to various embodiments of the present invention. The medical device system 400 may include features similar or employed as an embodiment of the medical device system 100 (e.g., FIGS. 7-23), the medical device system 200 (e.g., FIGS. 16-19), the medical device system 300 (e.g., FIGS. 20-23), and/or other medical device system discussed in the disclosure. Although the medical device system 400 may include features similar or used with the embodiments of FIGS. 7-23, it should be understood that the medical device system 400 may also include some or all of the same features and operate in a manner similar to that shown and described in the embodiments of FIGS. 1-6C and 30A-32B. In addition, some or all of the features shown in FIGS. 1-23 and 30A-32B may be combined in various ways and included in the embodiments shown in FIGS. 24-29B and 48. Likewise, it should be understood that any of the features of the embodiments of FIGS. 24-29B and 48 may be combined or otherwise incorporated into any of the other embodiments of FIGS. 24-29B and 48 as well as any other embodiment herein discussed.

The medical device system 400 may include a responsive device 410 configured to provide an electronically detectable state or signal in response to an interaction (or lack thereof) between two or more interactive elements. As previously discussed, an interaction between two or more interactive elements may occur in a case where the first part 401 and the second part 402 are operatively engaged properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first part 401 and the second part 402 for operation. Thus, in some embodiments, the responsive device 410 may be configured to provide a signal in a case where the first part 401 and the second part 402 are operatively engaged (or otherwise in sufficient proximity) and properly aligned. The signal may indicate, for example, the two or more interactive elements have interacted, and thus the first part 401 and the second part 402 have been operatively engaged properly. In some embodiments, the responsive device 410 may be configured to change between a relatively non-detectable state to a detectable state (e.g., electrically detectable state) in response to an interaction between two or more interactive elements.

In some embodiments, the responsive device 410 may be configured to detect the interaction between the two or more interactive elements. In further embodiments, the responsive device 410 may be configured to produce an electronically detectable state or signal in response to the responsive device 410 detecting an interaction between the two or more interactive elements. In other embodiments, a sensor, such as the sensor 205 (or 305) (e.g., FIGS. 16-23) or other electronics may be configured to detect the interaction between the two or more interactive elements or to detect a detectable feature as previously described. In further embodiments, the responsive device 410 may be configured to produce an electronically detectable state or signal in response to the sensor detecting an interaction between the two or more interactive elements.

In some embodiments, such as the embodiment shown in FIG. 24, the responsive device 410, may be configured to provide an electronically detectable state or signal in response to an interaction between two interactive elements, such as a first interactive element 404, which may be similar to the first interactive element 104 (204, and/or 304) (e.g., FIGS. 7-23), and a second interactive element 406, which may be similar to the second interactive element 106 (206, and/or 306) (e.g., FIGS. 7-23). For example, the responsive device 410 may be configured to detect an electrical connection (or lack thereof) between the first interactive element 404, which may be an electrically conductive material, on the first part 401 and a second interactive element, such as an electrical contact, on the second part 402.

Figure 25:
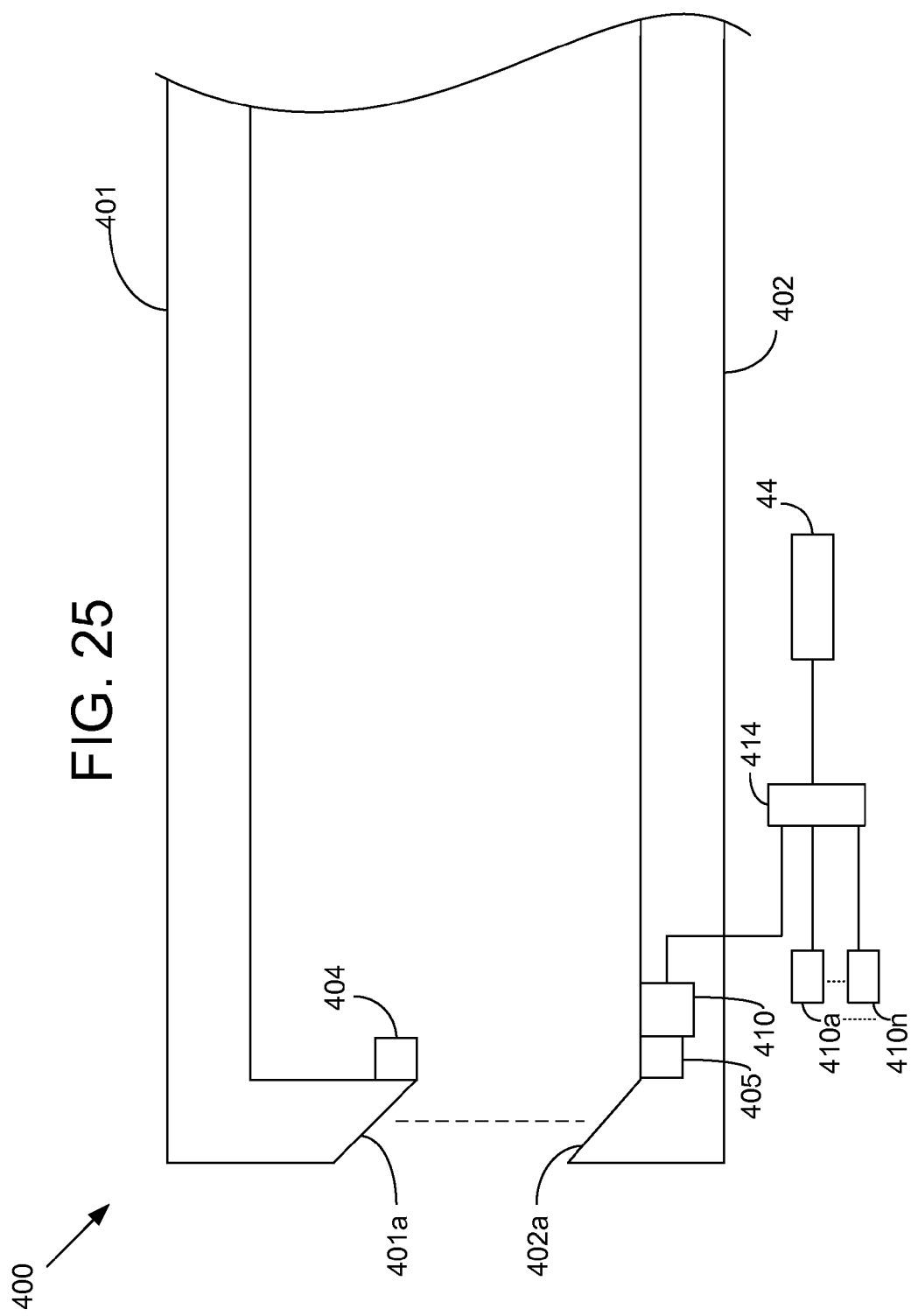
FIG. 25 illustrates a medical device system in accordance with an embodiment of the present invention.

In some embodiments, such as the embodiment shown in FIG. 25, the responsive device 410, may be configured to provide an electronically detectable state or signal in response to an interaction (or lack thereof) between an interactive element or detectable feature (e.g., first interactive element 404) and a sensor 405, for example as described in FIGS. 16-23.

Figure 26:
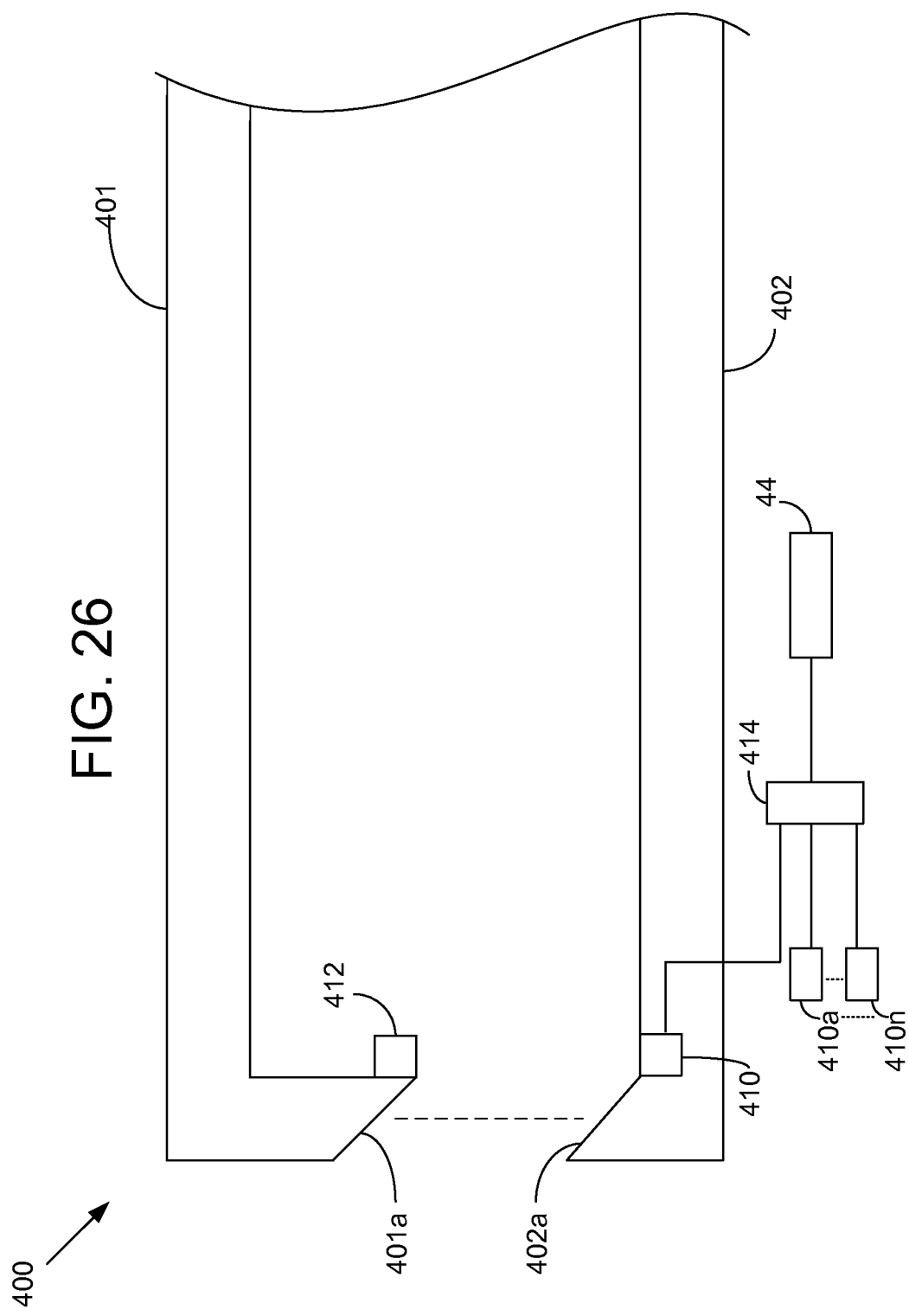
FIG. 26 illustrates a medical device system in accordance with an embodiment of the present invention.

In some embodiments, such as the embodiment shown in FIG. 26, the responsive device 410, may be configured to provide an electronically detectable state or signal in response to an interaction between the responsive device 410 and an interactive element 412, which may be similar to the first interactive element 404 (e.g., FIG. 23) and/or the second interactive element 406 (e.g., FIG. 23). In further embodiments, the responsive device 410 may be an activating switch or the like configured and/or arranged to be activated upon interacting with the interactive element 412. For example, the responsive device 410 may be supported by one or both of the first part 401 and the second part 402 in a position to be activated by the interactive element 412, when the first part 401 and the second part 402 are brought into a pre-defined, sufficiently aligned position and/or in a pre-defined, sufficiently close proximity. The predefined aligned position and/or proximity, for example, may correspond to a properly aligned and mutually proximate position for connection of the first part 401 and the second part 402 for operation.

Figure 28:
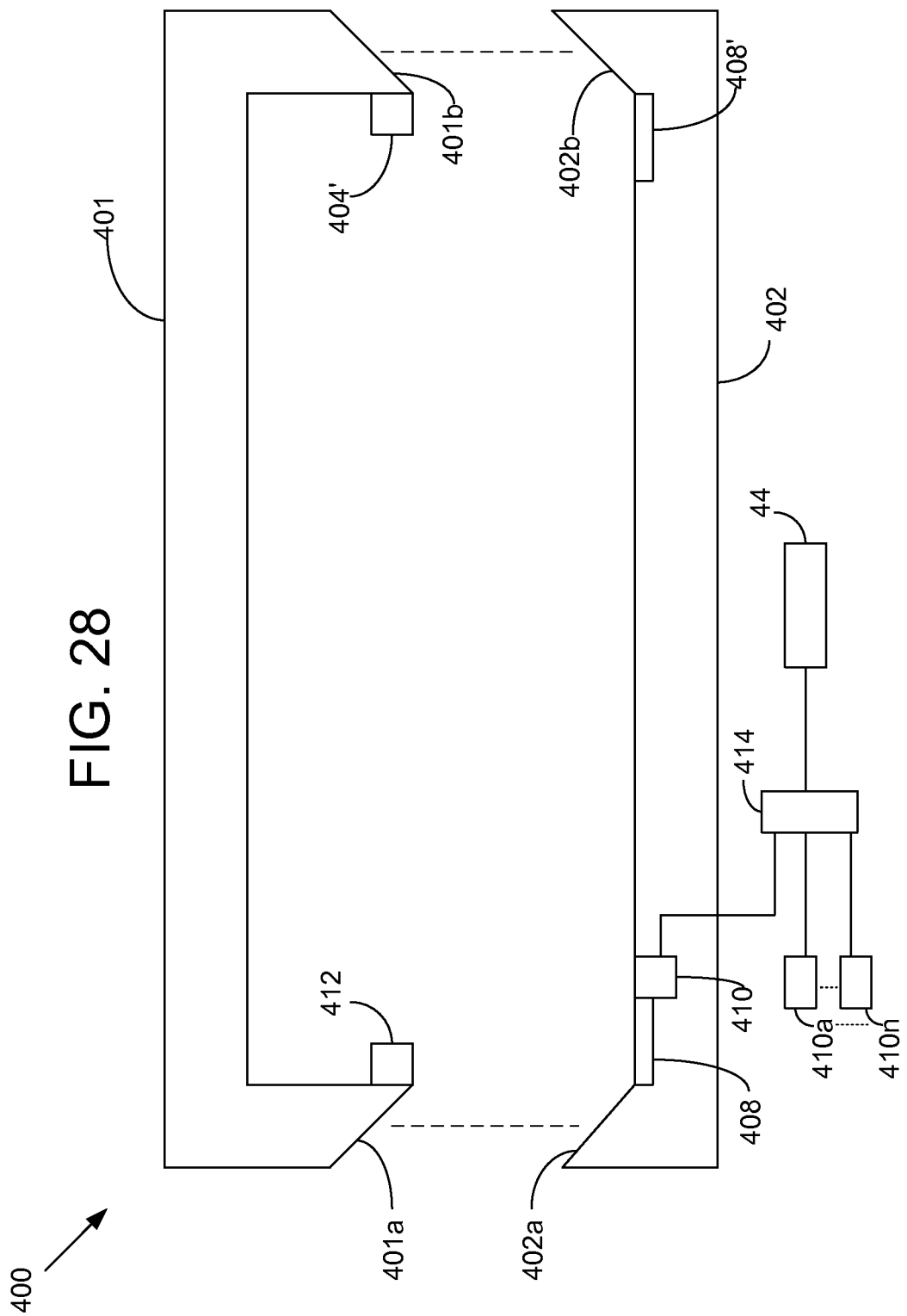
FIG. 28 illustrates a medical device system in accordance with an embodiment of the present invention.

The interactive element 412 may activate the responsive device 410, for example, by contacting the responsive device 410 and/or a part associated with the responsive device 410, such as an electrically conductive material 408 adjacent the responsive device 410 (e.g., FIG. 28). Accordingly, in such embodiments, in a case where the first part 401 and the second part 402 are brought together and the responsive device 410 is activated by the interactive element 412, the responsive device 410 may provide a signal and/or the like indicating that the first part 401 and the second part 402 have been operatively engaged properly. In other embodiments, a similar responsive device 410 may be provided on the first part 401 and an associated interactive element 412 for activating the responsive device 410 may be provided on the second part 402, either in addition to or as an alternative to the arrangement shown in FIG. 26.

Figure 27:
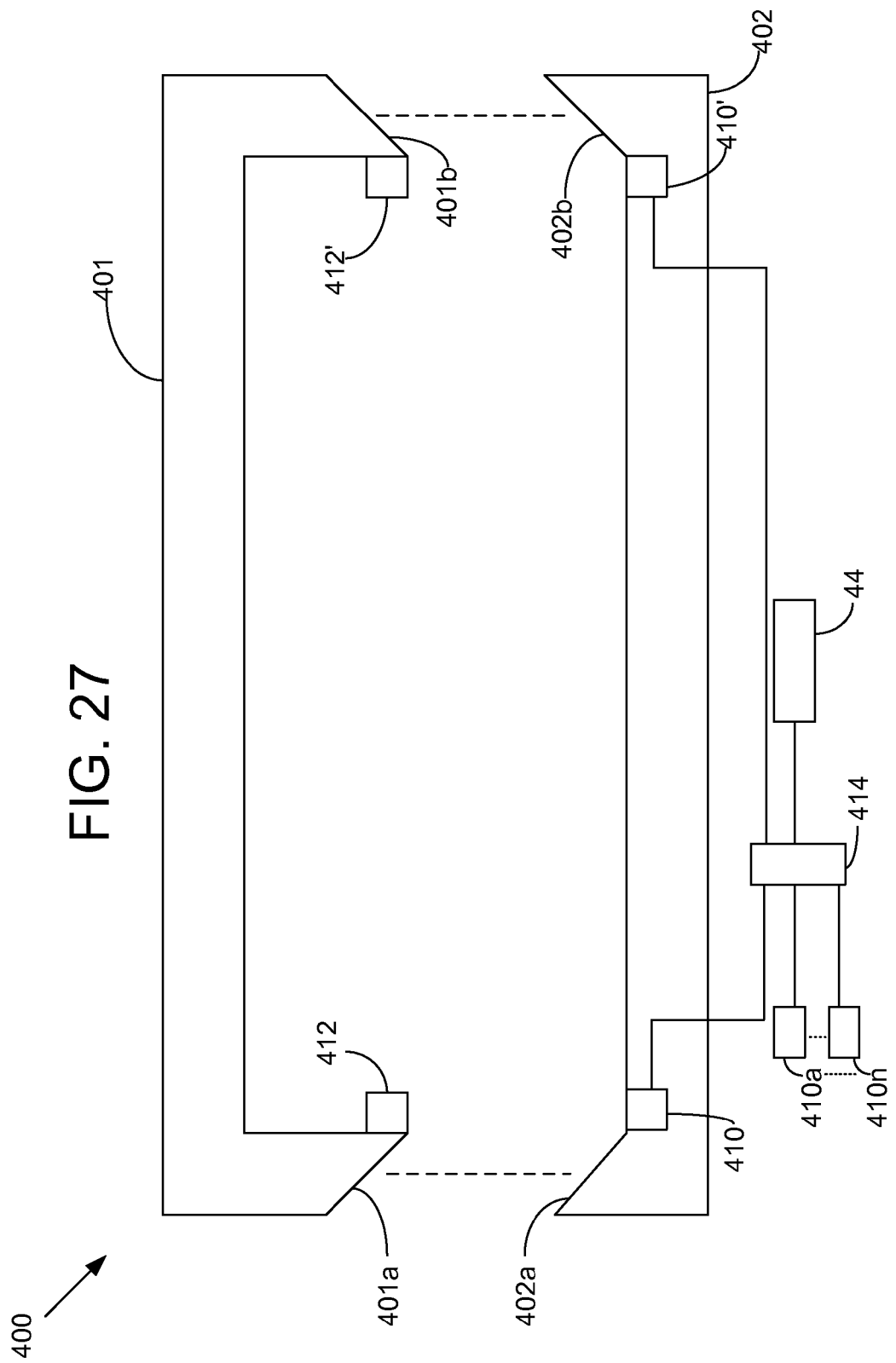
FIG. 27 illustrates a medical device system in accordance with an embodiment of the present invention.

In some embodiments, such as the embodiment exemplified in FIG. 27, multiple responsive devices 410 and 410' and interactive elements 412 and 412' may be provided on the first part 401 and the second part 402 respectively. The interactive element 412', for example, may be similar to or one or more of the first interactive element 104 (204, or 304), the first interactive element 104' (204', or 304'), the second interactive element 106 (206, or 306), the second interactive element 106' (206', or 306'), and/or the like previously described with respect to FIGS. 7-23. Returning to FIG. 27, in other embodiments, multiple responsive devices 410 may be provided with at least one responsive device 410 on each of the first part 401 and the second part 402 for interacting with a respective interactive element 412 on the opposing part. The embodiments described need not be limited to multiple responsive devices 410 and 410' and interactive elements 412 and 412'. Various embodiments may include multiple first interactive elements 404, 404' and second interactive elements 406, 406', as described, for example, with respect to FIG. 24 in addition to or in alternative to the interactive elements 412 and 412' of FIG. 27. Some embodiments may include multiple first interactive elements 404, 404' and sensors 405, 405', as described, for example, with respect to FIG. 25 in addition to or in alternative to the interactive elements 412 and 412' of FIG. 27.

In some embodiments, such as the embodiment exemplified in FIG. 28, an interactive element 412 on the first part 401 (and/or the second part 402) may be arranged to function with a conductive medium 408 on the second part 402 (and/or the first part 401), for example, as previously described with respect to FIGS. 9 and 18-23. With reference to FIG. 28, a responsive device 410 may be located at a position adjacent the conductive medium 408 or otherwise in communication with the conductive medium 408 to allow the conductive medium 408 to function as a conductor for the responsive device 410. The responsive device 410 may be remote from the location of the interactive element 412 on the first part 401. In such embodiments, the interactive element 412 may interact with the conductive medium 408 and thus, interact with the responsive device 410 through the conductive medium 408, for example, to activate the responsive device 410. For example, this may occur in a case where the first part 401 and the second part 402 are brought together for operative engagement and the conductive medium 408 and the interactive element 412 contact each other or otherwise interact with each other.

In some embodiments, a conductive medium 408 may be arranged adjacent to or otherwise in communication with the interactive element 412 to allow the conductive medium 408 to function as a conductor for the interactive element 412, for example, as previously described with respect to FIGS. 9 and 18-23. Returning to FIG. 28, in such embodiments, the interactive element 412 may interact with the conductive medium 408, which may be then interacted with the responsive device 410, for example upon the first part 401 and the second part 402 being operatively engaged. For example, in a case where the interactive element 412 is an electrical contact and the conductive medium 408 is an electrically conductive medium (e.g., copper, aluminum, graphite, and/or the like), the interactive element 412 may energize the conductive medium 408. Thus, an electrical connection may be formed between the interactive element 412 and the responsive device 410 via the conductive medium 408, for example, to activate the responsive device 410 in a case where the first part 401 and the second part 402 are operatively engaged properly.

With reference to FIGS. 24-28, the responsive device 410 may be connected in electrical communication with control electronics 414. The control electronics 414 may be incorporated within the control electronics for controlling a drive device 44 (e.g., FIG. 4) such as, but not limited to, the control electronics 52 (e.g., FIG. 4) for controlling the drive device 44. Alternatively, the control electronics 414 may be separate from and in addition to the control electronics 52, but connected in electrical communication with the control electronics 52 and/or the drive device 44 to provide a drive control signal to the drive device 44. More specifically, the control electronics 414 may be configured to inhibit operation of the drive device 44, unless the responsive device 410 provides a signal or a change in state to the control electronics 414. For instance, as previously discussed, the responsive device 410 may provide such a signal or a change in state upon being activated by the interactive element 412, for example, in a case where the first part 401 and the second part 402 are in proper alignment and sufficiently close in proximity to connect for operation. In other words, the drive device 44 may be inoperable unless the first part 401 and the second part 402 are operatively engaged properly (i.e., aligned and/or connected properly).

In other embodiments, the sensor 205 (305, 405) (e.g., FIGS. 16-28) or electronics associated with the sensor 205 may be connected in electrical communication with control electronics 414 in addition to or in place of the responsive device 410. The control electronics 414 may be configured to inhibit operation of the drive device 44, unless the sensor 205 or electronics associated with the sensor 205 may provides a signal or a change in state to the control electronics 414. For example, as previously discussed, the sensor 205 or electronics associated with the sensor 205 may provide such a signal or a change in state upon detecting an interactive element, for example, in a case where the first part 401 and the second part 402 are in proper alignment and sufficiently close in proximity to connect for operation. In other words, the drive device 44 may be inoperable unless the first part 401 and the second part 402 are operatively engaged properly (i.e., aligned properly).

In some embodiments, the control electronics 414 may provide a detect signal such as, but not limited to an electronic signal, flag setting, or other indicator to the control electronics 52 and/or the drive device 44 upon activation of the responsive device 410 by the interactive element 412. In such embodiments, the control electronics 52 and/or the drive device 44 may be configured to allow operation of the drive device 44 only upon the presence of the detect signal.

As discussed above, in certain embodiments, multiple responsive devices 410 and interactive elements 412 (and/or first interactive element(s) 404, second interactive element(s) 406, sensor(s) 405) may be provided on the first part 401 and the second part 402 and electronically connected to the control electronics 414. In such embodiments, the multiple responsive devices 410 and interactive elements 412 may be located, for example, at different respective positions around or within the first part 401 and the second part 402 to provide multiple alignment readings from different locations. In such embodiments, for instance, the control electronics 414 may be configured to provide a detect signal, for example, to allow operation of the drive device 44 only upon an activation of all or a predefined number or set of the responsive devices 410.

Figure 29A:
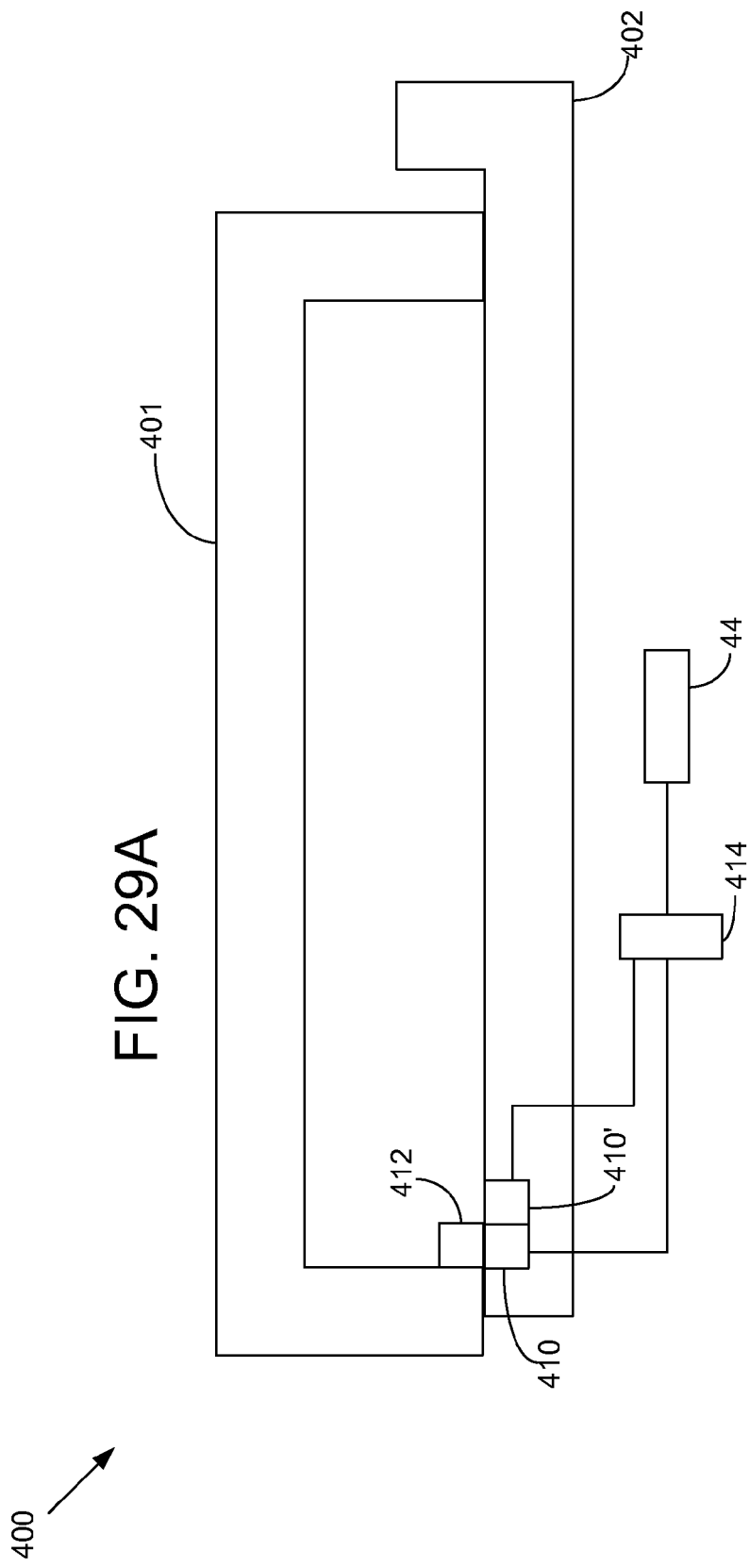
FIG. 29A illustrates a medical device system in accordance with an embodiment of the present invention.

In further embodiments, the control electronics 414 may be configured to provide a detect signal, for example, to allow operation of the drive device 44 only upon an activation of all or a predefined number or set of the responsive devices 410 in a particular order. For example, the control electronics 414 may be configured to provide a detect signal only if a first responsive device is activated before, after, or simultaneously with a second responsive device. In the embodiments exemplified in FIGS. 29A and 29B, first, the first part 401 and the second part 402 may be connected so that the interactive element 412 aligns, activates, or otherwise interacts with a first responsive device 410 as shown in FIG. 29A. Then the first part 401 may be moved relative to the second part 402 to align the interactive element 412 with a second responsive device 410' shown in FIG. 29B. Such embodiments may allow, for example, for connection of components in a particular sequence, orientation, and/or in a particular direction.

With reference to FIGS. 24-29B, the control electronics 414 and/or the control electronics 52 (e.g., FIG. 4) may be configured to control the drive device 44 (e.g., FIG. 4) in various manners in accordance with various embodiments of the invention. For example, the drive device 44 may be controlled to stop pumping (delivery) operation upon a detection of an interruption of a fluid-flow path or a disconnection of a critical component in the delivery device 400. These may include, but are not limited to, a disconnection of a housing portion from another housing portion or from a base portion, a disconnection of a conduit from another conduit or from a reservoir, a disconnection of a reservoir from a housing portion or a base, and/or the like.

In alternative or in addition, the control electronics 414 and/or the control electronics 52 (e.g., FIG. 4) may be configured to detect a first-time connection of the first part 401 and the second 402 or a first-time connection of other components, as compared to a re-connection after previous or partial usage. In this manner, the drive device 44 may be controlled to provide a priming operation or other suitable first-time operation(s) upon detection of a first-time connection of the first part 401 and the second part 402.

In yet further embodiments, additional sensors and/or responsive devices 410*a*-410*n* may be provided within the medical device system 400 and connected for electrical communication with the control electronics 414. Such additional sensors and/or responsive devices 410*a*-410*n* may comprise magnetically and/or electronically actuating switches, magnetic and/or electric field magnitude and direction sensors, inductive sensors, other proximity sensors, contact sensors, and/or the like for providing a detectable signal or change in a state upon proper connection of other components in the medical device system 400. In some embodiments, such additional sensors and/or responsive devices 410*a*-410*n* may be similar to the sensor 205 (or 305) (e.g., FIG. 16-23) previously described. Such proper connection of other components may comprise, for example, one or more of a proper connection of a reservoir into a housing portion or base, a proper connection of a conduit to a reservoir, a proper connection of two conduits together, a proper setting of a needle or cannula in an inserted state, a proper connection of a conduit to a cannula or needle, or a proper connection of other components of or to the medical device system 400.

Alternatively, or in addition, the additional sensors and/or responsive devices 410*a*-410*n* may include one or more flow detectors for detecting the occurrence or blockage of a fluid flow path in the infusion device. In such embodiments, the control electronics 414 may be configured to provide a detect signal, for example, to allow operation of the drive device 44 only upon an activation of all or a predefined number or set of the responsive devices 410 and a proper state of the additional sensors and/or responsive devices 410*a*-410*n*.

Figure 48:
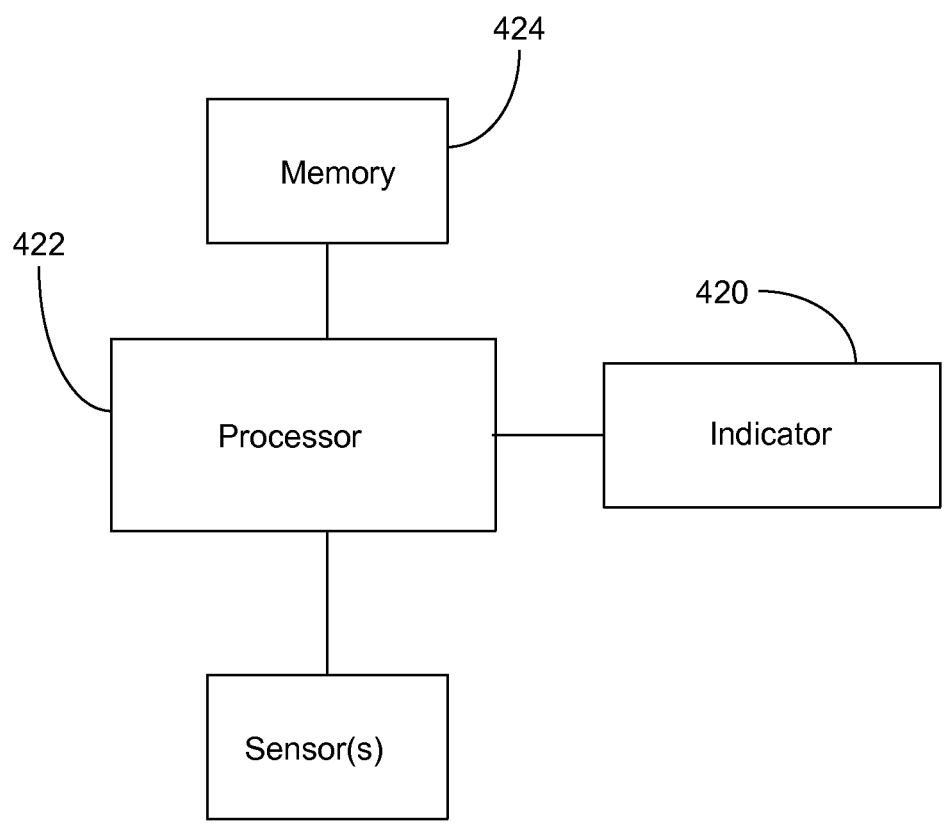
FIG. 48 illustrates a block diagram of an electrical configuration of a medical device system in accordance with an embodiment of the present invention.

In alternative or in addition, the control electronics 414 and/or the control electronics 52 (e.g., FIG. 4) may be configured to provide a user-perceptible indication of a proper alignment and/or connection of the first part 401 and the second part 402 or of other components. These may include, but are not limited to, the connection of a reservoir to a housing portion 401 or the connection of an injection site module to one or both of the first part 401 and the second part 402, and/or the like. For example, upon detection of a proper alignment and/or connection of the first part 401 and the second part 402, the control electronics 414 or 52 may provide a suitable control signal to activate an indicator device 420, as shown in FIG. 48.

The indicator device 420 may be operated by a processor 422. The processor 422 may be configured to execute various programs and/or to process various information, such as data received from one or more sensors, responsive devices, and/or other interactive elements. The processor 422, for example, may be configured to compare detected signals with thresholds and/or pre-stored values in memory 424.

With reference to FIGS. 24-29B and 48, the indicator device 420 may include, but is not limited to, an audible indicator, an optical indicator, a tactile indicator, combinations of one or more those indicators, and/or the like. For example, upon a proper alignment or connection of components as described above, an audible beeping sound or other suitable sound may be generated by a sound generating device in or associated with one or both of the first part 401 and the second part 402. For example, upon a proper alignment or connection of components as described above, a flashing light or other suitable visual indicator may be generated by an LED or other light source or a display device on or associated with one or both of the first part 401 and the second part 402. For example, upon a proper alignment or connection of components as described above, a vibration and/or the like may be generated by a vibration device and/or the like in or associated with one or both of the first part 401 and the second part 402.

In some embodiments, one or more signals may be communicated from a transmitter (not shown) in one of the first part 401 and the second part 402 to a remotely located communication device (not shown), such as, but not limited to, a hand-held controller, a computer, and/or the like. Accordingly, the transmitter may provide one or more of the above-noted user-perceptible indications to a user of the communication device. In some embodiments, a text or graphic message may be displayed on a display screen on one of the first part 401, the second part 402, and/or on the communication device as an indicator of a proper or improper alignment or connection of the first part 401 and the second part 402.

With reference to FIGS. 1-29B, in various embodiments, a connection structure may be provided to secure the first part (e.g., 101, 201, 301, 401) and the second part (e.g., 102, 202, 302, 402) together for operation of the medical device system (e.g., 100, 200, 300, 400) Other examples of connection structures are disclosed in the disclosure. Further examples are disclosed in, but not limited to, U.S. patent application Ser. Nos. 11/759,725, entitled "Infusion Medium Delivery Device and Method with Drive Device for Driving Plunger in Reservoir; Ser. No. 12/553,038, filed Sep. 2, 2009, entitled "Insertion Device Systems and Methods"; U.S. patent application Ser. No. 12/650,378, filed Dec. 30, 2009, all of which are herein incorporated by reference in their entirety.

In further embodiments, the connection structure may include a magnetic structure for connecting the first part and the second part. For example, a magnet may be provided on one of the first part and the second part and a magnetically attractive material, such as a magnet of opposite polarity, a metal, and/or the like may be provided on the other of the first part and the second part. Such an example as well as other examples are disclosed in, but are not limited to, U.S. patent application Ser. No. 11/759,725, entitled "Infusion Medium Delivery Device and Method with Drive Device for Driving Plunger in Reservoir," herein incorporated by reference in its entirety.

Various embodiments, additionally or alternatively, may include other suitable structural features to aid in connecting the first part and the second part. These may include, but are not limited to, adhesives, snap-fit structures, friction-fit structures, and/or the like on the first part and/or the second part that abut as the first part and the second part are brought together for connection. Other examples of various connection structures can be found, but are not limited to, U.S. patent application Ser. No. 12/553,038, filed Sep. 2, 2009, entitled "Insertion Device Systems and Methods," herein incorporated by reference in their entirety.

Further examples of connection and/or alignment structures are described with reference to FIGS. 30A-40B, wherein a medical device system 500 may incorporate two parts: a first housing portion 530 and a second housing portion 550. Other embodiments may include medical device systems with more than two parts.

The medical device system 500 may include features similar or may be employed as an embodiment of the medical device system 100 (e.g., FIGS. 7-23), the medical device system 200 (e.g., FIGS. 16-19), the medical device system 300 (e.g., FIGS. 20-23), the medical device system 400 (e.g., FIGS. 24-29B), and/or any of the other embodiments described in the disclosure. Although the medical device system 500 may include features similar or used with the embodiments of FIGS. 7-29B, it should be understood that the medical device system 500 may also include some or all of the same features and operate in a manner similar to that shown and described in the embodiments of FIGS. 1-6C and/or any of the other embodiments described in the disclosure (e.g., FIGS. 41A-47C). In addition, some or all of the features shown in FIGS. 1-29B (and/or any of the other embodiments described in the disclosure) may be combined in various ways and included in the embodiments shown in FIGS. 30A-40B. Likewise, it should be understood that any of the features of the embodiments of FIGS. 30A-40B may be combined or otherwise incorporated into any of the other embodiments of FIGS. 30A-40B as well as any other embodiment herein discussed.

In various embodiments, the first housing portion 530 may correspond to the first part (e.g., 101, 201, 301, and 401 in FIGS. 7-29B) and the second housing portion 550 may correspond to the second part (e.g., 101, 201, 301, and 401 in FIGS. 7-29B). In particular embodiments, the first housing portion 530 may be similar to the durable portion 30 (e.g., FIGS. 1-6C) and may include (i.e., be integrated with) or be connected with the disposable portion 20 (e.g., FIGS. 1-6C). As previously discussed with respect to FIGS. 1-6C, the durable housing portion 530 may include various components, such as, but not limited to, a drive device 80, drive motor 84, drive device linkage portion 82, and/or the like. The disposable housing portion 20, which may be integrated or connected with the first housing portion 530 may include various components, such as, but not limited to, a reservoir system 40.

Returning to FIGS. 30A-40B, in particular embodiments, the second housing portion 530 may be similar to the base (e.g., 21 in FIGS. 1-6C) that may be securable to skin of a patient-user during operation of the medical device system 500. The second housing portion 550 may include (i.e., be integrated with) or be connected with an injection site section 503. Examples of injection site sections or modules are described in, but are not limited to, U.S. patent application Ser. No. 12/553,008, filed Sep. 2, 2009, entitled "Insertion Device Systems and Methods" and U.S. patent application Ser. No. 12/650,378, filed Dec. 30, 2009, both of which are herein incorporated by reference in their entirety.

The first housing portion 530 may be for securing to the second housing portion 550 and/or the injection site section 503 of the second housing portion 550. In some embodiments, the second housing portion 550 may be secured to the skin of the patient-user before the first housing portion 530 is secured to the injection site section 503 and the second housing portion 550. In further embodiments, the first housing portion 530 may be secured to the second housing portion 550 and/or the injection site section 503 of the second housing portion 550 before the second housing portion 550 is secured to the skin of the patient-user.

The second housing portion 550 may include or be connected with a receptacle structure 510 for receiving fluidic media from a reservoir (e.g., reservoir system 40 in FIGS. 1-6C). Various examples of receptacle structures as well as connection structures for connecting two or more housing portions are described in, but are not limited to, U.S. patent application Ser. No. 12/553,008, filed Sep. 2, 2009, entitled "Insertion Device Systems and Methods," herein incorporated by reference in their entirety. In some embodiments, the receptacle structure 510 may be part of the second housing portion 550 adjacent a section of the second housing portion 550 containing the injection site section 503. In other embodiments, the receptacle structure 510 may include a housing connected or integrated with the second housing portion 550. In such embodiments, the receptacle structure 510 may be separate and apart from the injection site section 503 or adjacent the injection site section 503. In some embodiments, the injection site section 503 may be located on a different housing and connected, for example, with the receptacle structure via a tubing or other fluid conduit.

The second housing portion 550 may include a fluid conduit 524. The fluid conduit 524 may be (or in fluid communication with), but is not limited to, a needle, cannula, a piercing member, and/or the like. The fluid conduit 524 may provide a fluid passage from the receptacle structure 510 to the injection site section 503. The fluid conduit 524 may be supported by a supporting structure located within the receptacle structure 510. In some embodiments, the supporting structure may be a wall integral with the receptacle structure 510. In other embodiments, the supporting structure may be any suitable structure that is generally fixed relative to the receptacle structure 510 and is able to support the fluid conduit 524 in a generally fixed relation to the receptacle structure 510.

Figure 33:
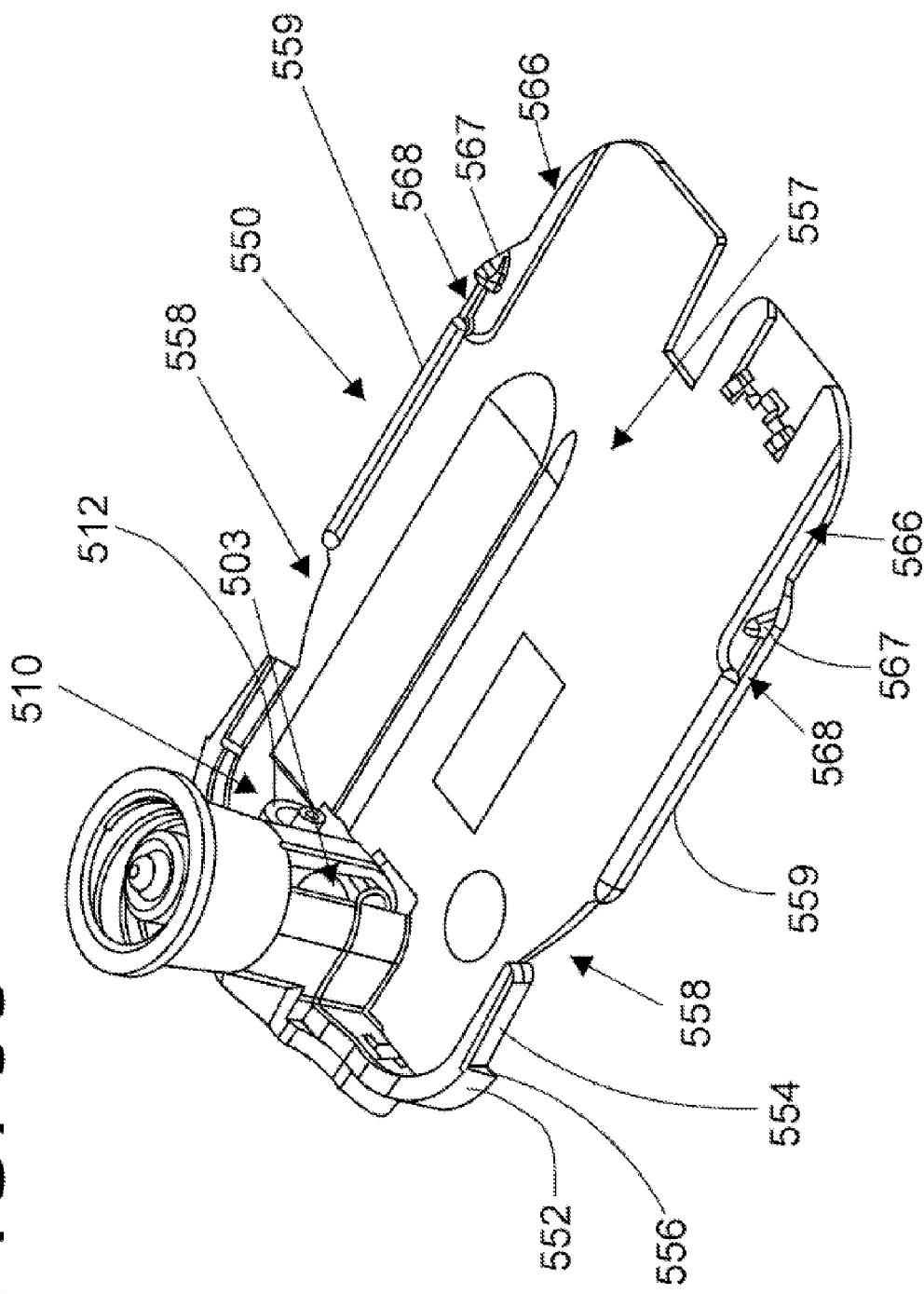
FIG. 33 illustrates a portion of a medical device system in accordance with an embodiment of the present invention.

The fluid conduit 524 may be arranged in any suitable manner to convey fluid, for example, from a reservoir to/from the patient-user. In FIGS. 33 and 34, the fluid conduit 524 is arranged to bend around a portion of the injection site section 503. As such, in various embodiments, the fluid conduit 524 may be provided on the second housing portion 550 in any suitable manner, including as a straight fluid conduit, a curved fluid conduit, or the like.

With reference to FIGS. 30A-34, the fluid conduit 524 may be made of any suitably rigid material, including, but not limited to metal, plastic, ceramic, composite materials, glass, or the like, and may have a hollow channel extending in a lengthwise dimension of the fluid conduit 524. The hollow channel in the fluid conduit 524 may be open at a location 524a along the lengthwise dimension of the fluid conduit 524, such as, but not limited to, a first end of the fluid conduit 524. The hollow channel in the fluid conduit 524 may be open at another location 524b along the lengthwise dimension of the fluid conduit 524, such as, but not limited to, a second end of the fluid conduit 524 opposite the first end of the fluid conduit 524. In some embodiments, the opening 524b of the fluid conduit 524 may be connected in fluid flow communication the injection site section 503.

In some embodiments, one or more of the openings in the fluid conduit 524 may be provided with a septum 526 that may be pierceable, for example, by a sharp end (e.g., 524b) of the fluid conduit 524. In such embodiments, the sharp end may be directed toward a surface of the septum 526 such that the septum 526 may be urged by the first housing portion 530 having a reservoir against the sharp end as the first housing portion 530 is connected to the second housing portion 550. The septum 526 may be made of any suitable material that may be pierceable by a needle (or the like), such as, but not limited to, a natural or synthetic rubber material, silicon, or the like. In some embodiments, the septum 526 may be made of a self-sealing material capable of sealing itself after a fluid conduit (and/or the like) has pierced the septum 526 and was subsequently withdrawn from the septum 526.

In some embodiments, a septum may be provided with the reservoir. The septum may be similar to the septum 526. The septum may be pierceable by a sharp end (e.g., 524b) of the fluid conduit 524. In such embodiments, the sharp end may be directed toward a surface to allow the sharp end to pierce the septum as the first housing portion 530 is connected to the second housing portion 550.

The injection site section 503 may include a channel 540 extending through the second housing portion 550. The channel 540 may have an open end 540a on a bottom surface of the second housing portion 550 (i.e., a surface for contacting skin of the user-patient). The channel 540 may have another open end 540b at an upper surface of the injection site section 503 (i.e., a surface opposite the surface for contacting the skin of the user-patient). The channel 540 may have an opening 540c for allowing the fluid conduit 524, for example via opening 524b, to be in fluid flow communication with the channel 540.

The channel 540 may include a channel section 542 having a suitable shape and size to receive an insert structure, a needle, and/or a cannula, such as those described in U.S. patent application Ser. No. 12/553,008, filed Sep. 2, 2009, entitled "Insertion Device Systems and Methods"; U.S. patent application Ser. No. 11/645,435, filed Dec. 26, 2006, titled "Infusion Medium Delivery system, Device And Method With Needle Inserter And Needle Inserter Device And Method"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety.

Other examples of various insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Further examples of various insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," U.S. Pat. Pub. No. US 2007/0142776, entitled "Insertion Device for an Insertion Set and Method of Using the Same," all of which are herein incorporated by reference in their entirety.

The first housing portion 530 may support a reservoir housing 508, which may be similar to or include reservoir system 40 (e.g., FIGS. 1-6C) or the like as previously described. The reservoir housing 508 of the first housing portion 530 may include a connection portion 531, which is some embodiments may be a port portion of the reservoir housing 508. The connection portion 531 of the reservoir housing 508 may have a suitable shape and size to fit at least partially within an opening 512 of the receptacle structure 510 in the second housing portion 550 when the second housing portion 550 and the first housing portion 530 are connected together.

Figure 31A:
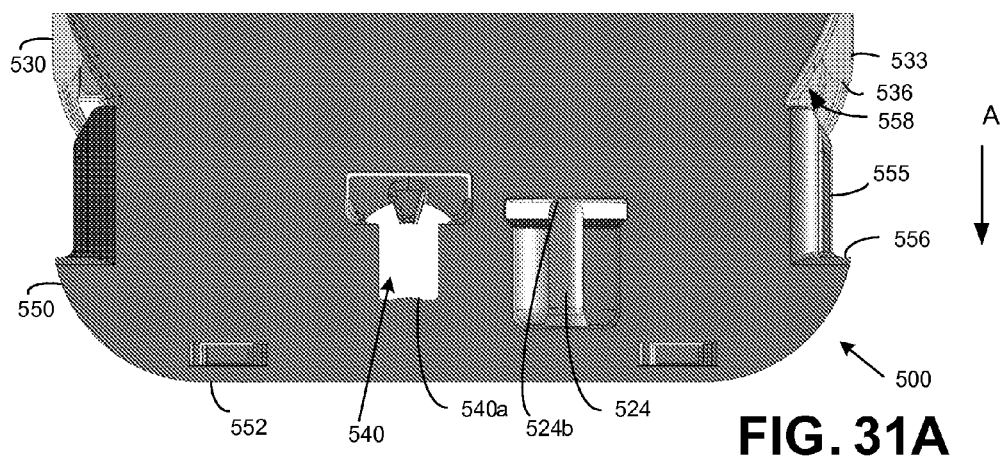
FIGS. 31A-31C illustrate a bottom down view of a portion of a medical device system in accordance with an embodiment of the present invention.
Figure 31B:
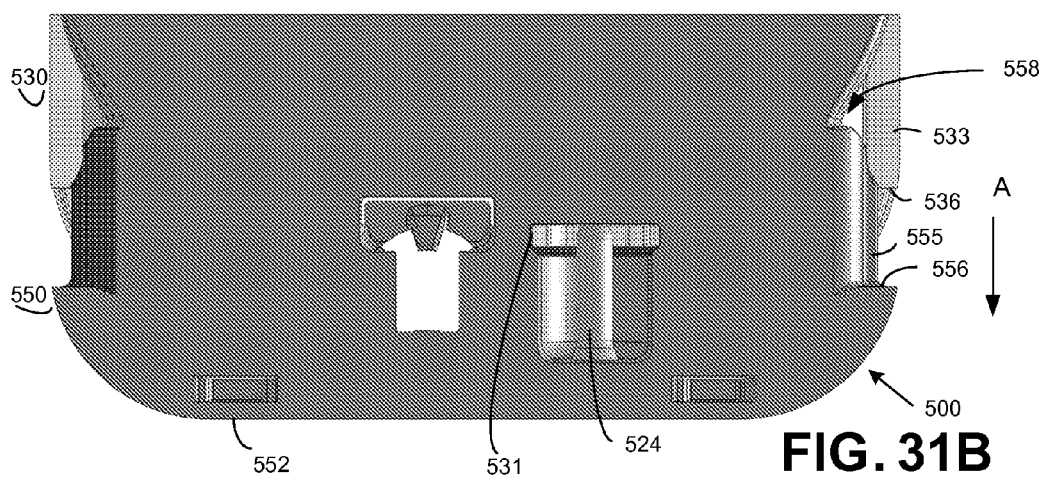

In the drawings of FIGS. 30A, 31A, and 32A, the second housing portion 550 and the first housing portion 530 are shown in a partially separated, disconnected relation, wherein the connection portion 531 of the reservoir housing 508 is outside of the opening 512 of the receptacle structure 510. By moving or sliding the first housing portion 530 in a direction A relative to the second housing portion 550 to bring the first housing portion 530 and the second housing portion 550 together, the connection portion 531 of the reservoir housing 508 can be inserted into the opening 512 of the receptacle structure 510 of the second housing portion as shown in FIG. 31B. Continued relative movement of the second housing portion 550 and the first housing portion 530 together may cause the fluid conduit 524 to extend into the reservoir housing 508 as shown in FIG. 32C. In some embodiments, the continued relative movement of the second housing portion 550 and the first housing portion 530 together may cause a sharp end (e.g., 524b) of the fluid conduit 524 to pass through one or more septa in the receptacle structure 510 and/or the reservoir housing 508.

Returning to FIGS. 30A-34, thus when the second housing portion 550 and the first housing portion 530 are brought together (e.g., FIGS. 30C, 31C, 32C) such that the first housing portion 530 is moved to a position P, at least a portion of the connection portion 531 may extend inside of the receptacle structure 510 with the fluid conduit 524 extending into the interior volume of the reservoir housing 508. Accordingly, the fluid conduit 524 may form a fluid flow path between the interior volume of the reservoir housing 508 and the injection site section 503 or other structure at the opening 524b of the fluid conduit 524. In addition or alternatively, the second housing portion 550 may be slidable in the direction A relative to the first housing portion 530 to bring the two components together.

The receptacle structure 510 and the connection portion 531 may be provided with mating connectors that provide, for example, a snap or friction connection upon the second housing portion 550 and the first housing portion 530 being connected. In some embodiments, the mating connectors may include a protrusion (not shown) on one or the other of the receptacle structure 510 and the connection portion 531. The other of the receptacle structure 510 and the connection portion 531 may include a groove or indentation (not shown) arranged to engage each other in a snap-fitting manner upon the connection portion 531 being extended into the receptacle structure 510 a suitable distance.

In various embodiments, the second housing portion 550 and the first housing portion 530 may be configured to be attachable to and detachable from each other, and in specific embodiments to be slidable relative to each other to operatively engage and disengage each other. That is, the first housing portion 530 may be slidable in the direction A relative to the second housing portion 550 to connect the two components (e.g., the first housing portion 530 is in the position P). Similarly, the first housing portion 530 may be slidable in a second direction, opposite the direction A, relative to the second housing portion 550 to disconnect the two components.

In further embodiments, sliding the first housing portion 530 in the direction A may allow the reservoir housing 508 of the first housing portion 530 to operatively engage the fluid conduit 524 of the second housing portion 550. Thus in some embodiments, a sliding motion, for example in the direction A, for connecting the first housing portion 530 to the second housing portion 550 may be the same sliding motion for connecting the reservoir housing 508 of the first housing portion 530 to the fluid conduit 524 of the second housing portion 550. Accordingly, some embodiments may allow for the first housing portion 530 and the second housing 550 to be connected and the fluid conduit 524 and the reservoir housing 508 to be connected in a single movement. Such embodiments may facilitate engagement of the reservoir housing 508 by the fluid conduit 524.

With reference to FIGS. 30A-34, in some embodiments, the second housing portion 550 may include at least one arm 554, rail, or other raised surface that may be used to facilitate connecting (or removal of) the first housing portion 530 and the second housing portion 550 in a sliding motion. In further embodiments, the arm 554 may include a tab 555 fixedly attached or otherwise extending in a cantilevered manner from the arm 554. The arm 554 and the tab 555 may be used to align the second housing portion 550 and the first housing portion 530 while connecting the two components, as will be further described. Furthermore, the arm 554 and the tab 555 may be used to lock the first housing portion 530 to the second housing portion 550, for example, to inhibit separation of the first housing portion 530 from the second housing portion 550 in an axial direction transverse to the direction A. Thus, the arm 554 and the tab 555 may prevent the first housing portion 530 from falling off or being pulled off the second housing portion 550. Accordingly, in various embodiments, these components provide a coarse horizontal and/or vertical engagement of the first housing portion 530 and the second housing portion 550 toward the front end of the housing portions.

The first housing portion 530 may include at least one groove, cutout, depression, spacing, aperture, and/or the like to facilitate connection between the second housing portion 550 and the second housing portion 550. For example, the first housing portion 530 may include an inner depression 534 for accepting a tab (e.g., tab 555) or other extended member disposed on the second housing portion 550.

In some embodiments, to connect the second housing portion 550 and the first housing portion 530 together, a tab 534 on the first housing portion 530 may be placed in a depression 558 in the second housing portion 550 as shown in FIGS. 30A, 31A, and 32A. The depression 558 may be sized liberally, for example larger than a size of the tab 534, so that the tab 534 may be easily positioned within the depression 558. The tab 534 may be fixedly attached or otherwise extending from the arm 532 of the first housing portion 530.

Figure 31C:
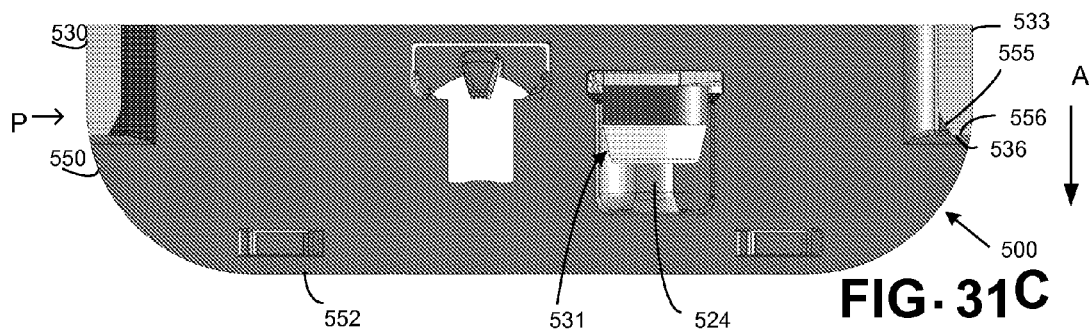

Once the tab 534 and the arm 534 are in the depression 538, the first housing portion 530 may be slid relative to the second housing portion 550 in the direction A. By doing so, the tab 555 on the arm 554 on the second housing portion 550 may slide into the inner depression 534 of the first housing portion 530. Continued relative movement of the second housing portion 550 and the first housing portion 530 may allow the tab 555 to slide along the inner depression 534 and the adjacent tab 534 of the first housing portion 530 as shown in FIGS. 30B, 31B, and 32B. As such, the reservoir supported by the first housing portion 530 may be slid or otherwise moved toward the fluid conduit 524 of the second housing portion 550 to allow the fluid conduit 524 to engage the interior volume of the reservoir housing 508 as shown in FIGS. 30C, 31C, 32C.

Thus, in some embodiments, the second housing portion 550 and the first housing portion 530 may be operatively engaged and the reservoir housing 508 and the fluid conduit 524 may be operatively engaged in one motion. In other words, a motion (e.g., sliding motion in the direction A) for engaging the first housing portion 530 to the second housing portion 550 may the same motion as a motion for engaging the fluid conduit 524 to the reservoir. In further embodiments, engagement of the tab 555 of the second housing portion 550 and the tab 533 of the first housing portion 530 may inhibit separation of the second housing portion 550 and the first housing portion 530 in an axial direction transverse to the direction A.

In addition or alternatively, the second housing portion 550 may be provided with an arm having a tab and/or depression for receiving an arm and/or tab of the first housing portion 530 as previously described. Accordingly, when the first housing portion 530 and the second housing portion 550 are slid relative to each other, for example, in the direction A, the first housing portion 530 and the second housing portion 550 may be operatively engaged in a manner as previously described.

In further embodiments, the second housing portion 550 may be provided with a stop surface 556 to prevent further movement of the first housing portion 530 relative to the second housing portion 550, for example, after the fluid conduit 524 has sufficiently engaged the interior volume of the reservoir housing 508 (e.g., the first housing portion is moved to position P). For instance, a portion of the first housing portion 530 may contact the stop surface 556 after the first housing portion 530 has been sufficiently advanced to substantially prevent the first housing portion 530 from further advancement. Such embodiments, may allow for additional protection of the reservoir housing 508 and/or the fluid conduit 524 from damage due to excessive force, speed, and/or the like in connecting the second housing portion 550 and the first housing portion 530. In other embodiments, a stop surface 536 may be provided on the first housing portion 530 in addition or in alternative to the stop surface 556 of the second housing portion 550.

In some embodiments, the arm 532 and/or other portion of the first housing portion 530 may include a cutout, depression, or surface (not shown) that may aid a user-patient in gripping the first housing portion 530 during the connection process. In some embodiments, a portion of the second housing portion 550 may include a cutout, depression, or surface (not shown) that may aid a user-patient in gripping the second housing portion 550 during the connection process.

With reference to FIGS. 35A-36B, in some embodiments, a dovetail connection structure may be provided for connecting the first housing portion 530 and the second housing portion 550. Accordingly, the dovetail connection structure may provide fine vertical alignment between the first housing portion 530 and the second housing portion 550 at the rear of the housing portions. For example, one of the first housing portion 530 and the second housing portion 550 may have a groove 562 for receiving a protruding surface or dovetail 542 on the other of the first housing portion 530 and the second housing portion 550. A portion of the dovetail 542 may be placed in the groove 562 or slid into the groove 562. Further movement (e.g., in a sliding motion) of the dovetail 542 in the direction A along the groove 562 may connect the first housing portion 530 and the second housing portion 550 in a manner previously described. In some embodiments, the groove 562 and/or the dovetail 542 may be tapered to facilitate placement of the dovetail 542 in the groove 562.

Figure 35A:
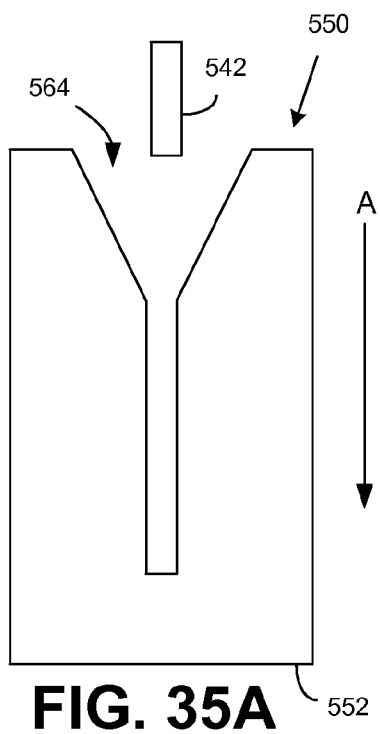
FIGS. 35A and 35B illustrate a portion of a medical device system in accordance with an embodiment of the present invention.
Figure 35B:
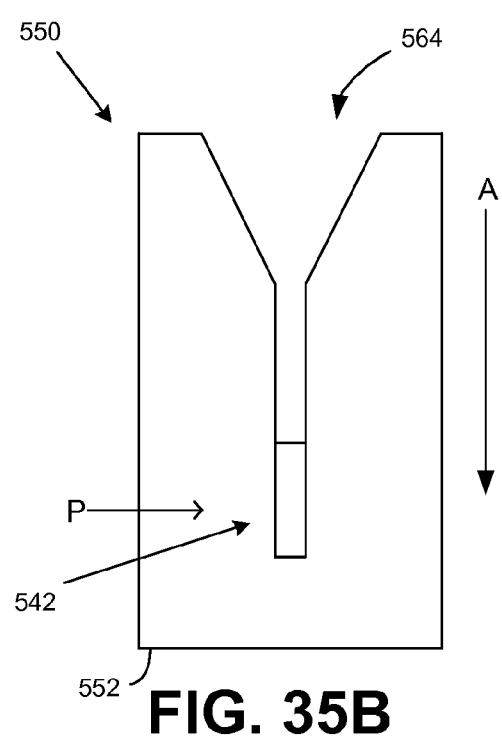

In some embodiments, the groove 562 or the dovetail 542 may be tapered to secure the dovetail 542 in the groove 562, for example, in a friction fit as the dovetail 542 is advanced along the groove 562 in the direction A. For example, as shown in FIGS. 35A and 35B, a width dimension of a groove 564 may be largest opposite the front end 552 of the second housing portion 550 and may taper to a narrow width dimension in a direction of the direction A. Accordingly, such embodiments may allow for facilitating placement of the dovetail 542 in the groove 564, aligning of the first housing portion 530 as the dovetail 542 is guided by a surface defining the groove 564, and/or securing the dovetail 542 against the surface defining the groove 564 in a friction fit manner. In addition or alternatively, a groove 564 may be provided in the first housing portion 530 and a dovetail 542 may be provided on the second housing portion 550 in a manner previously described.

Figure 36A:
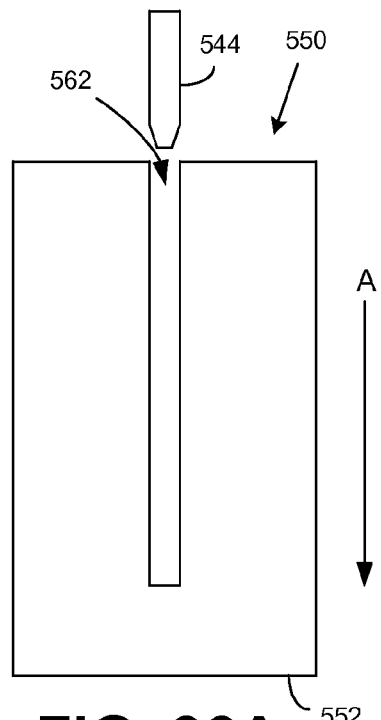
FIGS. 36A and 36B illustrate a portion of a medical device system in accordance with an embodiment of the present invention.
Figure 36B:
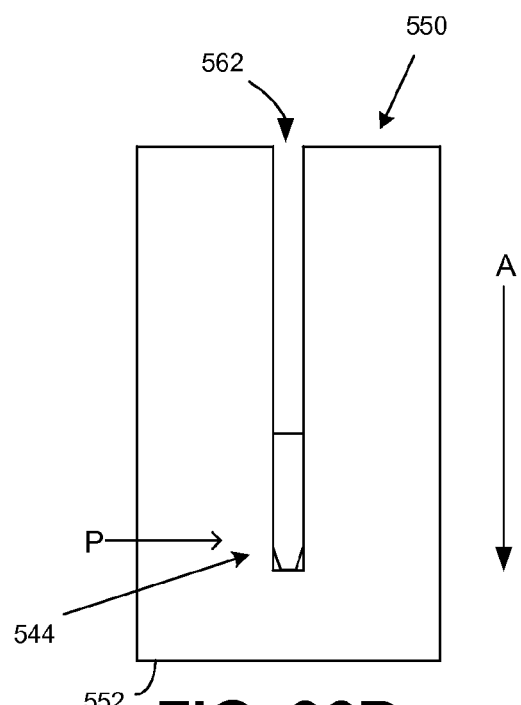

As another example shown in FIGS. 36A and 36B, a dovetail 544 may be tapered such that a front end of the dovetail 544 is narrower than a rear portion of the dovetail 544. Accordingly such embodiments, may allow for facilitating placement of the dovetail 544 in the groove 562, aligning of the first housing portion 530 as the dovetail 544 is guided by a surface defining the groove 562, and/or securing the dovetail 544 against the surface defining the groove 562 in a friction fit manner. In addition or alternatively, a groove 562 may be provided in the first housing portion 530 and a dovetail 544 may be provided on the second housing portion 550 in a manner previously described.

Returning to FIGS. 30A-34, in some embodiments, the arm 554 and/or the tab 555 may be angled relative to the second housing portion 550 to provide further alignment while connecting the first housing portion 530 to the second housing portion 550. For example, the arm 554 and/or the tab 55 may be angled outwardly (relative to the front end 552 of the second housing portion 550) to facilitate engagement with the arm 532, tab 534, and/or inner depression 533 of the first housing portion 530. As such, the arm 532 of the first housing portion 530 need only be placed in the depression 558 and advanced in the direction A to allow the tab 534 and/or the inner depression 533 to meet the angled arm 554 and/or tab 555 at which point the angled arm 554 and/or tab 555 may guide the arm 532 of the first housing portion 530 with continued movement of the first housing portion 530.

In such embodiments, the arm 532, the tab 534, and/or the entire first housing portion 530 may be made of a sufficiently flexible material, such as plastic, a composite material, and/or the like, to allow some flexing as the portion of the first housing portion 530 moves along the angled arm 554 and/or tab 555.

In some embodiments, such as the embodiments shown in FIGS. 33 and 34, one more rails 559, ridges, or other raised surfaces may be provided on the second housing portion 550 to guide the first housing portion 530 along the second housing portion 550. Accordingly, in various embodiments, the rails 559 may provide initial coarse horizontal alignment between the first housing portion 530 and the second housing portion 550 at the rear of the housing portions. The rails 559 may be parallel or nonparallel to each other. The rails 559 may define an opening 557 through which the first housing portion 530 may be slid. In some embodiments, the rails 559 may be on a periphery (either a portion or an entirety thereof) of the second housing portion 550, and in some embodiments, the rails 559 may be arranged at any suitable location (e.g., internal or away from the periphery) along the second housing portion 550 (and/or first housing portion 530), such as those described, for example, in FIGS. 37A-38C. In further embodiments, the first housing portion 530 may include arms (not shown) or the like for engaging the rails 559 to provide coarse vertical alignment between the first housing portion 530 and the second housing portion 550 at the rear of the housing portions.

In further embodiments, the rails 559 may be arranged to facilitate alignment and/or connection of the second housing portion 550 and the first housing portion 530. For example, opposing rails 559 may be arranged on the second housing portion 550 to be nonparallel to each other, as shown in, for example, FIGS. 37A-38C. The rails 559 may be angled inwardly (toward the front end 552 of the second housing portion 550) to provide a liberally sized opening 557 having a width dimension larger than a width dimension of the first housing portion 530 (or at least larger than a width dimension of a front portion of the first housing portion 530) so that the first housing portion 530 may be positioned easily within the opening 557. Accordingly, the first housing portion 530 may be advanced in the direction A toward the front end 552 of the second housing portion 550. In a case where, the first housing portion 530 is being advanced toward the front end 552 and is slightly misaligned, a portion of the first housing portion 530 may contact (e.g., FIG. 37B) at least one of the rails 559 at which point the contacted rail 559 may guide the first housing portion 530 toward an aligned position with continued movement of the first housing portion 530 in the direction A.

In other embodiments, the rails 559 may be parallel to each other with each of the rails 559 having a surface 559a that is nonparallel to a surface 559a of the other rail 559. As shown in FIGS. 38A-38C, the surface 559a of each of the rails 559 may face each other. Accordingly, the first housing portion 530 may be advanced in the direction A toward the front end 552 of the second housing portion 550. In a case where, the first housing portion 530 is being advanced toward the front end 552 and is slightly misaligned, a portion of the first housing portion 530 may contact (e.g., FIG. 38B) at least one of surfaces 559a of the rails 559 at which point the contacted surface 559a may guide the first housing portion 530 toward an aligned position with continued movement of the first housing portion 530 in the direction A.

Thus, various embodiments that include one or rails 559 may allow for some lateral misalignment at a beginning of the sliding motion (e.g., as the first housing portion 530 is moved in the direction A). Such embodiments additionally may allow for forcing or guiding the first housing portion 530 into proper alignment with the second housing portion 550 as the sliding motion proceeds in the direction A.

With reference to FIGS. 37A-38C, in further embodiments, once the first housing portion 530 is placed in the aligned position by the rails 559, the first housing portion 530 and the second housing 550 may engage each other in a manner previously described with respect to FIGS. 30A-36B. For example, the arm 554 and tab 555 of the second housing portion 550 may engage the arm 532 of the first housing portion 530 as the first housing portion 530 is slid in the direction A. As another example, a dovetail (e.g., 542) of the first housing portion 530 may engage a surface defining a groove (e.g., 562) of the second housing portion 550.

With reference to FIGS. 30A-38C, in further embodiments, at least one magnet (not shown) may be provided on one or both of the second housing portion 550 and the first housing portion 530 along with an magnetically attractive material (not shown), such as, but not limited to, metal, a magnet having an opposing pole, or the like, on the other of the second housing portion 550 and the first housing portion 530. Each of the magnet(s) and the magnetically attractive material may be arranged at a location to interact with each other upon the second housing portion 550 and the first housing portion 530 being connected properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first housing portion 530 and the second housing portion 550 for operation.

The magnets and the magnetically attractive material may be provided at one or more locations to interact with each other upon the first housing portion 530 being moved to the position P (or other position) relative to the second housing portion 550. For instance, in a case where the first housing portion 530 is moved to the position P, the magnet on one of the housing portions may interact with the magnet (or attractive material) on the other of the housing portions, for example, to connect and/or align the housing portions. Examples of magnetic connection and alignments structures and other alignment and connection structures will be described later and are also described in, but are not limited to, U.S. patent application Ser. No. 11/759,725, filed Jun. 7, 2007, entitled "Infusion Medium Delivery Device and Method with Drive Device for Driving Plunger in Reservoir," herein incorporated by reference in its entirety.

Figure 39A:
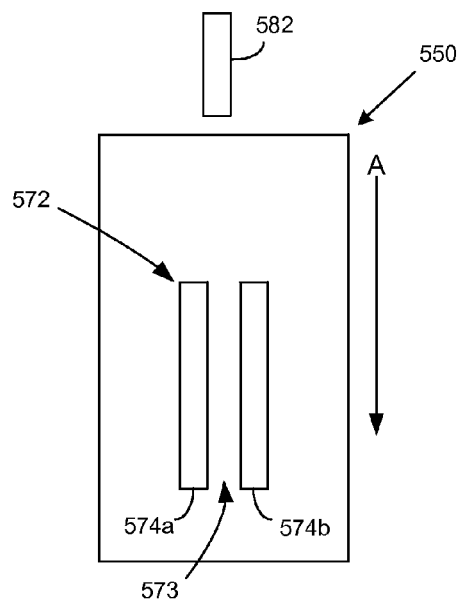
FIGS. 39A and 39B illustrate a portion of a medical device system in accordance with an embodiment of the present invention.
Figure 39B:
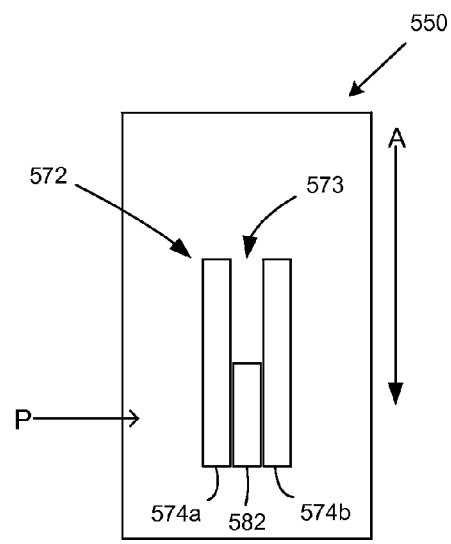

In some embodiments, such as the embodiments shown in FIGS. 39A and 39B, the first housing portion 530 and the second housing portion 550 may include magnets configured to align, for example laterally, the first housing portion 530 and the second housing portion 550 in a case where the first housing portion 530 and the second housing portion are being connected and are misaligned. For instance, the magnets may be arranged to oppose each other in a case where the first housing portion 530 and the second housing portion 550 are misaligned. For example, the magnets may each have surfaces having similar pole directions. For instance, a magnet 582 supported by the first housing portion (not shown in FIGS. 39A and 39B) may be opposed to one or more magnets 572 supported on the second housing portion 550. For example, the magnet 582 may have a surface have a first polarity (e.g., North), and the one or more magnets 572 may each have a surface having a polarity (e.g., North) similar to the first polarity of the magnet 582.

In some embodiments, the one or more magnets 572 may comprise a first magnet 574a and a second magnet 574b. A spacing 573 may be provided between the first magnet 574a and the second magnet 574b. In such embodiments, the first housing portion and the second housing portion 550 may be connected, for example, in a slidable manner as previously described. The magnet 582 may be guided along the one or more magnets 572 as the first housing portion is moved in the direction A. For example, the magnet 582 may move between the first magnet 574a and the second magnet 574b over the spacing 573. In such embodiments, lateral misalignment of the first housing portion and the magnet 582 may be inhibited by the opposing one or more magnets 572.

Figure 40A:
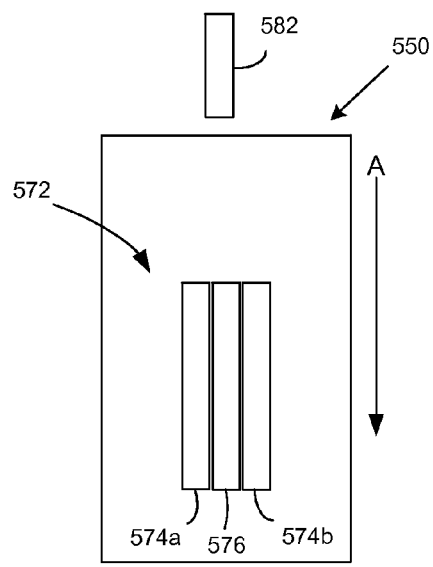
FIGS. 40A and 40B illustrate a portion of a medical device system in accordance with an embodiment of the present invention.
Figure 40B:
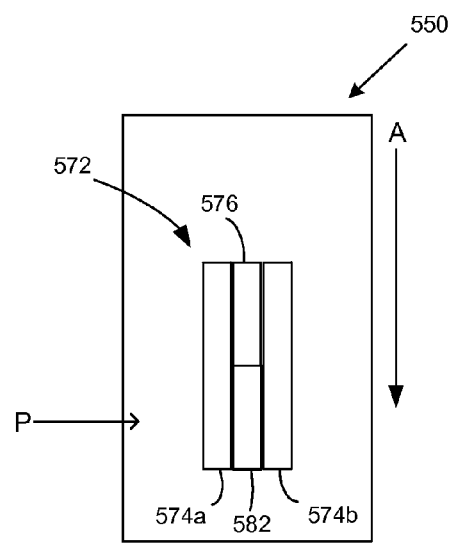

In further embodiments, such as that shown in FIGS. 40A and 40B, the one or more magnets 572 supported on the second housing portion 550 may include a third magnet 576 that is attracted to the magnet 582 supported by the first housing portion (not shown in FIGS. 40A and 40B). For example, the third magnet may have a second polarity (e.g., South) opposite the first polarity of the magnet 583. In some embodiments, the one or magnets 572 may include a magnetically attractive material (as opposed to a magnet), such as a metal, ferrous conduit, or the like.

In various embodiments, the first housing portion 530 and the second housing portion 550 may be connected, for example, in a slidable manner as previously described. The magnet 582 (and/or the magnetically attractive material) may be guided along the one or more magnets 572 as the first housing portion is moved in the direction A. For example, the magnet 582 may move between the first magnet 574a and the second magnet 574b over the third magnet 576. In such embodiments, lateral misalignment of the first housing portion and the magnet 582 may be inhibited by the opposing one or more magnets 572 and/or by the attraction between the magnet 582 and the third magnet 576 (and/or the magnetically attractive material).

With reference to FIGS. 39A-40B, in some embodiments, the magnets (e.g., 582, 572) may be arranged in a manner described with respect to, for example (but not limited to), the rails 559 and dovetail structures described in FIGS. 35A-38C. For instance, returning to FIGS. 39A-40B, the first magnet 574a and the second magnet 574b may be arranged to be non-parallel to each other (e.g., as described in FIGS. 37A-38C). As another example, the first magnet 574a and the second magnet 57b may be arranged to taper such that the spacing 573 narrows in the direction A, for example, as described in FIGS. 35A-36B.

With reference to FIGS. 30A-40B, in some embodiments, at least one latch (not shown), or the like may be provided on one of the second housing portion 550 and the first housing portion 530. The latch (e.g., 1038 in FIGS. 54A and 54B) may be configured to engage an aperture 568, cavity, engagement member, and/or the like in the other of the second housing portion 550 and the first housing portion 550 upon the second housing portion 550 and the first housing portion 530 being operatively engaged (e.g., the first housing portion 530 moved toward the position P).

In further embodiments, the latch may be configured to manually engage and/or disengage the aperture 568 (or the like). For instance, the latch (or portion of the housing portion on which the latch is provided) may be configured to be squeezable (e.g., pressed inward relative to the housing portions) to allow the first housing portion 530 to engage and/or disengage from the second housing portion 550. For example, a latch may be provided on each side of the first housing portion 530 such that a squeezing motion of the latches (e.g., toward each other) may allow each of the latches to be released from a corresponding aperture 568 (or the like) to allow the first housing portion 530 to be removed from the second housing portion 550.

In yet further embodiments, the latch may be configured to force the first housing portion 530 and the second housing portion 550 apart in a case where the first housing portion 530 and the second housing portion 550 are not properly connected. For example, in a case where the first housing portion 530 is not slid sufficiently relative to the second housing portion 550 (in the direction A) so that the latch engages the aperture, the latch may force the first housing portion 530 in an opposite direction (to the direction A) to further separate the first housing portion 530 and the second housing portion 550. Accordingly, the connection process may be re-attempted until the latch engages the aperture. In particular embodiments, a bias member (not shown), such as a spring, resilient material, and/or the like, may be provided with and/or comprise the latch. The bias member may bias the first housing portion 530 away from the second housing portion 550, for example, in a direction opposite the direction A. As such, in a case where the first housing portion 530 is moved sufficiently in the direction A relative to the second housing portion 550, the latch may engage the aperture (or the like). Whereas in a case where the first housing portion 530 is not moved sufficiently in the direction A relative to the second housing portion 550, the bias member may urge the first housing portion 530 apart from the second housing portion 550, for example, in the opposite direction to the direction A to allow the user-patient to repeat the connection process.

Returning to FIG. 33, in some embodiments, the latch may be a tab or protrusion (e.g., 1038 in FIGS. 54A and 54B). The tab may be flexible or supported on a portion of the first housing portion 530 that is flexible. A recess 566 of the second housing portion 550 may be for receiving tab of the first housing portion 530 during the initial engagement of the first housing portion 530 and the second housing portion 550. In FIG. 33, the recess 566 is provided on a rear portion of the second housing portion 550, but in other embodiments, the recess 566 may be provided at any suitable location. During the sliding connection of the first housing portion 530 and the second housing portion 550 as previously described, the tab may be received by the recess 566 and guided by a surface (e.g., protrusion 567) defining at least a portion of the recess 566.

A protrusion 567 may be arranged on the second housing portion 550 to direct or flex the tab inwardly (or outwardly) as the first housing portion 530 moves (e.g., slides) in the direction A. That is, the protrusion 567 may be arranged to direct or flex the tab in a direction transverse to the direction A. Continued movement of the first housing portion 530 in the direction A beyond the protrusion 567 may allow the tab to flex in the opposite direction into the cavity 568 or an abutment or other engagement member in or defining the cavity 568 of the second housing portion 550.

The dimensions of the first housing portion 530 and the second housing portion 550 and arrangement of the recess 566, cavity 568, and tab may be selected such that the tab enters the cavity 568 upon the first housing portion 530 being toward the position P. As discussed, moving the first housing portion 530 toward the position P may allow, for example, the fluid conduit 524 to engage with (i.e., be in fluid communication with) the interior volume of the reservoir housing 508.

The tab may remain in the cavity 568 until the patient-user pushes the tab inwardly (or outwardly) to clear the protrusion 567. Accordingly, the first housing portion 530 may be moved in the opposite direction from the direction A, for example, to disengage the first housing portion 530 and the second housing portion 550. In additional or alternatively, the first housing portion 530 may have a recess for receiving a tab of the second housing portion 550 in a slidable manner with a protrusion and a cavity for retaining the tab in a manner previously described. In some embodiments, the tab and the recess 566 may be the dovetail (e.g., 542) and the groove (e.g., 562) as described, for example, with respect to FIGS. 35A-36B.

In some embodiments, a sensor (not shown) may be provided for sensing the latch and/or a relative position of the latch and/or a portion of the latch, for example a detectable feature (e.g., an interactive element as discussed in the disclosure) of the latch or provided on the latch. As such, the sensor can determine whether the latch has properly engaged the aperture (or the like) to determine that the second housing portion 550 and the first housing portion 530 have been properly connected (e.g., the first housing portion 530 is in the position P). Examples of sensors, detectable features, interactive elements, and the like are described in the disclosure and in, but not limited to, U.S. patent application Ser. No. 12/649,619, filed Dec. 30, 2009, entitled "Alignment Systems and Methods," herein incorporated by reference in its entirety.

Suitable electronics may be connected to the sensor to provide a controlled power signal to selectively activate or otherwise control one or more of the sensor and/or other components as described in the disclosure. For example, the sensor may be controlled to activate upon a manual activation of a control button, switch, or other manual operator on one of the connectable components or on a remote-controller device (not shown) connected in wireless communication with the sensor through suitable control electronics. As another example, the sensor may be controlled to activate automatically after a certain action, such as activation of a button, and/or the like or after a certain amount of time. In some embodiments, the sensor may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in its entirety. Thus, in such examples, the sensor may be activated, for example, before or after, the first housing portion 530 and the second housing portion 550 are brought operatively engaged.

Further examples of connection and/or alignment structures are described with reference to FIGS. 41A-43B, wherein a medical device system 900 may incorporate two parts: a first housing portion 901 and a second housing portion 902. Other embodiments may include medical device systems with more than two parts.

The medical device system 900 may be similar to or employed as an embodiment of the medical device system 500 (e.g., FIGS. 30A-40B) and/or the other medical device systems discussed in the disclosure. Although the medical device system 900 may include features similar or used with the embodiments of FIGS. 30A-40B, it should be understood that the medical device system 900 may also include some or all of the same features and operate in a manner similar to that shown and described in the embodiments of FIGS. 1-29B and/or any of the other embodiments described in the disclosure (e.g., FIGS. 44A-47C). In addition, some or all of the features shown in FIGS. 1-40B (and/or any of the other embodiments described in the disclosure) may be combined in various ways and included in the embodiments shown in FIGS. 41A-43B. Likewise, it should be understood that any of the features of the embodiments of FIGS. 41A-43B may be combined or otherwise incorporated into any of the other embodiments of FIGS. 41A-43B as well as any other embodiment herein discussed.

In various embodiments, the first housing portion 901 may be, but is not limited, to any of the housing portions described, such as the durable portion 30 (e.g., FIGS. 1-6C) and the disposable portion 20 (e.g., FIGS. 1-6C). In specific embodiments, the first housing portion 901 may be similar to the first housing portion 530 (e.g., FIGS. 30A-40B).

Moreover in various embodiments, the second housing portion 902 may be, but is not limited, to any of the housing portions described, such as the base 21 (in FIGS. 1-6C), the durable housing portion 30, and the disposable housing portion. In specific embodiments, the second housing portion 902 may be similar to the second housing portion 550 (e.g., FIGS. 30A-40B). In such embodiments, for example, the second housing portion 902 may be secured to skin of a patient-user or otherwise carried by the patient-user (e.g., secured on a belt, clothing, or the like) during operation of the medical device system 900.

The first housing portion 901 may include a plurality of electrical contacts 910 including a first main electrical contact 912 and a second main electrical contact 916. The plurality of electrical contacts 910 may also include one or more other electrical contact 914. The electrical contacts 910 may me made of any suitable material such as metal, a rubber conductive pad, as well as any other electrical conductor.

In some embodiments, the other electrical contact 914 may be arranged between the first main electrical contact 912 and the second main electrical contact 916. However, the other electrical contact 914 may be arranged at any suitable location. The other electrical contact 914 may be made of the same material as the first main electrical contact 912 and/or the second main electrical contact 914. In other embodiments, the other electrical contact 914 may be made of a different material (e.g., a different conductive material, or a non-conductive material) from the first main electrical contact 912 and/or the second main electrical contact 914.

The second housing portion 902 may include a shorting mechanism 920 or the like configured to establish a short or electrical connection with at least some of the electrical contacts 910 upon connecting the first housing portion 901 and the second housing portion 902. In some embodiments, the shorting mechanism 920 may establish an electrical connection with at least some of the electrical contacts 910 in a case where the first housing portion 901 and the second housing portion 902 are connected properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first housing portion 901 and the second housing portion 902 for operation. In other embodiments, the shorting mechanism 920 may be a known resistance or the like.

The shorting mechanism 920 may have a first end 922 and a second end 924 for contacting respective electrical contacts 910 on the first housing portion 901. In some embodiments, the first end 922 and the second end 924 may be arranged to contact the first main electrical contact 912 and the second main electrical contact 916 respectively when the first housing portion 901 and the second housing portion 902 are connected properly, for example, as shown in FIG. 41B. As such, the shorting mechanism 920 may contact the first main electrical contact 912 and the second main electrical contact 916, but not the other electrical contact 914. Suitable circuitry (not shown) connected to the electrical contacts 910 may be configured to detect an electrical connection or short between the first main electrical contact 912 and the second main electrical contact 916 (via the shorting mechanism 920) indicating a proper connection of the first housing portion 901 and the second housing portion 902.

Furthermore, the electrical contacts 910 and/or the shorting mechanism 920 may be arranged on their respective parts such that in a case where the first housing portion 901 and the second housing portion 902 are not properly connected, such as in FIG. 41C, an electrical connection between the first main electrical contact 912 and the second main electrical contact 916 is not established. Accordingly, this may indicate that the first housing portion 901 and the second housing portion 902 have not been connected properly.

Returning to FIGS. 41A-41C, some embodiments in which at least one other electrical contact 914 is arranged between the first main electrical contact 912 and the second main electrical contact 916 may prevent a false detection of a proper connection of the first housing portion 901 and the second housing portion 902. For example, the circuitry may be able to distinguish between a case where a stray metal object (e.g., a metal key, paper clip, coin) or other electrical conductor contacts the first main electrical contact 912, the second main electrical contact 916, and the other contact 914 as opposed to a proper connection where only the first main electrical contact 912 and the second main electrical contact 912 are contacted (by the shorting mechanism).

In some embodiments, an electrical connection will only be established when the first end 922 contacts the first main electrical contact 912 and the second end 924 contacts the second main electrical contact 916. In other embodiments, an electrical connection may be established in a case where the first end 922 and the second end 924 contact the first main electrical contact 912 and the second main electrical contact 916 respectively or in a case where the first end 922 and the second end 924 contact the second main electrical contact 916 and the first main electrical contact 912 respectively. Such embodiments, may allow for a detection of a proper connection of the first housing portion 901 and the second housing portion 902 in more than one orientation.

In the embodiments shown in FIGS. 41A-41C, there are three electrical contacts: the first main electrical contact 912, the second main electrical contact 916, and the other electrical contact 914 arranged between the first main electrical contact 912 and the second main electrical contact 916. However, in various other embodiments, any suitable number of electrical contacts 910 may be provided on the first housing portion 901 as required. In some embodiments, the main electrical contacts (e.g., 912, 916) are arranged as the outermost electrical contacts; however, in other embodiments, the main electrical contacts may be arranged anywhere relative to the other electrical contact(s) 914.

Similarly, the other electrical contacts need not be limited to being arranged in between main electrical contacts, but may also be arranged to be the outermost electrical contact in some embodiments. As such, the electrical contacts 910 (e.g., main electrical contacts and other electrical contacts) may be arranged or otherwise provided on the first housing portion 901 in any suitable manner, for example linearly/non-linearly, equidistant/non-equidistant, similar/varying heights, arranged on similar/varying surfaces, same/different resistances, same/different materials, and/or the like. For instance, as shown in FIG. 42, seven electrical contacts 910 could be provided including two first main electrical contacts 912, a first other electrical contact 914, a second main electrical contact 916, a second other electrical contact 914, and two third main electrical contacts 918.

In the embodiments shown in FIGS. 41A-41C, the shorting mechanism 920 has two ends 922, 924 for contacting the first main electrical contact 912 and the second main electrical contact 916, respectively. However, in various other embodiments, the shorting mechanism 920 may be provided with any suitable number of ends or contact surfaces for contacting the electrical contacts 910 as required. Similarly, the ends (e.g., 922, 924) may be arranged on shorting mechanism 920 in any suitable manner.

In various embodiments, the electrical contacts 910 may be provided on the first housing portion 901 and the shorting mechanism 920 may be provided on the second housing portion 902. In other embodiments, the electrical contacts 910 may be provided on the second housing portion 902 and the shorting mechanism 920 may be provided on the first housing portion 901. In further embodiments, each of the first housing portion 901 and the second housing portion 902 may be provided with a shorting mechanism 920 and complementing electrical contacts 910.

In some embodiments, such as the embodiments shown in FIGS. 43A and 43B, a bias member 919, such as a spring, or the like, may be provided to bias the electrical contacts 910 either individually, partially (e.g., some, but not all), or collectively toward a first position (e.g., an extended position as shown in FIG. 43A). As such, the electrical contacts 910 may be moveable toward a second position (e.g., a retracted position as shown in FIG. 43B), for example, as the first housing portion 901 and the second housing portion 902 are brought together. Thus, while in the second position, an electrical connection may be established between the first main electrical contact 912 and the second main electrical contact 916 via the shorting mechanism 910 in a similar manner to that previously described. The bias member 919 may be located at least partially within a recess of the first housing portion 901. In some embodiments, the bias member 919 may be supported on the first housing portion 901, for example, between the electrical contacts 910 and the first housing portion 901.

In addition or in alternative to the above, in some embodiments, a bias member, such as a spring, or the like, may be provided to bias the shorting mechanism or portion thereof (e.g., ends 922, 924) toward a first position (e.g., an extended position). As such, shorting mechanism or portion thereof may be moveable toward a second position (e.g., a retracted position), for example, as the first housing portion 901 and the second housing portion 902 are brought together. Thus, while in the second position, an electrical connection may be established between the first main electrical contact 912 and the second main electrical contact 916 via the shorting mechanism 910 in a similar manner to that previously described.

In various embodiments, the electrical contacts 920 and/or the shorting mechanism 910 may be or otherwise comprise a bias member like that previously described. For example, the electrical contacts 920 may be metal springs or the like that may be moveable from the first position to the second position as the first housing portion 901 and the second housing portion 902 are brought together.

Further examples of connection and/or alignment structures are described with reference to FIGS. 44A-45B, wherein a medical device system 1100 may incorporate two parts: a first housing portion 1101 and a second housing portion 1102. Other embodiments may include medical device systems with more than two parts.

The medical device system 1100 may be similar to or employed as an embodiment of the medical device system 500 (e.g., FIGS. 30A-40B), the medical device system 900 (e.g., FIGS. 41A-43B), and/or the other medical device systems discussed in the disclosure. Although the medical device system 1100 may include features similar or used with the embodiments of FIGS. 30A-43B, it should be understood that the medical device system 1100 may also include some or all of the same features and operate in a manner similar to that shown and described in the embodiments of FIGS. 1-29B and/or any of the other embodiments described in the disclosure (e.g., FIGS. 46A-47C). In addition, some or all of the features shown in FIGS. 1-43B (and/or any of the other embodiments described in the disclosure) may be combined in various ways and included in the embodiments shown in FIGS. 44A-45B. Likewise, it should be understood that any of the features of the embodiments of FIGS. 44A-45B may be combined or otherwise incorporated into any of the other embodiments of FIGS. 44A-45B as well as any other embodiment herein discussed.

In various embodiments, the first housing portion 1101 may be, but is not limited, to any of the housing portions described, such as the durable portion 30 (e.g., FIGS. 1-6C) and the disposable portion 20 (e.g., FIGS. 1-6C). In specific embodiments, the first housing portion 1101 may be similar to the first housing portion 530 (e.g., FIGS. 30A-40B).

Moreover in various embodiments, the second housing portion 1102 may be, but is not limited, to any of the housing portions described, such as the base 21 (FIGS. 1-6C), the durable housing portion 30, and the disposable housing portion. In specific embodiments, the second housing portion 1102 may be similar to the second housing portion 550 (e.g., FIGS. 30A-40B). In such embodiments, the second housing portion 1102 may be secured to skin of a patient-user during operation of the medical device system 1100.

The first housing portion 1101 may include a sensor 1110 for sensing a magnetic field, and in specific embodiments, for sensing at least a direction (i.e., vector) of a magnetic field. Such sensors 1110 may allow for detecting a presence of a magnetic field or magnetic source independent of magnetic strength. Furthermore, sensing a direction of a magnetic field may increase the probability that the sensor 1110 is sensing the appropriate the magnetic source. The sensor 1110 may be similar to the sensors described in, but is not limited to, U.S. patent application Ser. No. 12/649,619, filed Dec. 30, 2009, entitled "Alignment Systems and Methods," herein incorporated by reference in its entirety. The sensor 1110 may be disposed in the first housing portion 1101 or be provided on the first housing portion 1101.

Suitable electronics may be connected to the sensor 1110 to provide a controlled power signal to selectively activate or otherwise control one or more of the sensor 1110 and/or other components as described in the disclosure. For example, the sensor 1110 may be controlled to activate upon a manual activation of a control button, switch, or other manual operator on one of the connectable components or on a remote-controller device (not shown) connected in wireless communication with the sensor 1110 through suitable control electronics. As another example, the sensor 1110 may be controlled to activate automatically after a certain action, such as activation of a button, and/or the like or after a certain amount of time. In some embodiments, the sensor 1110 may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor 1110 may be activated, for example, before or after, the first housing portion 1101 and the second housing portion 1102 are brought operatively engaged.

The second housing portion 1102 may include a magnetic source 1120 or the like for providing a magnetic field having a direction. The magnetic source 1120 may be arranged on or in the second housing portion 1102 at a location to allow the magnetic field and/or the direction of the magnetic field of the magnetic source 1120 to be detectable by the sensor 1110 in a case where the first housing portion and the second housing portion 1102 are connected properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first housing portion 1101 and the second housing portion 1102 for operation. Detection of the magnetic field and/or the direction of the magnetic field of the magnetic source 1120 may indicate that the first housing portion 1101 and the second housing portion 1102 have been connected properly.

In some embodiments, the magnetic source 1120 may be in contact with the sensor 1110 to allow the sensor 1120 to detect the magnetic field and/or direction of the magnetic field of the magnetic source 1120. In other embodiments, the magnetic source 1120 need not be in contact with the sensor 1110 to allow the sensor 1110 to detect the magnetic field and/or direction of the magnetic field of the magnetic source 1120. For example, a portion of one or both of the first housing portion 1101 and the second housing portion 1102 may be arranged between the sensor 1110 and the magnetic source 1120.

Furthermore, the sensor 1110 and the magnetic source 1120 may be arranged such that in a case where the first housing portion 1101 and the second housing portion 1102 are not been properly connected, the sensor 1110 will not be able to detect the magnetic field and/or the direction of the magnetic field, for example, because the sensor 1110 and the magnetic source 1120 are too far apart. Accordingly, this may indicate that the first housing portion 1101 and the second housing portion 1102 have not been connected properly.

In some embodiments, the magnetic source 1120 may provide more than one magnetic fields and/or directions of magnetic fields. As shown for example in FIGS. 44A and 44B, a first field 1122, a second field 1124, and a third field 1126 are provided in which the first field 1122 and the third field 1126 have a direction different from a direction of the second field 1124. In such an example, the sensor 1110 may be configured to detect only the second field 1124 and/or the direction (e.g., North) of the second field 1124 in a manner previously described. Thus, detection of the second field 1124 and/or the direction of the second field 1124 may indicate that the first housing portion 1101 and the second housing portion 1102 have been connected properly.

In further embodiments, the sensor 1110 may be configured to detect other fields (e.g., first field 1122 and second field 1126) and/or directions of the other fields such that detection of the other fields and/or directions of the other fields may indicate an improper connection of the first housing portion 1101 and the second housing portion 1102. The electronics may employ an algorithm for processing information relating to the various fields and/or other related information (e.g., magnetic field strength, gauss level, and/or the like).

In some embodiments, such as the embodiments shown in FIGS. 45A-45B, the first housing portion 1101 may have a sensor 1111 for sensing a gauss level or the like of a magnetic source. The sensor 1111 may be similar to the sensor 1110 previously described or any of the sensors described in, but is not limited to, U.S. patent application Ser. No. 12/649,619, filed Dec. 30, 2009, entitled "Alignment Systems and Methods," herein incorporated by reference in its entirety. The sensor 1111 may be disposed in the first housing portion 1101 or be provided on the first housing portion 1101.

Suitable electronics may be connected to the sensor 1111 to provide a controlled power signal to selectively activate or otherwise control one or more of the sensor 1111 and/or other components as described in the disclosure. For example, the sensor 1111 may be controlled to activate upon a manual activation of a control button, switch, or other manual operator on one of the connectable components or on a remote-controller device (not shown) connected in wireless communication with the sensor 1111 through suitable control electronics. As another example, the sensor 1111 may be controlled to activate automatically after a certain action, such as activation of a button, and/or the like or after a certain amount of time. In some embodiments, the sensor 1111 may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor 1111 may be activated, for example, before or after, the first housing portion 1101 and the second housing portion 1102 are brought operatively engaged.

The second housing portion 1102 may include a magnetic source 1121 or the like for providing a certain gauss level. The magnetic source 1121 may be similar to the magnetic source 1120 previously described or any of the magnetic sources described in, but is not limited to, U.S. patent application Ser. No. 12/649,619, filed Dec. 30, 2009, entitled "Alignment Systems and Methods," herein incorporated by reference in its entirety.

The magnetic source 1121 may be arranged on or in the second housing portion 1102 at a location to allow the gauss level of the magnetic source 1121 to be detectable and/or measurable by the sensor 1110 in a case where the first housing portion and the second housing portion 1102 are connected properly. Detection of gauss level of the magnetic source 1121 may indicate that the first housing portion 1101 and the second housing portion 1102 have been connected properly. In further embodiments, the sensor 1111 and/or associated electronics may be configured to detect a gauss level that is within a specified range. In such embodiments, a gauss level that is below or exceeds the specified range may indicate an improper connection.

In some embodiments, the magnetic source 1121 may be in contact with the sensor 1111 to allow the sensor 1111 to detect the gauss level of the magnetic source 1121. In other embodiments, the magnetic source 1121 need not be in contact with the sensor 1111 to allow the sensor 1111 to detect the gauss level of the magnetic source 1121. For example, a portion of one or both of the first housing portion 1101 and the second housing portion 1102 may be arranged between the sensor 1111 and the magnetic source 1121.

Furthermore, the sensor 1111 and the magnetic source 1121 may be arranged such that in a case where the first housing portion 1101 and the second housing portion 1102 are not been properly connected, the sensor 1111 will not be able to detect the gauss level (or the gauss level is not within a detectable range) of the magnetic source 1121, for example, because the sensor 1111 and the magnetic source 1121 are too far apart. Accordingly, this may indicate that the first housing portion 1101 and the second housing portion 1102 have not been connected properly.

In further embodiments, electronics (not shown), such as a magnetic threshold switch (e.g., hall switch, reed switch, and/or the like), or the like, associated with the sensor 1111 may be configured to provide a signal or the like upon the sensor 1111 (or other sensor) sensing a signal outside a second range, which in some embodiments may be the same the specified range. In other embodiments, the second range may be different from the specified range. For example, the electronics may provide a signal to the control electronics of the medical device system 1100 to disable the medical device system 1100 or certain portions thereof if a gauss level beyond the second range is detected. Such embodiments may protect the various electronics of the medical device system 1100 in a case where the medical device system 1100 is in operation and is exposed to a strong external magnetic influence, such as an MRI (magnetic resonance imaging) machine, or the like.

In some embodiments, the magnetic source 1121 may provide more than one gauss level. In such embodiments, the sensor 1111 may be configured to detect only a particular gauss level corresponding to a proper connection of the first housing portion 1101 and the second housing portion 1102 similar to a manner previously described. Thus, detection of the particular gauss level may indicate that the first housing portion 1101 and the second housing portion 1102 have been connected properly. In further embodiments, the sensor 1111 may be configured to detect other gauss levels such that detection of the other gauss levels may indicate an improper connection of the first housing portion 1101 and the second housing portion 1102. The electronics may employ an algorithm for processing information relating to the various gauss levels and/or other related information (e.g., magnetic field strength, direction of a field, and/or the like).

With reference to FIGS. 45A-45B, in various embodiments, the sensor 1110 and the sensor 1111 may be the same sensor and thus may be configured to sense both a direction of magnetic field and a gauss level from a magnetic source. In some embodiments, the sensor 1110 and the sensor 1111 may both provided for sensing a magnetic source (e.g., 1120, 1121) as previously described. The sensor 1110 and the sensor 1111 may be arranged to sense the same magnetic source or respective magnetic sources. In further embodiments, the electronics may employ an algorithm for processing information relating to the various gauss levels, field directions, and/or other related information.

In various embodiments, the sensor 1110, 1111 may be provided on the first housing portion 1101 and the magnetic source 1120, 1121 may be provided on the second housing portion 1102. In other embodiments, the sensor 1110, 1111 may be provided on the second housing portion 1102 and the magnetic source 1120, 1121 may be provided on the first housing portion 1101. In further embodiments, each of the first housing portion 1101 and the second housing portion 1102 may be provided with a sensor (e.g., 1110, 1111) and complementing magnetic source (e.g., 1120, 1121).

With reference to FIGS. 41A-45B and 48, the sensors and/or the electrical contacts may be in electrical communication with electronics (not shown). The electronics may be incorporated within control electronics for controlling a drive device 44 (e.g., FIG. 4) such as, but not limited to, control electronics 52 (e.g., FIG. 4) for controlling the drive device 44. Alternatively, the electronics may be separate from and in addition to the control electronics 52, but connected in electrical communication with the control electronics 52 and/or the drive device 44 to provide a drive control signal to the drive device 44. More specifically, the electronics may be configured to inhibit operation of the drive device 44, unless a signal or a change in state is received by the control electronics 52.

For instance, as previously discussed, a signal or a change in state may be provided upon the first end 922 and the second end 924 interacting with the first main contact 912 and the second main contact 916, for example, in a case where the first housing portion 901 and the second housing portion 902 are in proper alignment and sufficiently close in proximity to connect for operation. In other words, the drive device 44 may be inoperable unless the first housing portion 901 and the second housing portion 902 are operatively engaged properly (i.e., aligned and/or connected properly).

The electronics and/or the control electronics 52 (e.g., FIG. 4) may be configured to control the drive device 44 (e.g., FIG. 4) in various manners in accordance with various embodiments of the invention. Examples are discussed in, but are not limited to, U.S. patent application Ser. No. 11/759,725, entitled "Infusion Medium Delivery Device and Method with Drive Device for Driving Plunger in Reservoir"; and U.S. patent application Ser. No. 12/649,619, filed Dec. 30, 2009, entitled "Alignment Systems and Methods," both of which are herein incorporated by reference in their entirety.

For example, the drive device 44 may be controlled to stop pumping (delivery) operation upon a detection of an interruption of a fluid-flow path or a disconnection of a critical component in the medical device system (e.g., 900, 1100). These may include, but are not limited to, a disconnection of a housing portion from another housing portion or from a base portion, a disconnection of a conduit from another conduit or from a reservoir, a disconnection of a reservoir from a housing portion or a base, and/or the like.

In yet further embodiments, additional sensors may be provided within the medical device system and connected for electrical communication with the electronics 414. Such additional sensors may comprise magnetically and/or electronically actuating switches, magnetic and/or electric field magnitude and direction sensors, inductive sensors, other proximity sensors, contact sensors, and/or the like for providing a detectable signal or change in a state upon proper connection of other components in the medical device system. Such proper connection of other components may comprise, for example, one or more of a proper connection of a reservoir into a housing portion or base, a proper connection of a conduit to a reservoir, a proper connection of two conduits together, a proper setting of a needle or cannula in an inserted state, a proper connection of a conduit to a cannula or needle, or a proper connection of other components of or to the medical device system.

In alternative or in addition, the electronics and/or the control electronics 52 (e.g., FIG. 4) may be configured to detect a first-time connection of a first housing portion (e.g., 901) and a second housing portion (e.g., 902) or a first-time connection of other components, as compared to a re-connection after previous or partial usage. In this manner, the drive device 44 may be controlled to provide a priming operation or other suitable first-time operation(s) upon detection of a first-time connection of the first part 401 and the second part 402.

In various embodiments, the sensors, electrical contacts, and/or associated circuitry may allow for, but is not limited to, tracking a number of times a component has been connected to and/or disconnected from other components, verifying proper connection and/or alignment of components in a medication delivery system prior to each delivery step, checking, sensing, and/or measuring parameters, such as ambient parameters (e.g., ambient magnetic fields), operating parameters, and/or the like, alerting users to conditions, such as conditions outside operating parameters of the delivery system, and/or the like.

Various embodiments may allow for verification between two (or more) distinct and separate components, verification of correct positioning between the two (or more) distinct and separate components, verification that the two (or more) distinct and separate components have been connected in the correct order, a safety mechanism to provide notification of separation (intentional or accidental) of any individual component in a multi-component system, and/or the like.

In alternative or in addition, the electronics and/or the control electronics 52 (e.g., FIG. 4) may be configured to provide a user-perceptible indication of a proper alignment and/or connection of the first housing portion and the second housing portion or of other components. For example, upon detection of a proper alignment and/or connection of the first housing portion and the second housing portion 402, the electronics 414 and/or the control electronics 52 may provide a suitable control signal to activate an indicator device 420, as shown in FIG. 36.

The indicator device 420 may be operated by a processor 422. The processor 422 may be configured to execute various programs and/or to process various information, such as data received from one or more sensors, responsive devices, and/or other interactive elements. The processor 422, for example, may be configured to compare detected signals with thresholds and/or pre-stored values in memory 424.

With reference to FIGS. 41A-45B and 48, the indicator device 420 may include, but is not limited to, an audible indicator, an optical indicator, a tactile indicator, combinations of one or more those indicators, and/or the like. For example, upon a proper alignment or connection of components as described above, an audible beeping sound or other suitable sound may be generated by a sound generating device in or associated with one or both of the first housing portion and the second housing portion. For example, upon a proper alignment or connection of components as described above, a flashing light or other suitable visual indicator may be generated by an LED or other light source or a display device on or associated with one or both of the first housing portion and the second housing portion. For example, upon a proper alignment or connection of components as described above, a vibration and/or the like may be generated by a vibration device and/or the like in or associated with one or both of the first housing portion and the second housing portion. Examples of indicator devices are discussed in, but are not limited to, U.S. patent application Ser. No. 11/759,725, entitled "Infusion Medium Delivery Device and Method with Drive Device for Driving Plunger in Reservoir"; and U.S. patent application Ser. No. 12/649,619, filed Dec. 30, 2009, entitled "Alignment Systems and Methods," both of which are herein incorporated by reference in their entirety.

FIGS. 46A-47C illustrate a medical device system 600 according to various embodiments of the present intention. The medical device system 600 may include features similar or may be employed as an embodiment of the medical device system 100 (e.g., FIGS. 7-23, the medical device system 200 (e.g., FIGS. 16-19), the medical device system 300 (e.g., FIGS. 20-23), the medical device system 400 (e.g., FIGS. 24-29B), the medical device system 500 (e.g., FIGS. 30A-40B), the medical device system 900, (e.g., FIGS. 41A-43B), the medical device system 1100 (e.g., FIGS. 44A-45B), and/or any of the other embodiments described in the disclosure. Although the medical device system 600 may include features similar or used with the embodiments of FIGS. 7-45B, it should be understood that the medical device system 600 may also include some or all of the same features and operate in a manner similar to that shown and described in the embodiments of FIGS. 1-6C and 48-59B. In addition, some or all of the features shown in FIGS. 1-45B and 48-59B (and/or any of the other embodiments described in the disclosure) may be combined in various ways and included in the embodiments shown in FIGS. 46A-47C. Likewise, it should be understood that any of the features of the embodiments of FIGS. 46A-47C may be combined or otherwise incorporated into any of the other embodiments of FIGS. 46A-47C as well as any other embodiment herein discussed.

A generalized representation of a first part 601 and a second part 602 of the medical device system 600 is shown in FIGS. 46A-47C. The first part 601 and the second part 602 may be configured to be connectable to each other or to be otherwise operatively engageable with each other.

The first part 601 and the second part 602 may each be one of two housing portions, such as, but not limited to, a durable housing portion 30 (e.g., FIGS. 1-6C) and a disposable housing portion 20 (e.g., FIGS. 1-6C), respectively, as previously described. As previously discussed with respect to FIGS. 1-6C, the durable housing portion 30 may include various components, such as, but not limited to, a drive device 80, drive motor 84, drive device linkage portion 82, and/or the like. The disposable housing portion 20 may include various components, such as, but not limited to, a reservoir system 40. Returning to FIGS. 46A-47C, alternatively, one of the first part 601 and the second part 602 may be a base portion 21 (e.g., FIGS. 1-6C) and the other of the first part 601 and the second part 602 may be a housing portion such as, but not limited to, the durable housing portion 30 and/or the disposable housing portion 20. In some embodiments, one of the housing portions may be or may include a reservoir system 40 (e.g., FIGS. 1-6C).

The first part 601 and the second part 602 may be configured to engage each other in a sliding motion (or other suitable motion) at least from a first position P1 to a second position P2. In specific embodiments, the first part 601 and the second part 602 are configured to align with each other at the first position P1 and detect whether the first part 601 and the second part 602 are properly engaged when in the second position P1.

In some embodiments, one of the medical device system 600 parts (e.g., 601 in FIGS. 46A-47C) may be provided with a first interactive element 604, which may be similar to any of the first interactive elements (e.g., 104, 204, 304, 404, 504, etc. in FIGS. 7-29B) discussed in the disclosure. The other medical device system 600 part (e.g., 602 in FIGS. 46A-47C) may be provided with a second interactive element 606, which may be similar to any of the second interactive elements (e.g., 106, 206, 306, 406, 506, etc. in FIGS. 7-29B) discussed in the disclosure. The first interactive element 604 and the second interactive element 606 may be configured to interact with each other in a detectable manner when in sufficiently close proximity to each other. As detailed in the disclosure, interaction between the various elements, such as (but not limited to) between the first interactive element 604 and the second interactive element 606, may include (but is not limited to) engaging of the elements, contact between the elements, application of a force (e.g., pressure) of one element on the other element, application of energy (e.g., electrical charge, magnetic charge, heat, etc.), and/or any suitable exchange between the elements that is detectable.

The first interactive element 604 may be arranged in a fixed relation to the first part 601, for example, by attaching, forming, or otherwise supporting the first interactive element 604 to a suitable location on a wall or on other structure of or in the first part 601. The second interactive element 606 may be arranged in a fixed relation to the second part 602, for example, by attaching, forming, or otherwise supporting the second interactive element 606 to a suitable location on a wall or on other structure of or in the second part 602. In some embodiments, the second interactive element 606 may be arranged on the second part 602 to be relative to the first interactive element 604 on the first part 601 in a case where the first part 601 and the second part 602 are connected or otherwise operatively engaged and the first part 601 and the second part 602 are properly aligned. Accordingly, the first interactive element 604 and the second interactive element 606 may be aligned. As such, the first interactive element 604 and the second interactive element 606, for example, may interact with each other in a case where the first part 601 and the second part 602 are connected or otherwise operatively engaged and the first interactive element 604 and the second interactive element 606 are properly aligned.

An interaction between the first interactive element 604 and the second interactive element 606 (or between any other interactive element discussed in the disclosure) may occur in a case where the first part 601 and the second part 602 are operatively engaged properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first part 601 and the second part 602 for operation. It should be understood that with respect to the embodiments described in the disclosure, operatively engaged may include connected and/or aligned, unless otherwise specified. Likewise, operatively engaged (and/or connected and/or aligned) may include operatively engaged properly (and/or connected properly and/or aligned properly), unless otherwise specified.

In various embodiments, the first interactive element 604 and the second interactive element 606 may be similar types of devices. For instance, in some embodiments, the first interactive element 604 may be configured to interact with one or more second interactive elements and/or the second interactive element 606 may be configured to interact with one or more first interactive elements. For example, a first interactive element 604 may be a magnet arranged to provide an N (north) polarity and a second interactive element 606 may be a magnet arranged to provide an S (south) polarity. As such, the first interactive element 604 having the N polarity may interact more effectively (e.g., connect and/or align) with the second interactive element 606 having the S polarity than with another first interactive element 604 arranged to provide an N polarity.

In some embodiments, the first interactive element 604 and the second interactive element 606 may be dissimilar types of mechanisms. For example, a first interactive element 604 may be a ferrous conduit (or other magnetically attractive material) and a second interactive element 606 may be a magnet. The second interactive element 606 may interact with (e.g., connect and/or align) the first interactive element 604, as well as other magnetic second interactive elements 606 when the connected or otherwise brought together along the line A1 to put the first part 601 and the second part 602 in the first position P 1. As another example, for example with reference to FIGS. 15A and 15B, a first interactive element (e.g., 104 in FIGS. 15A-15B) may be a protrusion, pusher, finger, or other structural feature configured and/or arranged to act upon (e.g., urge) a second interactive element (e.g., 106' in FIGS. 15A-15B), and/or the like that may be for interacting with (e.g., functioning as a conductor for) another second interactive element (e.g., 106 in FIGS. 15A-15B).

Returning to FIGS. 46A-47C, in some embodiments, suitable electronics may be connected to the first interactive element 604 and/or the second interactive element 606 to provide a controlled power signal to selectively activate or otherwise control one or more of the first interactive element 604 and the second interactive element 606 and/or other components as described in the disclosure.

In various embodiments, some or all of the interactive elements (e.g., first interactive element 604, second interactive element 606) may be integrated with the first part 601 and the second part 602 and/or be separate components placed in or on the first part 601 and the second part. For example, the interactive elements may be placed in or on the first part 601 and the second part 602 in a friction-fitting manner, during a molding a process, and/or the like (e.g., magnetizing a suitable portion of the first part 601 and/or the second part 602). In some embodiments, one or more of the interactive elements may be insert mold labeled on its respective part. In some embodiments, a film cover may be provided for supporting one or more of the interactive elements.

In various embodiments, some or all of the interactive elements may have an exposed surface. The exposed surface of the interactive elements may be for allowing increased interactivity between each of the interactive elements, for example to allow a user to locate the interactive elements (e.g., to facilitate connection of the first part 601 and the second part 602), and/or the like. In other embodiments, some or all of the interactive elements may be covered, for example (but not limited to) being disposed completely within the first part 601 and/or the second part 602. Such embodiments may allow for protecting the interactive elements from damage, debris collection, mitigating interference with other components (e.g., other interactive elements, electronics in the medical device system 600, and/or the like), and/or the like.

In various embodiments, the first interactive element 604 and the second interactive element 606 may be properly aligned such as, but not limited to, when the first interactive element 604 and the second interactive element 606 align in one dimension (e.g., along the line A1) or more than one dimension, are sufficiently proximate to each other, contact each other, an electrical or magnetic connection is established between the components, and/or the like. Any one or combination of these events may occur, for example, in a case where the first part 601 and the second part 602 are operatively engaged and positioned relative to each other in a predetermined manner. In other words, the first part 601 and the second part 602 have been connected sufficiently proper and/or otherwise within an operating threshold.

In other embodiments, the first interactive element 604 may be arranged on the first part 601 at a location to interact electronically (or magnetically) with the second interactive element 606 in a case where the first part 601 and the second part 602 are brought together (e.g., at the first position P1) and the first interactive element 604 and the second interactive element 606 are in relative close proximity to each other, such as, but not limited to, in contact with each other. In some embodiments, suitable electronics may be connected to at least one of the first interactive element 604 and the second interactive element 606 to provide a controlled power signal to selectively activate or otherwise control the first interactive element 604 and/or the second interactive element 606.

In some embodiments, multiple pairs of first interactive elements and second interactive elements may be provided on the first part 601 and the second part 602, for example, to provide a more reliable alignment between the first part 601 and the second part 602. An example of such a configuration is shown (but not limited to) FIG. 8. With reference to FIGS. 8 and 46A-47C, in such embodiments, a second pair of interactive elements including a first interactive element (e.g., 104' in FIG. 8) and a second interactive element (e.g., 106' in FIG. 8) are supported by the first part 601 and the second part 602 respectively in a manner similar to that described above for the first interactive element 604 and the second interactive element 606. In further embodiments, more than two pairs of interactive elements may be supported by the first part 601 and the second part 602, as previously described.

In various embodiments, the first interactive element 604 and the first interactive element 104' (and/or the second interactive element 606 and the second interactive element 106') may be dissimilar from each. For instance, in some embodiments, the first interactive element 604 may be configured to interact with second interactive elements (e.g., the second interactive element 606) and/or the first interactive element 104' may be configured to interact with second interactive elements (e.g., the second interactive element 106'). For example, a first interactive element 604 may be a magnet arranged to provide an N (north) polarity and a second interactive element 606 may be a magnet arranged to provide an S (south) polarity. A first interactive element 104' may be a magnet arranged to provide an S (south) polarity and a second interactive element 106' may be a magnet arranged to provide an N (north) polarity. Thus, the first interactive element 604 having the N polarity may interact in a more mutually attracting manner (e.g., to connect and/or align) with the second interactive element 606 having the S polarity than the second interactive element 106' having the N polarity. Similarly, the first interactive element 104' having the S polarity may interact in a more mutually attracting manner (e.g., to connect and/or align) with the second interactive element 106' having the N polarity than the second interactive element 606 having the S polarity.

In some embodiments, the first interactive element 604 and the first interactive element 104' and/or the second interactive element 606 and the second interactive element 106' may be dissimilar types of mechanisms. For example, as described with respect to, for example FIGS. 15A and 15B, a first interactive element (e.g., 104 in FIGS. 15A-15B) may be a protrusion, pusher, finger, or other structural feature configured and/or arranged to act upon (e.g., urge) a second interactive element (e.g., 106' in FIGS. 15A-15B) and/or the like arranged and/or configured to interact with (e.g., function as a conductive medium) a second interactive element (e.g., 106 in FIGS. 15A-15B).

Returning to FIGS. 46A-47C, in particular embodiments, the interactive elements (e.g., 604, 606, and/or the like) may align the first part 601 and the second part 602 at the first position through magnetism. For instance, the first interactive element 604 may be a magnet provided on the first part 601. The second interactive element 606 may be a magnetically attractive material, such as a magnet of opposite polarity, a metal, and/or the like provided on the second part 602. Such an example as well as other examples are disclosed in, but are not limited to, U.S. patent application Ser. No. 11/759,725, entitled "Infusion Medium Delivery Device and Method with Drive Device for Driving Plunger in Reservoir," herein incorporated by reference in its entirety. As such, when the user-patient brings the first part 601 and the second part 602 sufficiently close together in the direction A1, the first interactive element 604 and the second interactive element 606 will interact with each other by attracting each other. Continued movement of the first part 601 and the second part 602 (by the user-patient and/or through the magnetic attraction of the first interactive element 604 and the second interactive element 606) in the direction A1 will properly align the first part 601 and the second part 602 at the first position P1.

Thus in various embodiments, as part of a process of assembling a first part 601 and a second part 602 of a medical device system 600, a user may bring the first part 601 and the second part 602 together along the direction A1 to operatively engage each other or otherwise be in sufficiently close proximity at the first position P1. Accordingly, a first interactive element 604 and a second interactive element 606 (and/or other interactive elements) may interact with each other to align the first part 601 and the second part 602 and/or to determine, for example, whether the first part 601 and the second part 602 have been properly aligned.

As such, in various embodiments, the interactive elements (e.g., first interactive element 604, second interactive element 606, and/or the like) may be configured to help a user-patient align the first part 601 and the second part 602 relative to each other for proper connection. For example, one or more pairs of interactive element 604, 606, and/or the like may be arranged at one or more appropriate locations on the first part 601 and the second part 602 to allow an indicator or indicator device 420 (e.g., FIG. 48) associated with the medical device system 600 to provide an indication that the first part 601 and the second part 602 are properly aligned in one or more dimensions relative to each other. Alternatively or in addition, one or more pairs of interactive element 604, 606, and/or the like may be of suitable size(s), shape(s), orientation(s), and position(s) to allow an indicator associated with the medical device system 600 to provide an indication that the first part 601 and the second part 602 are properly aligned in one or more dimensions relative to each other. For example, the indicator may provide an indication that the first part 601 and the second part 602 are properly aligned at the first position P1 in a case where the first interactive element 604 and the second interactive element 606 interact.

In some embodiments, a conductive medium (e.g., 108 in FIG. 9) may be at a position adjacent one of the interactive element(s) (e.g., the second interactive element 606) or otherwise in communication with the interactive element to allow the conductive medium 108 to function as a conductor for the interactive element. An example of such a configuration is shown in (but not limited to) FIG. 9. With reference to FIGS. 9 and 46A-47C, in such embodiments, the interactive element may interact with the conductive medium 108 to allow the conductive medium 108 to be have similar characteristics or properties, though not necessarily exactly the same characteristics or properties. For example, a magnetic second interactive element 606 may provide a magnetic charge to a magnetic conductive medium 108 to allow the first interactive element 604 to interact with the magnetic conductive medium 108. The conductive medium 108 may be made of a material, such as, but not limited to, an electrically conductive material (e.g., metal, graphite, salt solutions, plasma, and/or the like), a magnetically attractive material (e.g., metal), and/or the like. In some embodiments, the conductive medium 108 may be a sufficiently high thermally conductive material (e.g., metal, or any other material with a thermal conductivity, for example (but not limited to), above 1), and/or the like.

In further embodiments, the conductive medium 108 may be arranged on its respective part (e.g., the second part 602) to allow the interactive element (e.g., the second interactive element 606) interact with the other interactive element (e.g., the first interactive element 604) on the opposing part (e.g., the first part 601) via the conductive medium 108 in any of the manners described in the disclosure. For example, in particular embodiments, the first interactive element 604 may interact with the conductive medium 108 in a case where the first part 601 and the second part 602 are brought together generally along the line A1. Accordingly, the first interactive element 604 and the second interactive element 606 may be interactable with each other via the conductive medium 108. Thus, some embodiments may allow the first interactive element 604 to interact with the conductive medium 108 in addition to or alternative to the second interactive element 606. For example, a magnetic second interactive element 606 having a N (North) polarity may magnetize a magnetically attractive conductive medium 108, which may then interact with a first interactive element 604 having a S (South) polarity when the first part 601 and the second part 602 are brought together (e.g., along the line A1) to align the first part 601 and the second part 602.

In some embodiments, the conductive medium 108 may be arranged at a position adjacent the other interactive element (e.g., the first interactive element 604) or otherwise in communication with the other interactive element to allow the conductive medium 108 to function as a conductor for the other interactive element. In further embodiments, the conductive medium 108 may be arranged on its respective part to allow the other interactive element to interact with the interactive element (e.g., the second interactive element 606) on the opposing part via the conductive medium 108 in any of the manners described in the disclosure. For example, in particular embodiments, the second interactive element 606 may interact with the conductive medium 108 in a case where the first part 601 and the second part 602 are brought together (e.g., along the line A1). Accordingly, the first interactive element 604 and the second interactive element 606 may interact with each other via the conductive medium 108. Thus, some embodiments may allow for the second interactive element 606 to interact with the conductive medium 108 in addition to or alternative to the first interactive element 606. For example, an electrical connection between the first interactive element 604 and the second interactive element 606 may be established by contacting the conductive medium 108 (e.g., electrically conductive medium).

In some embodiments, the indicator may be configured to provide an indication corresponding to a type of alignment, for example, that a maximum alignment or a minimum required alignment has been achieved between the first interactive element 604 and the second interactive element 606 during connection of the first part 601 and the second part 602. In some embodiments, the indicator may be configured to provide an indication corresponding to various stages of alignment, for example, no alignment, alignment in one or more axes and misalignment in one or axes, complete alignment, and/or misalignment after alignment, and/or the like.

In various embodiments, additional structural features may be provided on one or both of the first part 601 and the second part 602 to provide a mechanical alignment function when the first part 601 and the second part 602 are brought together along the line A1. Such additional structural features may include a first sloped surface (e.g., 101a in FIGS. 7-11) on the first part 601 arranged to mate or otherwise engage a corresponding sloped surface (e.g., 102a in FIGS. 7-11) on the second part 602. As the first part 601 and the second part 602 are brought together generally along the line A1, a misalignment of the first part 601 and the second part may result in the first sloped surface 101a and the second sloped surface 102a engaging each other to align the first part 601 and the second part 602 with continued relative motion of the parts. Accordingly, the first sloped surface 101a and the second sloped surface 102a may engage each other in a position at which the first sloped surface 101a and the second sloped surface 102a may slide relative to each other toward a proper alignment position, for example, at the first position P1.

In some embodiments, multiple pairs of sloped surfaces may be provided on the first part 601 and the second part 602, for example, to provide alignment in one or more directions and/or one or more dimensions. For example, in some embodiments, the first part 601 and the second part 602 may include a second pair of sloped surfaces including a first sloped surface (e.g., 101b in FIG. 8) and a second sloped surface (e.g., 102b in FIG. 8) in a manner similar to that described above for the first sloped surface 101a and the second sloped surface 102a. The second pair of sloped surfaces may have a similar or different size and/or shape than the first pair of sloped surfaces 101a, 102a.

In some embodiments, (such as the embodiments exemplified in FIGS. 10A and 10B) at least one of the first part 601 and the second part 602 may include one or more sloped surfaces arranged to mate with corresponding sloped surfaces on the other of the first part 601 and the second part 602. In such embodiments, at least one of the one or more sloped surfaces may be mated with one or more of the plurality of corresponding sloped surfaces so that the first part 601 and the second part 602 can be aligned and/or connected in multiple orientations.

In further embodiments, some or all of the interacting components, such as the first interactive element 604 and the second interactive element 606, may be arranged along the first part 601 and the second part 602 to allow the first part 601 and the second part 602 to be connected and/or aligned in multiple orientations. An example of such a configuration is shown in (but not limited to) FIGS. 10A and 10B. With reference to FIGS. 10A-10B and 46A-47C, in such embodiments, the second part 602 may include multiple sets of second interactive elements 606 and 106', thus allowing the first interactive element 604 to be selectively aligned with any of the second interactive elements 606 while allowing the first interactive element 104' to be aligned with at least one of the second interactive elements 106'. As such, the first part 601 and the second part 602 can be aligned and/or connected in at least a first orientation (e.g., FIG. 10A) and a second orientation (e.g., FIG. 10B). The first orientation, for instance, may correspond to the first position P. The second orientation may correspond to a different first position. As another example, the first part 601 may include multiple sets of first interactive elements 606 and multiple sets of first interactive elements 104' for allowing selective alignment with the second interactive element 606 and the second interactive element 106', respectively.

Returning to FIGS. 46A-47C, in some embodiments, the interactive elements (e.g., first interactive element 604, second interactive element 606, and/or the like) may be supported and/or be part of the sloped surfaces 101a, 102a to provide an alignment and connection function as described in the disclosure. An example of such a configuration is shown in (but not limited to) FIG. 11. With reference to 46A-47C, various embodiments may additionally or alternatively include other suitable structural features to aid in the alignment, including, but not limited to, curved or stepped surfaces, rollers and/or the like on the first part 601 and the second part 602 that abut as the first part 601 and the second part 602 are brought together to align the parts.

In some embodiments, one or both of the first interactive element 604 and the second interactive element 606 may have a mating, sloped, or otherwise shaped surface for engaging and providing an alignment function when the first part 601 and the second part 602 are brought together for connection. For example, with reference to FIGS. 12 and 46A-47C, the first interactive element 604 may have a sloped surface adapted to be mated with a corresponding sloped surface of the second interactive element 606 (or the part supporting the second interactive element) in a manner similar to that described with respect to the first sloped surface 101*a* (e.g., FIGS. 7-11) and the second sloped surface 102*a* (e.g., FIGS. 7-11). In further embodiments, one or both of the first part 601 and the second part 602 may include sloped surfaces 601*a*, 102*a* for mating with interactive elements (e.g., first interactive element 604, second interactive element 606) having appropriately shaped surfaces similar to that previously described. An example of such a configuration is shown in (but not limited to) FIG. 13.

Returning to FIGS. 46A-47C, in various embodiments, the interactive elements (e.g., first interactive element 604, second interactive element 606, and/or the like) may allow for, but is not limited to, tracking a number of times a component has been connected to and/or disconnected from other components, verifying proper connection and/or alignment of components in a medication delivery system prior to each delivery step, checking, sensing, and/or measuring parameters, such as ambient parameters (e.g., ambient magnetic fields), operating parameters, and/or the like, alerting users to conditions, such as conditions outside operating parameters of the delivery system, and/or the like.

Various embodiments may employ different arrangements of interactive elements on the first part 601 and/or the second part 602. For instance, in embodiments in which one of the first part 601 and the second part 602 is intended to be disposable (e.g., disposed of after one or a prescribed number of uses or period of use), some of the interactive elements may be provided on the disposable part, while other interactive elements may be provided on a durable part (i.e., not intended to be disposed). As a result, after a period of usage, the interactive element(s) on the disposable part that may have attracted and collected stray material can be disposed of with the disposable part.

On the other hand, the interactive element(s) on the durable part can be sufficiently clean and free (or be cleaned) of stray material for further usage. In such embodiments, arranging at least some of the interactive element(s) on the durable portion may provide certain advantages, such as, but not limited to, being more cost-effective, for example, by arranging interactive elements on respective parts based on cost; easier to manufacture and/or install, and/or the like. For example, electronics and circuitry, such as, but not limited to, a sensor (e.g., FIGS. 16-23), a responsive device (e.g., FIGS. 24-29B and 48), and/or other circuitry or electronics, may be arranged on the durable part.

In yet other embodiments, arranging at least some of the interactive element(s) on the disposable portion may provide certain advantages, such as, but not limited to, maintenance, cost, and/or the like. For example, such embodiments may allow for the interactive element(s) that have worn down, been contaminated, or otherwise collected stray material to be disposed of with the disposable part.

Thus in various embodiments, as part of a process of assembling a first part 601 and a second part 602 of a medical device system 600, a user may bring the first part 601 and the second part 602 together along the direction A1 to operatively engage each other or otherwise be in sufficiently close proximity at the first position P1. Accordingly, a first interactive element 604 and a second interactive element 606 (and/or other interactive elements) may interact with each other to align the first part 601 and the second part 602 and/or to determine, for example, whether the first part 601 and the second part 602 have been properly aligned, as shown for example in FIGS. 46B and 47B.

Once the first part 601 and the second part 602 are connected or otherwise aligned at the first position P1, the first part 601 and the second part 602 are configured to engage each other by moving relative to each other, for instance in the direction A2, to the second position P2. For instance, the second part 602 may be configured to engage the first part 601 by sliding the second part 602 in the direction A2 to the second position P2, as shown for example in FIGS. 46C and 47C.

Movement of the second part 602 in the direction A2 from the first position to the second position P2 causes the misalignment of the first interactive element 604 and the second part 602 in the direction A2. Thus, in further embodiments, in a case where the alignment of the first interactive element 604 and the second interactive element 606 is accomplished via magnetism, the magnet strength used should be selected to allow properly alignment as the first part 601 and the second part 602 are brought together in the direction A1, yet allow the magnets to be misaligned when the user pushes or slides the second part 602 in the direction A2. For instance, the attraction between the first interactive element 604 and the second interactive element 606 should be sufficient to allow proper alignment, yet allow a user to separate the elements when moving in the direction A2.

In various embodiments, the first position P1 (i.e., the position at which the first interactive element 604 and the second part 602 interact to indicate that the first part 601 and the second part 602 are in proper alignment when brought together in the direction A1) may correspond to a location on the first part 601 where movement of the second part 602 in the direction A2 is guided so that alignment of the first part 601 and the second part 602 is maintained (e.g., at least in a direction transverse to the direction A1 and A2). For instance, one or more rails 659, ridges, other raised surfaces, or guiding structures, for example as discussed in (but not limited to) the disclosure, may be arranged on the first part 601 (and/or the second part 602) to be adjacent (or sufficiently close), for example to be in end-to-end contact with the second part 602, to the second part 602 (and/or the first part 601) when the second part 602 is at the first position P1 to allow the second part 602 to be moved in the direction A2 (e.g., along a length dimension of the first part 601) without being misaligned laterally (e.g., relative to a width dimension of the first part 601). In other embodiments, the second part 602 need not be adjacent the rails 659 at the first position P1. In such embodiments, for instance, while at the first position, the second part 602 may be positioned in an opening 657 between tapered surfaces 659*a* (i.e., non-parallel to each other) or the like. Accordingly, when the second part 602 is moved generally in the direction A2, if the second part 602 is misaligned laterally (e.g., FIG. 38B), a portion of the second part 602 may contact at least one of the surfaces 659*a* to guide the second part 602 toward an aligned position in the lateral direction with continued movement of the second part 602 in the direction A2. Examples of various guiding structures are discussed in (but not limited to) FIGS. 30A-40B.

Returning to FIGS. 46A-47C, in some embodiments, a plurality of interactive elements may be provided along or near the direction A2 on one or both of the first part 601 and the second part 602 to allow certain interactive elements to interact depending on the relative location of the second part 602 to the first part 601. Such embodiments, for example, allow the user (e.g., through an associated indicator device) to determine whether the first part 601 and the second part 602 have completely engaged (e.g., the second part 602 has reached the second position P2), and/or otherwise determine the relative position of the second part 602. Examples of such arrangements, as well as other arrangements (e.g., using mylar films) for detecting the location of one component as it moves relative to another component, are disclosed in, but not limited to U.S. patent application Ser. No. 12/649,619, filed Dec. 30, 2009, which is herein incorporated by reference in its entirety.

In various further embodiments, the second part 602 may include an interactive element, for example, as described in the disclosure, for interacting with the first interactive element 604 when the first part 601 is moved to the second position P2, as shown in FIG. 46C. For instance, the second part 602 may include a third interactive element 606'. In some embodiments, the third interactive element 606' may be similar to the second interactive element 606. For instance, the second interactive element 606 and the third interactive element 606' are magnets such that the first interactive element 604 interacts (e.g., is magnetically attracted to, detects the magnetism of the second interactive element 606, etc.) with the second interactive element 606 at the first position P1 and interacts with the third interactive element 606' at the second position P2. In other embodiments, the third interactive element 606' may be similar to the second interactive element 606. For instance, the second interactive element 606 may be a magnet that is magnetically attracted to a magnetic first interactive element 604 to align the first part 601 and the second part 602 at the first position P1, and the third interactive element 606' may be a sensor configured to detect the magnetic first interactive element 604 when the first part 601 and the 602 are at the second position P2.

Thus, it should also be noted that the term interact may apply differently for various interactive elements. For example, a magnetic first interactive element 604 and a magnetic second interactive element 606 may interact via magnetic attraction between the two elements when aligning in the direction A1, and the first interactive element 604 may interact with the third interactive element 606' by configuring the third interactive element 606' to sense or otherwise detect the position of the first interactive element 604 when the first part 601 and the second part 602 are in the second position P2.

In further embodiments, the first part 601 may include an interactive element, for example, as described in the disclosure, for interacting with the second interactive element 606 when the first part 601 is moved to the second position P2, as shown in FIG. 46C. For instance, the second part 601 may include a fourth interactive element 604'. Accordingly, in some embodiments, when in the second position P2, there may be a first interaction between the first interactive element 604 and the third interactive element 606' and a second interaction between the fourth interactive element 604' and the second interactive element 606.

In particular embodiments, the various elements may be arranged at particular locations of the first part 601 and/or the second part 602 to increase alignment accuracy of particular components of the first part 601 and/or the second part 602. For instance, in some embodiments, the first interactive element 604 may be arranged on or near the fluid conduit (e.g., 524 in FIGS. 30A-31C) of the first part 601 and the second interactive element 606 may be arranged on or near the reservoir (e.g., connection portion 531 in FIGS. 30A-31C, septum within the reservoir, etc.). Thus, alignment of the fluid conduit relative to the reservoir can be determined.

Thus, in various embodiments, the medical device system 600 may include any one or combination of aligning structures, connecting structures, and detecting systems for detecting alignment and/or connection discussed in (but not limited to) the disclosure. For instance, in some embodiments, the medical device system 600 is configured to align and/or connect the first part 601 and the second part 602 at the first position P1 and to detect alignment and/or connection of the first part 601 and the second part 602 at the second position P2. In other embodiments, the medical device system 600 is configured to align and/or connect the first part 601 and the second part 602 at the first position P1 and to align and/or connect the first part 601 and the second part 602 at the second position P2 (or other desired position). In yet other embodiments, the medical device system 600 is configured to detect alignment and/or connection of the first part 601 and the second part 602 at the first position P1 and to detect alignment and/or connection of the first part 601 and the second part 602 at the second position P2 (or other desired position). In other further embodiments, the medical device system 600 is configured to detect alignment and/or connection of the first part 601 and the second part 602 at the first position P1 and to align and/or connect the first part 601 and the second part 602 at the second position P2 (or other desired position).

In further embodiments, multiple interactive elements may be employed to allow proper alignment, connection, and/or detection of such more than two stages. For example, the medical device system 600 may be configured to align and/or connect the first part 601 and the second part 602 at the first position P1, align and/or connect the first part 601 and the second part 602 at some point between the first position P1 and the second position P2 (e.g., FIG. 31B), and to detect alignment and/or connection of the first part 601 and the second part 602 at the second position P2 (e.g., FIG. 31C).

In further embodiments, the medical device system 600 may include more than two housing portions. For example, such embodiments may include, but are not limited to, a durable housing portion 30, a disposable housing portion 20, and a base portion 21 (refer to FIGS. 1-6C). Other housing portions may include, but are not limited to, an insertion device, electronics, and/or the like.

FIGS. 49 and 50A-59B illustrate a process S1000 for aligning and/or connecting a first housing portion 1001 (e.g., 101, 102, 201, 202, 301, 302, 303, 401, 402, 530, 550, 601, 602, 901, 902, 1101, 1102 in FIGS. 7-48), and a second housing portion 1002 (e.g., 101, 102, 201, 202, 301, 302, 303, 401, 402, 530, 550, 601, 602, 901, 902, 1101, 1102 in FIGS. 7-48) of a medical device system 1000 (e.g., 100, 200, 300, 400, 500, 600, 900, 1100 in FIGS. 7-48). In particular embodiments, the first housing portion 1001 may be a base portion (e.g., 21 in FIGS. 1-6C) and the second housing portion may be a durable portion (e.g., 30 in FIGS. 1-6C).

With reference to FIGS. 49-50B, according to various embodiments, the process S1000 is an engagement sequence for aligning and connecting the base portion 1001 to the durable portion 1002. In FIGS. 50A and 50B (which correspond to, for example (but not limited to), the embodiments relating to FIGS. 46A and 47A), the base portion 1001 and the durable portion 1002 are not connected.

Figure 46A:
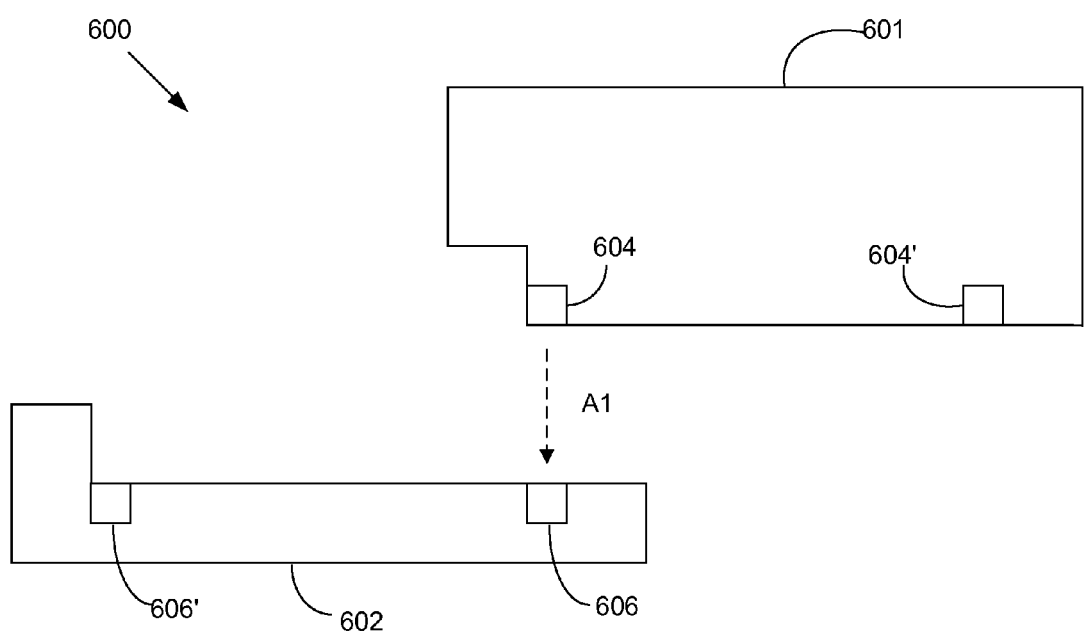
Figure 47A:
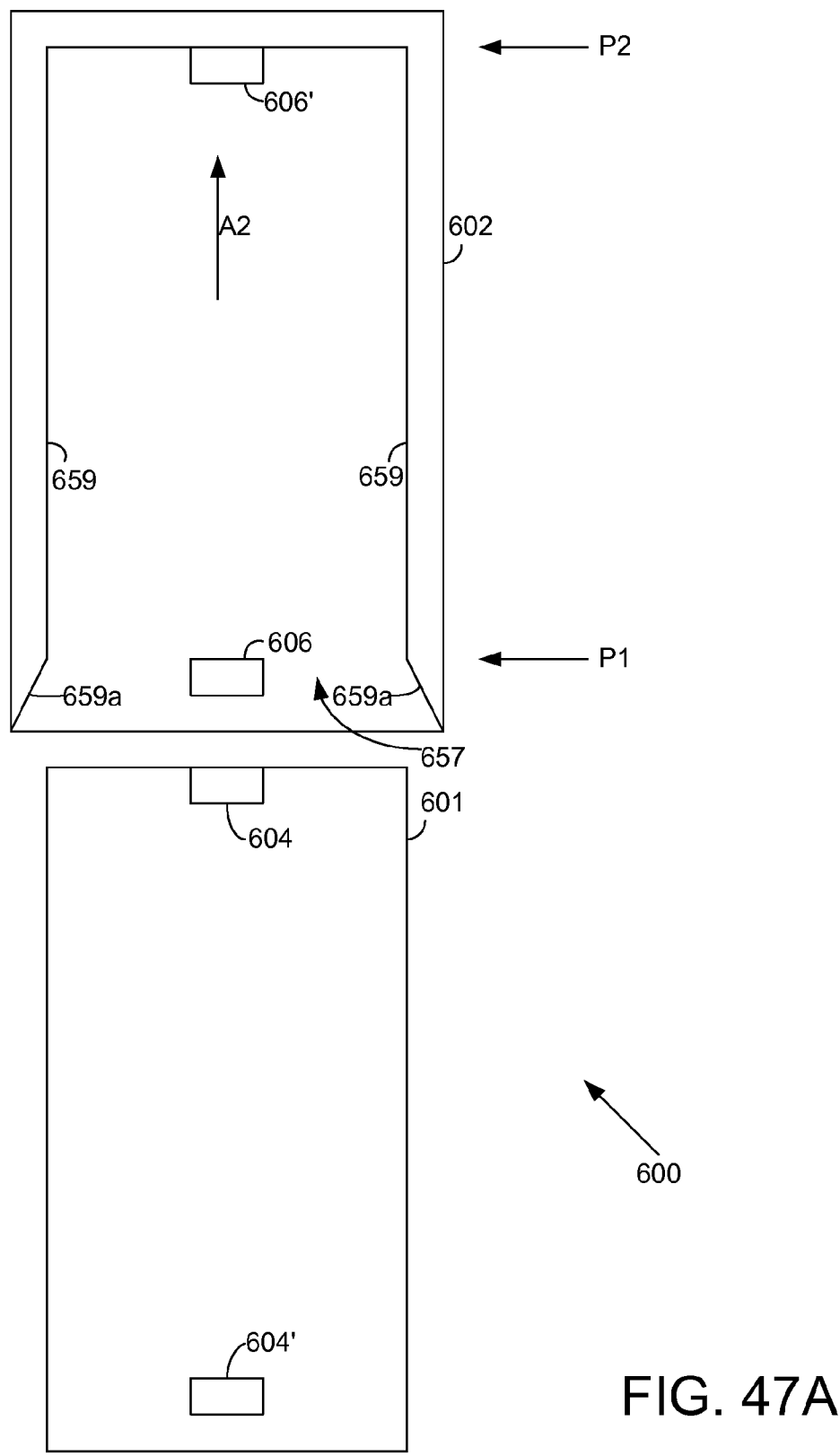
FIGS. 47A, 47B, and 47C illustrate a medical device system in accordance with an embodiment of the present invention.
Figure 47B:
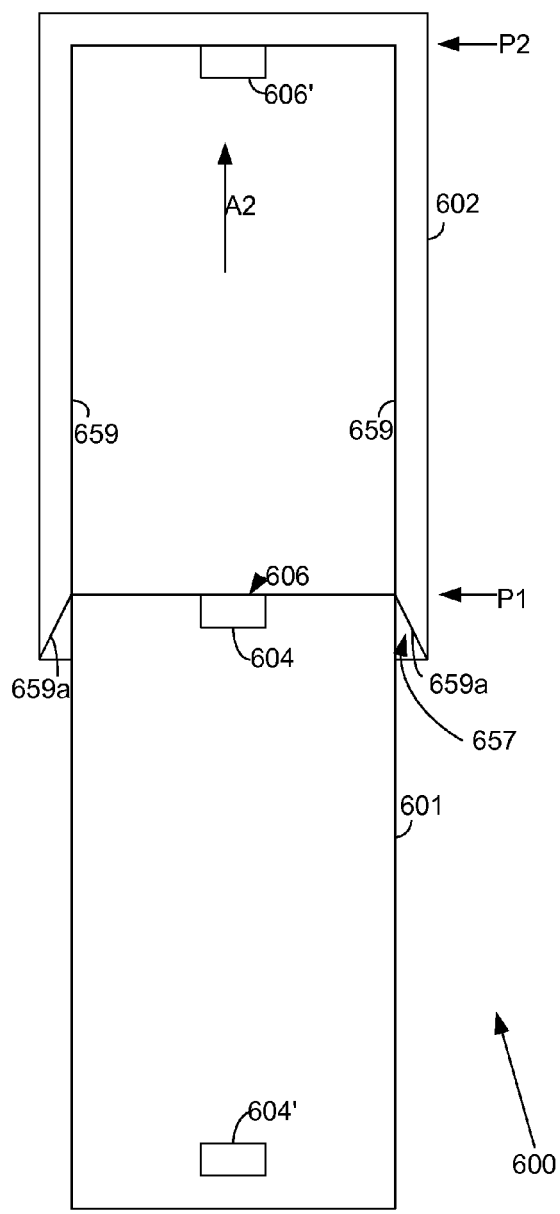
Figure 47C:
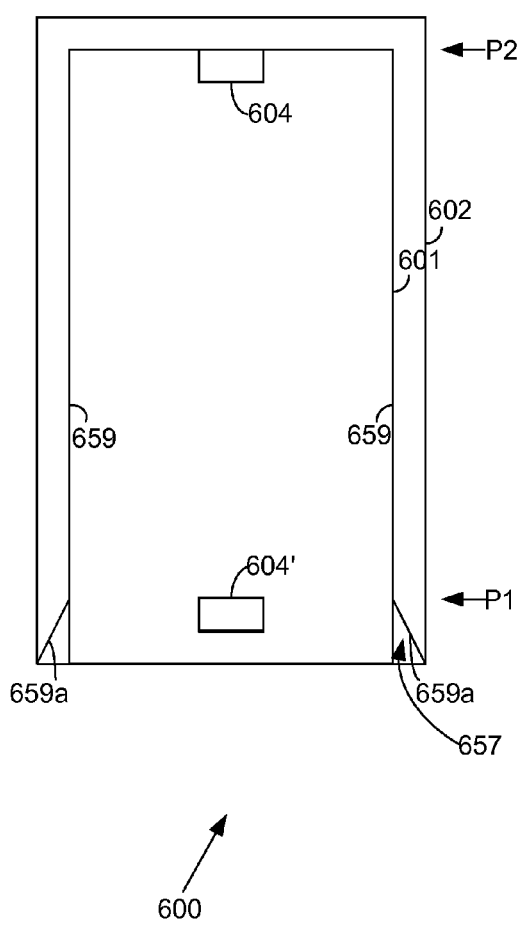

With reference to FIGS. 49, 51A, and 51B, in step S1005, a first interactive element 1004 (e.g., 104, 204, 304, 404, 504, 604, etc. in FIGS. 7-29A and 46A-47C) on the base portion 1001 may be aligned with a second interactive element 1006 (e.g., 106, 206, 306, 406, 506, 606, etc. in FIGS. 7-29A and 46A-47C) on the durable portion 1002 to provide initial coarse longitudinal alignment of the medical device system 1000, as shown in FIGS. 51A and 51B (which correspond to, for example (but not limited to), the embodiments relating to FIGS. 46B and 47B). For instance, the second interactive element 1006 may be a magnet and the first interactive element 1004 may be a yoke or metal for aligning with the magnet. In further embodiments, the base portion 1001 may include further interactive elements 1004' (e.g., 104' 204' 304' 404', 504' 604', etc. in FIGS. 7-29A and 46A-47C) for engaging further interactive elements 1006' (e.g., 106', 206', 306', 406', 506', 606', etc. in FIGS. 7-29A and 46A-47C) on the durable portion 1002. For instance, the further interactive element 1004' may be a magnet and the second interactive element 1006' may be a yoke or metal for aligning with said magnet. Once aligned, the durable portion 1002 may be brought toward the base portion 1001 along a direction A1. In particular embodiments, the alignment of one or more of the elements may be indicated by an indicator device, such as (but not limited to) the indicator 420 of FIG. 48.

With reference to FIGS. 49, 52A, and 52B, in step S1010, one or more rails 1059 (e.g., 559 in FIGS. 37A-38C), ridges, or other raised surfaces on the base portion 1001 may guide the durable portion 1002 as the durable portion 1002 is moved (relative to the base portion 1001) in a direction A2, as shown in FIGS. 52A and 52B (which correspond to, for example (but not limited to), the embodiments relating to FIGS. 37A-38C). Accordingly, in various embodiments, the rails 1059 may provide initial coarse horizontal alignment between the base portion 1001 and durable portion 1002 at a rear of medical device system 1000. In some embodiments, the durable portion 1002 may include arms 1037, wings, or the like for engaging the rails 1059 to provide coarse vertical alignment (and prevent the housing portions from separating in the vertical direction) between the base portion 1001 and the durable portion 1002 at the rear of the medical device system 1000 as the durable portion 1002 is moved in the direction A2 (relative to the base portion 1001).

Returning to FIGS. 49, 52A, and 52B, in some embodiments, in step S1015, at least one arm 1054 (e.g., 554 in FIGS. 37A-38C), rail, or other raised surface at or near a front end of the base portion 1001 may engage an arm 1032 (e.g., 532 in FIGS. 37A-38C) or the like at or on a front end of the durable portion 1002 to provide a coarse horizontal and/or vertical engagement of the base portion 1001 and the durable portion 1002 toward the front end of the medical device system 1000, as shown in FIGS. 52A and 52B (which correspond to, for example (but not limited to), the embodiments relating to FIGS. 37A-38C). In FIGS. 52A and 52B, steps S1010 and S1015 of FIG. 49 are shown as occurring substantially simultaneously. In other embodiments, step S1010 may occur before step S1015. In yet other embodiments, step S1015 may occur before step S1010. In some embodiments, one or more of steps S1010 and S1015 may be omitted.

With reference to FIGS. 49, 53A, and 53B, in step S1020, with continued movement in the direction A2, a needle 1024 (e.g., fluid conduit 524 in FIGS. 30B, 31A and 31B) in the base portion 1001 is aligned (e.g., longitudinally, horizontally, and/or vertically) with a reservoir (e.g., reservoir housing 508 in FIG. 30B) in the durable portion 1002 to allow the needle 1024 to enter the reservoir to form a fluid connection therebetween (step S1030), as shown in FIGS. 53A and 53B. Returning to FIGS. 49, 53A, and 53B, such embodiments may provide finer alignment than the coarse alignment of steps S1005-S1015. Examples of structures for guiding the needle 1024 and/or the reservoir toward each other to form a fluid connection therebetween is disclosed in (but not limited to) U.S. patent application Ser. No. 12/974,106, filed Dec. 21, 2010, and U.S. patent application Ser. No. 12/974,117, filed Dec. 21, 2010, both of which are herein incorporated by reference in their entirety.

With reference to FIGS. 49, 54A, and 54B, in step S1025, with continued movement in the direction A2, a latch 1038 on the durable portion 1002 contacts a catch 1067 (e.g., protrusion 567 in FIG. 33) of the base portion 1001, as shown in FIGS. 54A and 54B (which generally correspond to, for example (but not limited to), the embodiments relating to FIGS. 33 and 34). For example, in some embodiments, the latch 1038 may be a tab, protrusion, or the like. The latch 1038 may be flexible or supported on a portion of the durable portion 1002 that is flexible. The latch 1038 may be configured to engage a cavity 1068 (e.g., 568 in FIG. 33), engagement member, and/or the like in the base portion 1001 as the durable portion 1002 is moved in the direction A2 (relative to the base portion 1001). The catch 1067 may be arranged on the base portion 1001 to direct or flex the latch 1038 inwardly (or outwardly) as the durable portion 1002 moves (e.g., slides) in the direction A2. Continued movement of the durable portion 1002 in the direction A2 beyond the catch 1067 allows the latch 1038 to flex in the opposite direction into the cavity 1068 or an abutment or other engagement member in or defining the cavity 1068 of the base portion 1001.

In particular embodiments, the latch 1038 may be configured to force the base portion 1001 and the durable portion 1002 apart in a case where the base portion 1001 and the durable portion 1002 are not properly connected. For example, in a case where the durable portion 1002 is not slid a sufficient distance relative to the base portion 1001 (in the direction A2) so that the latch 1038 clears the catch 1067 and engages the cavity 1068, the latch 1038 is forced in the opposite direction (to the direction A2) to further separate the base portion 1001 and the durable portion 1002. Accordingly, one or more of the engagement steps (e.g., steps S1005-S1045) may be repeated until the latch 1038 clears the catch 1067 and engages the cavity 1068 (e.g., step S1050).

With reference to FIGS. 49, 55A, and 55B, in step S1030, with continued movement in the direction A2, a dovetail 1042 (e.g., 542 in FIGS. 35A-36B) of the durable portion 1002 engages a groove 1062 (e.g., 562 in FIGS. 35A-36B) in the base portion 1001 to provide fine vertical (and/or other) alignment between the base portion 1001 and the durable portion 1002 at the rear of the medical device system 1000, as shown for example in FIGS. 55A and 55B (which correspond to, for example (but not limited to), the embodiments relating to FIGS. 35A-36B). Such embodiments, for instance, may provide finer alignment than the coarse alignment of steps S1005-S1015 (FIG. 49).

With continued movement in the direction A2, in step S1035 (FIG. 49), the needle 1024 enters the reservoir supported by the durable portion 1002 to establish a fluid connection between the needle 1024 and an interior volume of the reservoir, as shown in FIGS. 56A and 56B.

With reference to FIGS. 49, 57A, and 57B, with continued movement in the direction A2, in step S1040, contacts 1010 (e.g., electrical contacts 910 in FIGS. 41A-43B) of the base portion 1001 may engage contacts 1020 (e.g., shorting mechanism 920 in FIGS. 41A-43B) of the durable portion 1002, which may indicate that the base portion 1001 and the durable portion 1002 have been sufficiently connected to form a fluid flow path therebetween, as shown in FIGS. 57A and 57B (which correspond to, for example (but not limited to), the embodiments relating to FIGS. 41A-43B).

Returning to FIGS. 49, 57A, and 57B, in step S1045, a sensor 1012 (e.g., 1110 in FIGS. 44A-45B) in the durable portion 1002 may detect a predetermined magnetic field, angle, gauss level, and/or the like provided by a magnetic source 1022 (e.g., 1120 in FIGS. 44A-45B) of the base portion 1001, which may indicate that the base portion 1001 and the durable portion 1002 have been sufficiently connected to form a fluid flow path therebetween, as shown in FIGS. 57A and 57B (which correspond, for example, to the embodiments relating to FIGS. 44A-45B). In some embodiments, a sensor (e.g., sensor 1012) is in the base portion 1001 to detect a predetermined magnetic field, angle, gauss level, and/or the like provided by a magnetic source (e.g., magnetic source 1022) in the durable portion 1002. In particular embodiments, the magnetic source may be one of the elements used to align the base portion 1001 and the durable portion 1002 (e.g., step S1005).

In FIGS. 57A and 57B, steps S1040 and S1045 of FIG. 49 are shown as occurring substantially simultaneously. In other embodiments, step S1045 may occur before step S1040. In yet other embodiments, step S1040 may occur before step S1045. In some embodiments, one or more of steps S1040 and S1045 may be omitted.

With reference to FIGS. 49, 58A, and 58B, with continued movement in the direction A2, in step S1050, the latch 1038 clears the catch 1067 and engages the cavity 1068 (or the like), as shown in FIGS. 58A, and 58B. In various embodiments, the catch 1067 biases the latch 1038 and the durable portion 1002 toward the front end of the base portion 1001. In particular embodiments, the engaging of the latch 1038 with the cavity 1068 may provide audile feedback to the user to indicate a proper connection. Other suitable methods for detecting that the latch 1038 is engaged in the cavity 1068 may also be used (e.g., detecting the presence of the latch 1038 with a sensor, or the like). In particular embodiments, the engagement of the latch and the catch 1067 and/or detection thereof may be indicated by an indicator device, such as (but not limited to) the indicator 420 of FIG. 48.

With reference to FIGS. 49, 59A, and 59B, with continued movement in the direction A2, in step S1055, a stopping surface 1036 (e.g., 536 in FIGS. 30C, 31C, and 32C) of the durable portion 1002 contacts a stopping surface 1056 (e.g., 556 in FIGS. 30C, 31C, and 32C) of the base portion 1001 to prevent further movement of the durable portion 1002 in the direction A2 (relative to the base portion 1001), as shown in FIGS. 59A and 59B (which correspond to, for example (but not limited to), the embodiments relating to FIGS. 30C, 31C, 32C, 46C, and 47C). Such embodiments may allow for additional protection of components of the durable portion 1002 (e.g., the reservoir) and/or the base portion 1002 (e.g., the fluid conduit 1024) from damage due to excessive force, speed, and/or the like in connecting the base portion 1001 and the durable portion 1002.

With reference to FIGS. 49-59B, the various components and features described as being on or part of the base portion 1001 and the various components and features described as being on or part of the durable portion 1002 are merely exemplary. In other embodiments, some or all of the various components and features described as being on or part of the base portion 1001 may be (in addition to or in alternative of) on or part of the durable portion 1002. Likewise, in other embodiments, some or all of the various components and features described as being (in addition to or in alternative of) on or part of the durable portion 1002 may be on or part of the base portion 1001. For instance, a dovetail 1042 may be arranged on the base portion 1001 to be received in a groove 1062 on the durable portion 1002. As another example, a first groove may be provided on the base portion 1001 to receive a first dovetail on the durable portion 1002, and a second groove may be provided on the durable portion 1002 to receive a second dovetail on the base portion 1001.

In various embodiments, one or more of the various components and features of the base portion 1001 and/or the durable portion 1002 may be omitted. For instance, in some embodiments, the sensor 1012 and the magnetic source 1022 may be omitted. In such embodiments, for example, fluid flow presence may be detected or otherwise determined via engagement of the contacts 1010 and the contacts 1020 alone and/or other suitable detection methods.

It should be noted that the process S1000 is not limited to any one or combination of the steps S1005-S1055 are merely exemplary, as some embodiments may omit some steps and/or include additional steps. Likewise, the order of the process S1000 is not limited to any particular order (e.g., FIG. 49). In other embodiments, the steps may be performed in any suitable order. For example, step S1030 (i.e., the dovetail 1042 engaging the groove 1062) may occur before step S1020 (i.e., aligning the needle 1024 with the reservoir). In particular embodiments, some of the steps of the process S1000 may occur substantially simultaneously. For example, steps S1040 (i.e., the contacts 1010 engaging the contacts 1020) and S1045 (i.e., the sensor 1012 detecting the magnetic source 1022).

In further embodiments, the medical device system 1000 may include more than two housing portions. For example, such embodiments may include, but are not limited to, a durable housing portion 30, a disposable housing portion 20, and a base portion 21 (refer to FIGS. 1-6C). Other housing portions may include, but are not limited to, an insertion device, electronics, and/or the like.

With reference to FIGS. 7-59B, while particular embodiments of the present invention have been shown and described, it will be apparent to those skilled in the art that the invention is not limited to the particular embodiments shown and described and that changes and modifications may be made without departing from the spirit and scope of the claimed invention. For example, while embodiments described above may include an adhesive material and a cover film 23 (FIGS. 2 and 3), further embodiments may include a plurality of adhesive material layers alternating with a corresponding plurality of cover film layers 23 to allow the delivery device to be secured, removed and re-secured to the skin of the patient-user one or more times.

In such embodiments, a first cover film layer located at the end of the stack of alternating layers of adhesive material and cover film may be removed to expose a first layer of adhesive material. With the first layer of adhesive material exposed, a medical device system (e.g., 100) (or component thereof) may be adhered to skin of a patient-user, as previously described. After a suitable period of usage, the medical device system (or component having the adhesive) may be removed from the skin of the patient-user, for example, for servicing, re-filling, replacement of one or more components, or the like. After removal of the medical device system (or component) from the skin of the patient-user, a second cover film layer on the medical device system (or component) may be removed to expose a second layer of adhesive material. With the second layer of adhesive material exposed, the medical device system (or component) may be secured to the same patient-user or, in certain contexts, to a different patient-user, for further operation. The process may be repeated a number of times up to the number of adhesive material and cover film layer pairs are included in the plural alternating layers of adhesive material and cover film.

In addition, while various embodiments described above may include one or more adhesive layers, each having a peelable cover layer, other embodiments may employ a single adhesive layer having (or plural adhesive layers, each having) a pattern of plural peelable cover layer portions. Accordingly, a patient-user may peel off one portion of the cover layer for adhering a medical device system (e.g., 100) to the patient-user as described above, while leaving the rest of the pattern of peelable cover layer portions on the adhesive. In such an embodiment, after completion of a first period of operation of the medical device system and removal of the medical device system from the patient-user, a second portion of the peelable cover layer may be removed from the adhesive layer and the medical device system may be adhered to the same patient-user or, in certain contents, to a different patient-user for a second period of operation.

In various embodiments, while various medical device system (e.g., 100) embodiments described above may include base portions (e.g., 21 in FIGS. 1-6C) that are configured to be secured to skin of a patient-user (or other suitable surface of operation) and that extend along a length and/or width of the medical device system structure, other embodiments may employ base portions configured to be secured to the skin of the patient-user (or other surface) and extend less than a full length or width dimension of the medical device system structure to minimize surface area in contact with the patient-user (or other surface). Such embodiments may increase comfort of the patient-user during operation of the medical device system. Base portions having shapes and sizes different from those shown in the accompanying drawings may be employed for additional improvements with regard to the comfort of the patient-user and/or minimizing the surface area in contact with the patient-user. Furthermore, as noted above, the base portion may be composed of a flexible material that at least partially conforms to the curvature and movement of a body of the patient-user.

In any of the above-described embodiments in which an adhesive material is used to secure one or more medical device system (e.g., 100) components to skin of a patient-user (or other suitable surface), multiple types of adhesive materials (or multiple strengths of adhesives) may be employed, such that a stronger adhesive may be provided in certain areas (e.g., around the needle injection site), while a weaker adhesive may be provided in other areas. Examples of various adhesive systems may be found in, but are not limited to, U.S. application Ser. No. 12/027,963, filed Feb. 7, 2008, entitled "Adhesive Patch Systems and Methods," herein incorporated by reference in its entirety.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A medical device for treating a user, the device comprising:
   a first housing portion adapted to be carried by a user;
   a second housing portion configured to be selectively operatively engaged with and disengaged from the first housing portion, the first housing portion and the second housing portion configured to be movable relative to each other from a first position to a second position in a predefined direction to operatively engage each other at the second position;
   a first interactive element supported on the first housing portion;
   a second interactive element supported on the second housing portion in a position to interact with the first interactive element when the first housing portion and the second housing portion are in the first position;
   a third interactive element supported on the second housing portion in a position to interact with the first interactive element when the first housing portion and the second housing portion are in the second position, wherein the second interactive element and the third interactive element are arranged relative to each other along the predefined direction and spaced apart from each other in the predefined direction;
   at least one guiding structure arranged on the second portion configured to guide movement of the first portion or the second portion from the first position to the second position; and
   electronic circuitry configured to detect at least one of a first interaction between the first interactive element and the second interactive element, and a second interaction between the first interactive element and the third interactive element, the circuitry configured to provide a signal or a change in state in response to detection of at least one of the first interaction and the second interaction.

2. The device according to claim 1, the device further comprising:
   a user-perceptible indicator operatively coupled to the electronic circuitry for providing a user-perceptible indication in response to the signal or the change in state.

3. The device according to claim 2, wherein the user-perceptible indication comprises at least one of an audible indication, a visual indication, and a tactile indication.

4. The device according to claim 1,
   the first interactive element having a detectable parameter;
   one or more of the second interactive element and the third interactive element comprising a sensor for detecting the parameter;
   wherein the electronic circuitry is configured to provide the signal or the change in state in a case where the sensor detects a level of the parameter equal or exceeding a specified level.

5. The device according to claim 4, wherein the electronic circuitry is configured to provide a different signal in a case where the sensor detects a level of the parameter less than the specified level.

6. The device according to claim 1,
   one or more of the second interactive element and the third interactive element having a detectable parameter;
   the first interactive element comprising a sensor for detecting the parameter;
   wherein the electronic circuitry is configured to provide the signal or the change in state in a case where the sensor detects a level of the parameter equal or exceeding a specified level.

7. The device according to claim 6, wherein the electronic circuitry is configured to provide a different signal in a case where the sensor detects a level of the parameter less than the specified level.

8. The device according to claim 1, wherein the first housing portion and the second housing portion are configured to be in the second position when the first housing portion and the second housing portion are positioned relative to each other in a predetermined manner.

9. The device according to claim 1, wherein the first housing portion and the second housing portion are configured to be in the second position when the first interactive element and the third interactive element are sufficiently proximate to each other to interact with each other.

10. The device according to claim 9, wherein the first interactive element and the third interactive element are sufficiently proximate to each other to interact with each other in a case where one or more of the first interactive element and the third interactive element contact each other, the first interactive element and the third interactive element are adjacent each other, and the first interactive element and the third interactive element are within a predetermined distance of each other.

11. The device of claim 1, further comprising:
a fourth interactive element supported on the first housing portion in a position to interact with the second interactive element when the first housing portion and the second housing portion are in the second position;
wherein the electronic circuitry is configured to detect the second interaction between the first interactive element and the third interactive element and a third interaction between the fourth interactive element and the second interactive element; and
wherein the electronic circuitry is configured to provide the signal or the change in state in response to detection of both the second interaction and the third interaction.

12. The device of claim 11, wherein the electronic circuitry is configured to provide the signal or the change in state in response to detection of the first interaction and then the detection of both the second interaction and the third interaction.

13. The device of claim 11, wherein the electronic circuitry is configured to provide the signal or the change in state in response to detection of both the second interaction and the third interaction simultaneously.

14. The device according to claim 1, the device further comprising:
a reservoir supported by one of the first and second housing portions;
at least one of a drive device and a needle-inserting device supported by the other of the first housing portion and the second housing portion relative to the housing portion that supports the reservoir, such that upon the first housing portion and the second housing portion being operatively engaged at the second position, the reservoir is operatively coupled to the at least one of the drive device and the needle-inserting device.

15. The device according to claim 14,
wherein the at least one of a drive device and a needle-inserting device comprises a drive device for selectively driving fluid from the reservoir; and
wherein the delivery device further comprises control electronics operatively coupled to the electronic circuitry for controlling the drive device based on the signal or the change in state.

16. The device according to claim 15, wherein the control electronics is configured to inhibit operation of the drive device unless the signal or the change in state corresponds to the signal or the change in state when the first housing portion and the second housing portion are in the second position.

17. The device according to claim 15,
wherein the reservoir supports the first interactive element; and
wherein the at least one of a drive device and a needle-inserting device supports the third interactive element in a position to interact with each other when the reservoir is operatively coupled to the at least one of the drive device and the needle-inserting device when the first housing portion and the second housing portion are in the second position.

18. The device according to claim 1, the device further comprising:
a monitoring or treatment device supported by one or more of the first housing portion and the second housing portion;
control electronics operatively coupled to the electronic circuitry for controlling the monitoring or treatment device based on the signal or the change in state.

19. The device according to claim 18, wherein the control electronics is configured to inhibit operation of the monitoring or treatment device unless the signal or the change in state corresponds to the signal or the change in state when the first housing portion and the second housing portion are in the second position.

20. The medical device of claim 1, wherein the electronic circuitry is configured to detect the first interaction and then the second interaction.

21. The medical device of claim 1, wherein the second interactive element and the third interactive element arranged relative to each other along the predefined direction are linearly aligned with each other along the predefined direction.

22. The medical device of claim 1, wherein the at least one guiding structure comprises at least one of a rail, ridge, or raised surface configured to maintain alignment of the first housing portion and the second housing portion as the first housing portion and the second housing portion move relative to each other along the predefined direction.

23. The medical device of claim 1, wherein:
the at least one guiding structure comprises two parts arranged on the second housing portion, forming a space between the two parts, the space is configured to receive at least a portion of the first housing portion;
the two parts are configured to maintain alignment of the first housing portion and the second housing portion along the predefined direction as the first housing portion is received in the space; and
each of the two parts extends parallel to the predefined direction.

24. The medical device of claim 1, further comprising at least one second guiding structure arranged on the first housing portion configured to guide movement of the first housing portion or the second housing portion from the first position to the second position.

25. A method of manufacturing a medical device for treating a user, the method comprising:
adapting a first housing portion to be carried by a user;
configuring a second housing portion to be selectively operatively engaged with and disengaged from the first housing portion, the first housing portion and the second housing portion configured to be movable relative to each other from a first position to a second position in a predefined direction to operatively engage each other at the second position;
supporting a first interactive element on the first housing portion;

supporting a second interactive element on the second housing portion in a position to interact with the first interactive element when the first housing portion and the second housing portion are in the first position;

supporting a third interactive element on the second housing portion in a position to interact with the first interactive element the first housing portion and the second housing portion are in the second position;

arranging the second interactive element and the third interactive element relative to each other along the predefined direction and spaced apart from each other in the predefined direction;

arranging at least one guiding structure on the second portion to guide movement of the first portion or the second portion from the first position to the second position configuring electronic circuitry to detect at least one of a first interaction between the first interactive element and the second interactive element and a second interaction between the first interactive element and the third interactive element; and configuring the circuitry to provide a signal or a change in state in response to detection of at least one of the first interaction and the second interaction.

\* \* \* \* \*